(12) United States Patent
Genesle et al.

(10) Patent No.: US 8,486,931 B2
(45) Date of Patent: *Jul. 16, 2013

(54) SUBSTITUTED OXINDOLE COMPOUNDS

(75) Inventors: Herve Genesle, Ludwigshafen (DE);
Thorsten Oost, Biberach an der Riss (DE); Charles W. Hutchins, Green Oaks, IL (US); Liliane Unger, Ludwigshafen (DE); Wilfried Hornberger, Ludwigshafen (DE); Wilfried Lubisch, Heidelberg (DE); Astrid Netz, Ludwigshafen (DE); Wolfgang Wernet, Ludwigshafen (DE); Alfred Hahn, legal representative, Mannheim (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 169 days.

This patent is subject to a terminal disclaimer.

(21) Appl. No.: 12/529,542

(22) PCT Filed: Feb. 29, 2008

(86) PCT No.: PCT/EP2008/052516
§ 371 (c)(1),
(2), (4) Date: Feb. 12, 2010

(87) PCT Pub. No.: WO2008/107399
PCT Pub. Date: Sep. 12, 2008

(65) Prior Publication Data
US 2010/0286165 A1    Nov. 11, 2010

Related U.S. Application Data

(60) Provisional application No. 60/904,627, filed on Mar. 2, 2007.

(51) Int. Cl.
| A61K 31/4439 | (2006.01) |
| A61K 31/454 | (2006.01) |
| A61K 31/4709 | (2006.01) |
| A61K 31/496 | (2006.01) |
| A61K 31/551 | (2006.01) |

(52) U.S. Cl.
USPC ............... 514/218; 514/253.06; 514/253.09; 514/253.1; 540/575; 544/363; 544/364; 546/177; 546/187; 546/256

(58) Field of Classification Search
None
See application file for complete search history.

(56) References Cited

U.S. PATENT DOCUMENTS

| 5,594,023 | A | 1/1997 | Wagnon et al. | |
| 2004/0180878 | A1* | 9/2004 | Di Malta et al. | 514/218 |
| 2005/0070718 | A1* | 3/2005 | Lubisch et al. | 548/181 |
| 2008/0318923 | A1 | 12/2008 | Sekiguchi et al. | |
| 2009/0005397 | A1 | 1/2009 | Lubisch et al. | |
| 2009/0163492 | A1 | 6/2009 | Oost et al. | |

FOREIGN PATENT DOCUMENTS

| EP | 1659121 | 5/2006 |
| WO | 9518105 | 7/1995 |
| WO | 2005030755 | 4/2005 |
| WO | 2006005609 | 1/2006 |
| WO | 2006072458 | 7/2006 |
| WO | 2006010080 | 9/2006 |
| WO | 2006010081 | 9/2006 |
| WO | 2006010082 | 9/2006 |
| WO | 2008/025735 | * 3/2008 |

OTHER PUBLICATIONS

Banker et al. "Modern Pharmaceutics", 3rd Ed. p. 596 (1996).*
Burger's Medicinal Chemistry, edited by Manfred E.Wolff, 5th Ed. Part 1, pp. 975-977 (1995).*

* cited by examiner

Primary Examiner — Emily Bernhardt
(74) Attorney, Agent, or Firm — Lisa V. Mueller; Michael Best & Friedrich LLP

(57) ABSTRACT

The present invention relates to compounds of the general formula (I)

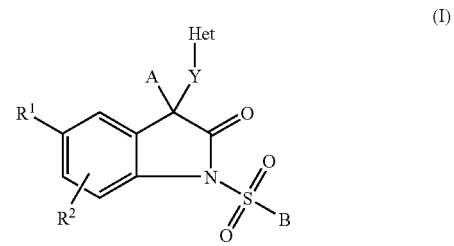

in which A, B, $R^1$, $R^2$ and Het have the meaning given in claim 1;
Y is a bivalent group of the formula

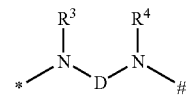

in which D is $C_1$-$C_3$-alkylene, where D may have a substituent $R^5$; $R^3$ is hydrogen, $C_1$-$C_8$-alkyl or together with $R^4$ is $C_1$-$C_3$-alkylene which may have a radical $R^{5a}$, or together with $R^5$ is $C_1$-$C_3$-alkylene, and $R^4$ is hydrogen, $C_1$-$C_8$-alkyl or together with $R^3$ is $C_1$-$C_3$-alkylene which may have a radical $R^{5a}$, or together with $R^5$ is $C_1$-$C_3$-alkylene, where $R^5$ together with $R^{5a}$, where present, are a bond or $C_1$-$C_3$-alkylene; and where one of the following conditions is satisfied: $R^3$ together with $R^4$ is $C_1$-$C_3$-alkylene which may have a radical $R^{5a}$; or $R^3$ together with $R^5$ is $C_1$-$C_3$-alkylene; or $R^4$ together with $R^5$ is $C_1$-$C_3$-alkylene where the radical A is different from phenyl when the radical B is phenyl or naphthyl;
and medicaments which comprise such compounds and the use thereof for the prophylaxis and/or treatment of vasopressin-dependent and/or oxytocin-dependent diseases.

20 Claims, No Drawings

SUBSTITUTED OXINDOLE COMPOUNDS

RELATED APPLICATIONS

This application is filed under 35 USC §371 from PCT Patent Application No. PCT/EP2008/052516, which claims the benefit of provisional application Ser. No. 60/904,627, filed on Mar. 2, 2007, the teachings and content of which are hereby incorporated by reference herein.

The present invention relates to novel substituted oxindole compounds and to the use thereof for the manufacture of medicaments and for the treatment or prophylaxis of vasopressin- and/or oxytocin-dependent disorders.

Vasopressin (AVP) is an endogenous hormone which exerts a large number of effects on organs and tissues. Vasopressin is related to oxytocin (OT), so that the two peptides are combined into a vasopressin/oxytocin family. It is suspected that the vasopressin/oxytocin system is involved in various pathological states. At present, three vasopressin receptors (V1a, V1b or V3 and V2 receptors) and one oxytocin receptor (OT receptor), via which vasopressin and oxytocin mediate their effects, are known. Antagonists of these receptors, especially including antagonists which specifically bind only to one of the above receptors, represent novel therapeutic approaches to the treatment of diseases. (M. Thibonnier, Exp. Opin. Invest. Drugs 1998, 7(5), 729-740). For example, it has been found that a selective antagonist of the vasopressin V1b receptor exerts anxiolytic and antidepressant effects in animal models (Griebel et al., PNAS 2002, 99, 6370; Serradeil-Le Gal et al., J. Pharm. Exp. Ther. 2002, 300, 1122). Since the models described have a certain predictive value for the clinical effects to be expected, antagonists of the V1b receptor are of particular interest for the treatment of emotional disturbances or disorders such as, for example, stress, anxiety states and/or depression.

WO 95/18105 describes substituted oxindole compounds which have a benzyl substituent or a benzenesulfonyl substituent in position 1. One of the two substituents in position 3 of the oxindole structure of these compounds is attached via a nitrogen atom. 4-(Amino-$C_2$-$C_{10}$-alkyl)piperazin-1-yl is mentioned inter alia as example of such a substituent in position 3.

WO 2005/030755 describes oxindole compounds of the general formula

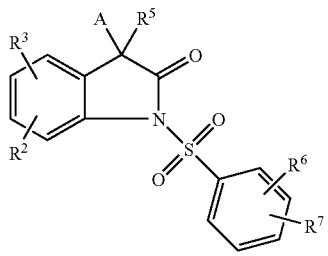

in which A is a mono- or bicyclic, aromatic or partly aromatic heterocycle. In one of the disclosed embodiments, $R^5$ is an unsaturated, saturated or partly saturated, mono-, bi- or tricyclic carbo- or heterocycle which may optionally be substituted by an unsaturated, saturated or partly saturated, mono-, bi- or tricyclic carbo- or heterocycle and which is linked to position 3 of the oxindole structure via a bivalent functional group or directly.

WO 2006/005609 describes substituted oxindole compounds which have a mono- or bicyclic aryl substituent linked via a sulfonyl group in position 1. In addition, these compounds have as substituents in position 3 an aryl group and a saturated or partly saturated nitrogen-containing ring which is substituted by a saturated nitrogen-containing heterocycle and which is linked via a bivalent functional group to the oxindole structure.

WO 2006/100080 describes compounds of similar structure which differ from those in WO 2006/005609 in that the saturated or partly saturated nitrogen-containing ring which is linked via a bivalent group to position 3 of the oxindole structure is substituted by a heteroaromatic radical.

WO 2006/100081 describes substituted oxindole compounds which have a mono-, bi- or tricyclic heteroaryl substituent which is linked via a sulfonyl group in position 1. These compounds have as substituents in position 3 a phenyl group and a saturated nitrogen-containing ring or a saturated carbocycle, which is in each case substituted by a nitrogen-containing mono- or bicyclic, heteroaromatic radical and is linked via a bivalent functional group to the oxindole structure.

WO 2006/072458 describes substituted oxindole compounds which have a mono- or bicyclic aryl substituent linked via a sulfonyl group to position 1 of the oxindole structure. One of the two substituents in position 3 of the oxindole structure is $C_6$-$C_{10}$-aryl. The second substituent in position 3 is attached via a nitrogen atom. 4-alkylpiperazin-1-yl or 4-cycloalkylpiperazin-1-yl is mentioned inter alia as example of such a substituent in position 3.

WO 2006/100082 describes structurally similar compounds which differ from the compounds of WO 2006/072458 in that the aryl groups in the substituents in position 1 and position 3 of the oxindole structure may also be replaced by heteroaryl groups.

PCT/EP2007/058839 (the unpublished German patent application 102006040915.9) describes substituted oxindole compounds which have a mono- or bicarbocyclic, aromatic or partly aromatic substituent linked via a sulfonyl group in position 1. These compounds additionally have as substituents in position 3 an aryl group and a 5- or 6-membered, saturated or unsaturated heterocycle which is connected via a bivalent group to the oxindole structure, where the bivalent group comprises two terminal N atoms and a mono- or polycyclic heterocycle.

It is an object of the present invention to provide further compounds for the treatment or prophylaxis of various vasopressin-dependent disorders. It is intended in particular that the compounds are distinguished from the compounds known in the prior art by an improved metabolic stability and/or an improved pharmacological activity and/or selectivity vis-a-vis the vasopressin receptors. The advantages can moreover be shown for example by using suitable models which enable prognostic statements to be made about the desired use in the treatment of patients.

It has now been found, surprisingly, that this and further objects is achieved by the compounds of the general formula (I) which are described hereinafter, their salts, their prodrugs and the N-oxides of compounds of the general formula (I).

The present invention thus relates to compounds of the general formula (I)
in which

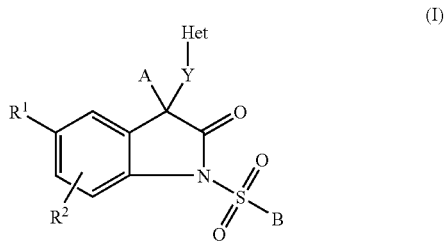

A is phenyl or a 5- to 6-membered heteroaromatic ring which has 1, 2, 3 or 4 heteroatoms which are selected from N, O and S, where the aforementioned radicals are unsubstituted or have one, two, three or four substituents $R^A$, where
$R^A$ is selected independently of one another from halogen, CN, $NO_2$, $C_1$-$C_6$-alkyl, $C_3$-$C_7$-cycloalkyl, $C_1$-$C_6$-haloalkyl, $C_1$-$C_6$-alkoxy, $C_1$-$C_6$-halo-alkoxy, $C_1$-$C_6$-alkylcarbonyl, $C_1$-$C_6$-alkylcarbonyloxy, $C_1$-$C_6$-alkyloxycarbonyl, $C_1$-$C_6$-alkylsulfonyl, $C_1$-$C_6$-alkylthio, $C_2$-$C_6$-alkenyl, $C_2$-$C_6$-alkynyl, $C_2$-$C_6$-alkenyloxy, $C_2$-$C_6$-alkynyloxy, or a group —$R^{a1}$—($C_0$-$C_4$-alkylene)-$R^{a2}$, in which
$R^{a1}$ is selected from a chemical bond, O, $CH_2$—O, $NR^{a3}$, $CH_2$—$NR^{a3}$, $NR^{a3}$—CO and $CH_2$—$NR^{a3}$—CO;
$R^{a2}$ is selected from $NH_2$, $C_1$-$C_4$-alkylamino, di-$C_1$-$C_4$-alkylamino, ($C_1$-$C_4$-alkyl)($C_1$-$C_4$-alkoxy-$C_1$-$C_4$-alkyl)N and an N-bonded 5- or 6-membered, saturated or unsaturated nitrogen heterocycle which may have 1 or 2 substituents selected from $C_1$-$C_4$-alkyl, formyl and $C_1$-$C_4$-alkylcarbonyl, and which may have a further heteroatom selected from O, N and S as ring member,
$R^{a3}$ are selected independently of one another from hydrogen and $C_1$-$C_4$-alkyl;
or two of the adjacent radicals $R^A$ may form together with the ring atoms to which they are bonded an optionally substituted, fused-on partly saturated 5- to 7-membered carbocycle, cyclic ether or cyclic acetal;
B is phenyl, naphthyl or a 5- to 10-membered mono- or bicyclic heteroaromatic ring which has 1, 2, 3 or 4 heteroatoms which are selected from N, O and S, where the aforementioned radicals are unsubstituted or have one, two, three or four substituents $R^B$, where
$R^B$ is selected independently of one another from halogen, CN, $NO_2$, hydroxy, $C_1$-$C_6$-alkyl, $C_3$-$C_7$-cycloalkyl, $C_1$-$C_6$-haloalkyl, $C_1$-$C_6$-alkoxy, $C_1$-$C_6$-haloalkoxy, $C_1$-$C_6$-alkylcarbonyl, $C_1$-$C_6$-alkylcarbonyloxy, $C_1$-$C_6$-alkyloxycarbonyl, $C_1$-$C_6$-alkylsulfonyl, $C_1$-$C_6$-alkylthio, amino, $C_1$-$C_4$-alkylamino, di($C_1$-$C_4$-alkyl)amino, $C_2$-$C_6$-alkenyl, $C_2$-$C_6$-alkynyl, $C_2$-$C_6$-alkenyloxy, $C_2$-$C_6$-alkynyloxy,
or two of the adjacent radicals $R^B$ may form together with the ring atoms to which they are bonded an optionally substituted, fused-on partly saturated 5- to 7-membered carbocycle, cyclic ether or cyclic acetal,
$R^1$ is hydrogen, halogen, CN, $NO_2$, $C_1$-$C_6$-alkyl, $C_1$-$C_6$-haloalkyl, $C_1$-$C_6$-alkoxy or $C_1$-$C_6$-haloalkoxy,
$R^2$ is hydrogen, halogen, CN, $NO_2$, $C_1$-$C_6$-alkyl, $C_1$-$C_6$-haloalkyl, $C_1$-$C_6$-alkoxy and $C_1$-$C_6$-haloalkoxy,
Y is a cyclic bivalent group of the formula

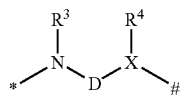

in which
* is the linkage to the oxindole unit,
# is the linkage to the Het group,
D is $C_1$-$C_3$-alkylene, where D may have a substituent $R^5$,
X is N or CH,
$R^3$ is hydrogen, $C_1$-$C_6$-alkyl or together with $R^4$ is $C_1$-$C_3$-alkylene which may have a radical $R^{5a}$, or together with $R^5$ is $C_1$-$C_3$-alkylene, and $R^4$ is hydrogen, $C_1$-$C_6$-alkyl or together with $R^3$ is $C_1$-$C_3$-alkylene which may have a radical $R^{5a}$, or together with $R^5$ is $C_1$-$C_3$-alkylene,
where $R^5$ together with $R^{5a}$, if present, are a bond or $C_1$-$C_3$-alkylene, and
where one of the following conditions is satisfied:
$R^3$ together with $R^4$ is $C_1$-$C_3$-alkylene which may have a radical $R^{5a}$, or
$R^3$ together with $R^5$ is $C_1$-$C_3$-alkylene or
$R^4$ together with $R^5$ is $C_1$-$C_3$-alkylene,
where the aforementioned $C_1$-$C_3$-alkylene is unsubstituted or 1 to 4 of the hydrogen atoms of the $C_1$-$C_3$-alkylene are replaced independently of one another by halogen, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylcarbonyl, di-$C_1$-$C_4$-alkylamino, di-$C_1$-$C_4$-alkylamino-$C_1$-$C_4$-alkyl or $C_3$-$C_7$-cycloalkyl, and/or two geminal hydrogen atoms of the $C_1$-$C_3$-alkylene together with the carbon to which they are bonded are replaced by a carbonyl unit, and
Het is a 5- or 6-membered saturated, unsaturated or aromatic heterocyclic radical which has 1, 2, 3 or 4 heteroatoms which are selected from N, O and S, where the radical is unsubstituted or has one, two or three identical or different substituents $R^{Het}$ which are selected independently of one another from halogen, CN, $NO_2$, $C_1$-$C_6$-alkyl, $C_3$-$C_7$-cycloalkyl, $C_1$-$C_6$-haloalkyl, $C_1$-$C_6$-alkyloxy, $C_1$-$C_6$-haloalkoxy, $C_3$-$C_7$-cycloalkoxy, di($C_1$-$C_6$-alkyl)amino, $C_1$-$C_6$-alkylthio, $C_1$-$C_6$-alkylsulfonyl, $C_2$-$C_6$-alkenyl, $C_2$-$C_6$-alkynyl, $C_2$-$C_6$-alkenyloxy and $C_2$-$C_6$-alkynyloxy,
where the radical A is different from phenyl which is unsubstituted or has one, two, three or four substituents $R^A$ when the radical B is phenyl or naphthyl which are unsubstituted or have one, two, three or four substituents $R^B$.

The present invention also relates to the salts of compounds of the general formula (I), especially acid addition salts of compounds of the formula (I). The present invention further relates to the prodrugs of the compounds of the general formula (I). The present invention further relates to the N-oxides of the compounds of the general formula (I). Compounds of the general formula (I) may exist in the form of their tautomers. The present invention thus further relates to the tautomeric forms of the compounds of the general formula (I).

The compounds of the invention of the formula (I) have a chirality center in position 3 of the oxindole structure. The compounds of the formula (I) are thus optically active substances. If the compounds of the general formula (I) have a further chirality center, diastereomers of these compounds exist. The compounds of the invention of the formula (I) can accordingly exist as a mixture of diastereomers, or as a mixture of diastereomers in which one of the two diastereomers is enriched, or as essentially diastereomerically pure compounds (diastereomeric excess de>90%). The compounds are preferably in the form of essentially diastereomerically pure compounds. The respective diastereomers may in turn be in the form of a mixture of enantiomers, for example as racemate, or of a mixture of enantiomers in which one of the two enantiomers is enriched, or of essentially enantiomerically pure compounds (enantiomeric excess ee>90%). The respective diastereomers are preferably in the form of essentially enantiomerically pure compounds. Compounds which are essentially diastereomerically pure and enantiomerically pure (de>90%, ee>90%) are particularly preferred.

General formula (I) therefore also encompasses diastereomeric and/or enantiomeric forms of the compounds of the general formula (I).

The expression "halogen" stands in the context of the present invention for fluorine, chlorine, bromine or iodine, preferably fluorine, chlorine or bromine and particularly preferably for fluorine or chlorine.

The expression "$C_1$-$C_6$-alkyl" as used herein and the alkyl units of $C_1$-$C_6$-alkoxy, $C_1$-$C_6$-alkylcarbonyl, $C_1$-$C_6$-alkyloxycarbonyl, $C_1$-$C_6$-alkylcarbonyloxy, $C_1$-$C_6$-alkyl-sulfonyl, $C_1$-$C_6$-alkylthio or di($C_1$-$C_4$-alkyl)amino stands in the context of the present invention for a straight-chain or branched saturated hydrocarbon radical having 1 to 6 carbon atoms, such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methyl-butyl, 1,2-dimethylpropyl, 1,1-dimethylpropyl, 2,2-dimethylpropyl, 1-ethylpropyl, n-hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl. The alkyl radicals are preferably selected from $C_1$-$C_4$-alkyl, such as methyl, ethyl, n-propyl, i-propyl, n-butyl, sec-butyl or t-butyl.

The expression "$C_3$-$C_7$-cycloalkyl" stands in the context of the present invention for a cyclic hydrocarbon radical having 3 to 7 ring members, such as cyclopropyl, cyclobutyl, cyclopentyl, cyclohexyl or cycloheptyl.

The expression "$C_1$-$C_6$-haloalkyl" as used herein and in the haloalkyl unit of $C_1$-$C_6$-haloalkoxy stands in the context of the present invention for straight-chain or branched $C_1$-$C_6$-alkyl radicals in which the hydrogen atoms of these radicals are partly or completely replaced by halogen atoms. The haloalkyl radicals are preferably selected from $C_1$-$C_4$-haloalkyl, particularly preferably from $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The expression "$C_2$-$C_6$-alkenyl" as used herein and in $C_2$-$C_6$-alkenyloxy stands in the context of the present invention for straight-chain or branched unsaturated hydrocarbon radicals having 2 to 6 carbon atoms and at least one carbon-carbon double bond in any position. The alkenyl radicals are preferably selected from $C_2$-$C_4$-alkenyl such as, for example, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl.

The expression "$C_2$-$C_6$-alkynyl" as used herein and in $C_2$-$C_6$-alkynyloxy stands in the context of the present invention for straight-chain or branched unsaturated hydrocarbon radicals having 2 to 6 carbon atoms and at least one carbon-carbon triple bond in any position. The alkynyl radicals are preferably selected from $C_2$-$C_4$-alkynyl such as, for example, ethynyl, prop-1-yn-1-yl, prop-2-yn-1-yl, n-but-1-yn-1-yl, n-but-1-yn-3-yl, n-but-1-yn-4-yl or n-but-2-yn-1-yl.

The expression "bivalent group" stands in the context of the present invention for an organic group which is able to form two covalent single bonds.

The expression "$C_1$-$C_3$-alkylene" stands in the context of the present invention for methylene, eth-1,2-ylene, prop-1,3-ylene.

The term "5- or 6-membered heterocyclic radical" includes both saturated radicals which are also referred to as heterocycloalkyl in the context of the present invention, and unsaturated radicals and aromatic radicals which are also referred to as heteroaromatic rings in the context of the present invention. The heterocyclic radicals have 1, 2 or 3 heteroatoms as ring members. The heteroatoms are in this case selected from O, S and N.

Examples of 5- or 6-membered heterocycloalkyl are piperidinyl, piperazinyl, morpholinyl, pyrrolidinyl, oxazolidinyl, tetrahydrofuryl, dioxolanyl and dioxanyl.

Examples of unsaturated 5- or 6-membered heterocyclic radicals are di- and tetrahydropyridinyl, pyrrolinyl, oxazolinyl and dihydrofuryl.

Examples of "heteroaromatic rings" include in the context of the present invention mono- or polycyclic rings which have at least one heteroatom selected from N, O and S as ring member and include, based on the respective ring size, an aromatic number of unsaturated bonds. This expression preferably describes monocyclic 5- or 6-membered heteroaromatic rings and 8- to 10-membered bicyclic heteroaromatic rings. Examples of heteroaromatic rings are 2-furyl, 3-furyl, 2-pyrrolyl, 3-pyrrolyl, 2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl, triazinyl, indolinyl, benzothienyl, naphthothienyl, benzofuranyl, chromenyl, indolyl, isoindolyl, indazolyl, quinolyl, isoquinolyl, phthalazinyl, quinoxalinyl, benzimidazolyl and benzoxazolyl, 2,3-dihydro-1,4-benzodioxinyl, 1,3-benzodioxolyl, and 2,1,3-benzothiadiazolyl.

The expression "optionally substituted" is used in the context of the present invention in connection with radicals and groups which are unsubstituted or substituted one or more times, more preferably one, two or three times, particularly preferably once or twice. Suitable substituents in the sense of this expression include, unless stated otherwise, for example halogen, CN, $NO_2$, $NH_2$, OH, COOH, $C_1$-$C_4$-alkyl, $C_1$-$C_4$-alkoxy, $C_1$-$C_4$-haloalkyl, $C_1$-$C_4$-haloalkoxy, ($C_1$-$C_4$-alkyl)amino and di($C_1$-$C_4$-alkyl)amino.

The expression "physiologically tolerated salt" refers in the context of the present invention to salts which are formed for example with the following anions: chloride, methanesulfonate, formate, trifluoroacetate and/or acetate. Physiologically tolerated salts of the compounds of the formula (I) are in particular acid addition products of these compounds. Further acids suitable as salt formers are listed for example in "Fortschritte der Arzneimittelforschung", 1966, Birkhäuser Verlag, Vol. 10, pp. 224-285.

The expression "prodrugs" refers in the context of the present invention to compounds which are transformed in vivo under metabolic conditions, for example by enzymatic degradation, into compounds of the general formula (I). Typical examples of prodrugs are listed for example in C. G. Wermeth (ed.): The Practice of Medicinal Chemistry, Academic Press, San Diego, 1996, pages 671-715. Examples of prodrugs include phosphates, carbamates, amino acids, esters, amides, peptides, ureas and the like. In the case of the present application suitable prodrugs are for example compounds of the formula I, wherein a nitrogen atom of a nitrogen-containing radical Het which is not part of a double bond in Het forms an amide/peptide bond, e.g., the nitrogen ring atom in the radical Het carries a $C_1$-$C_4$ alkylcarbonyl group, such as acetyl, propionyl, n-propylcarbonyl, isopropylcarbonyl, n-butylcarbonyl or tert-butylcarbonyl (pivaloyl), a benzoyl group or an amino acid residue linked via a carbonyl group (CO), such as an amino acid residue selected from glycine, alanine, phenylalanine, serine and the like linked via a carbonyl group. Further examples of prodrugs include alkylcarbonyloxyalkyl carbamates, wherein for example a nitrogen atom of a nitrogen-containing radical Het which is not part of a double bond in Het carries a radical of the formula —C(=O)—O—CHR$^\alpha$—O—C(=O)—R$^\beta$, in which R$^\alpha$ and R$^\beta$ are independently of each other C$_1$-C$_4$ alkyl. Such carbamates are listed for example in J. Alexander, R. Cargill, S. R. Michelson, H. Schwam, J. Medicinal Chem. 1988, 31(2), 318-322. Under metabolic conditions, the aforementioned radicals are cleaved and compounds of the formula (I), wherein the nitrogen ring atom in the radical Het carries a hydrogen atom, are obtained. Therefore, said prodrugs are also part of the invention.

The compounds of the general formula (I) may when they include a basic N atom such as, for example, the N atom of a pyridine substituent exist as N-oxides.

A first embodiment of the present invention relates to compounds of the general formula (I), their salts, their prodrugs and their N-oxides, in which A is phenyl which is unsubstituted or has one, two, three or four substituents R$^A$, where the substituents R$^A$ have independently of one another one of the meanings given above, and B is a 5- to 10-membered mono- or bicyclic heteroaromatic ring which is unsubstituted or has one, two, three or four substituents R$^B$, where the substituents R$^B$ have independently of one another one of the meanings given above.

A second embodiment of the present invention relates to compounds of the general formula (I), their salts, their prodrugs and their N-oxides, in which A is a 5- to 6-membered heteroaromatic ring which has 1, 2, 3 or 4 heteroatoms which are selected from N, O and S and which is unsubstituted or has one, two, three or four substituents R$^A$, where the substituents R$^A$ have independently of one another one of the meanings given above, and B is phenyl or naphthyl, where the aforementioned radicals are unsubstituted or have one, two, three or four substituents R$^B$, where the substituents R$^B$ have independently of one another one of the meanings given above.

A third embodiment of the present invention relates to compounds of the general formula (I), their salts, their prodrugs and their N-oxides, in which A is a 5- to 6-membered heteroaromatic ring which has 1, 2, 3 or 4 heteroatoms which are selected from N, O and S and which is unsubstituted or has one, two, three or four substituents R$^A$, where the substituents R$^A$ have independently of one another one of the meanings given above, and B is a 5- to 10-membered mono- or bicyclic heteroaromatic ring which is unsubstituted or has one, two, three or four substituents R$^B$, where the substituents R$^B$ have independently of one another one of the meanings given above.

The preferences in relation to the radicals A, R$^A$, B, R$^B$, R$^1$, R$^2$, Y, D, R$^3$, R$^4$ and Het described hereinafter apply independently of one another both in relation to the radicals considered separately and in any combination of the radicals. In particular, the preferences in relation to all radicals apply in combination with the previously described specific embodiments of the present invention.

The substituents R$^A$ are independently of one another and independently of the specific embodiment preferably halogen, CN, NO$_2$, C$_1$-C$_6$-alkyl, C$_1$-C$_6$-haloalkyl, C$_1$-C$_6$-alkoxy, C$_1$-C$_6$-haloalkoxy, C$_3$-C$_7$-cycloalkyl or di(C$_1$-C$_4$-alkyl) amino. R$^A$ is particularly preferably fluorine, chlorine, CN, NO$_2$, C$_1$-C$_4$-alkyl, C$_1$-C$_4$-haloalkyl, C$_1$-C$_4$-alkoxy, C$_1$-C$_4$-halo-alkoxy, C$_3$-C$_7$-cycloalkyl or di(C$_1$-C$_4$-alkyl)amino. The substituents R$^A$ are very particularly preferably fluorine, chlorine, methyl, ethyl, isopropyl, cyclopropyl, methoxy, ethoxy, isopropyloxy or dimethylamino.

The radical A in the compounds of the invention may also have a substituent R$^A$ of the formula —R$^{a1}$—(C$_0$-C$_4$-alkylene)-R$^{a2}$ which preferably has a structure of the following formulae:

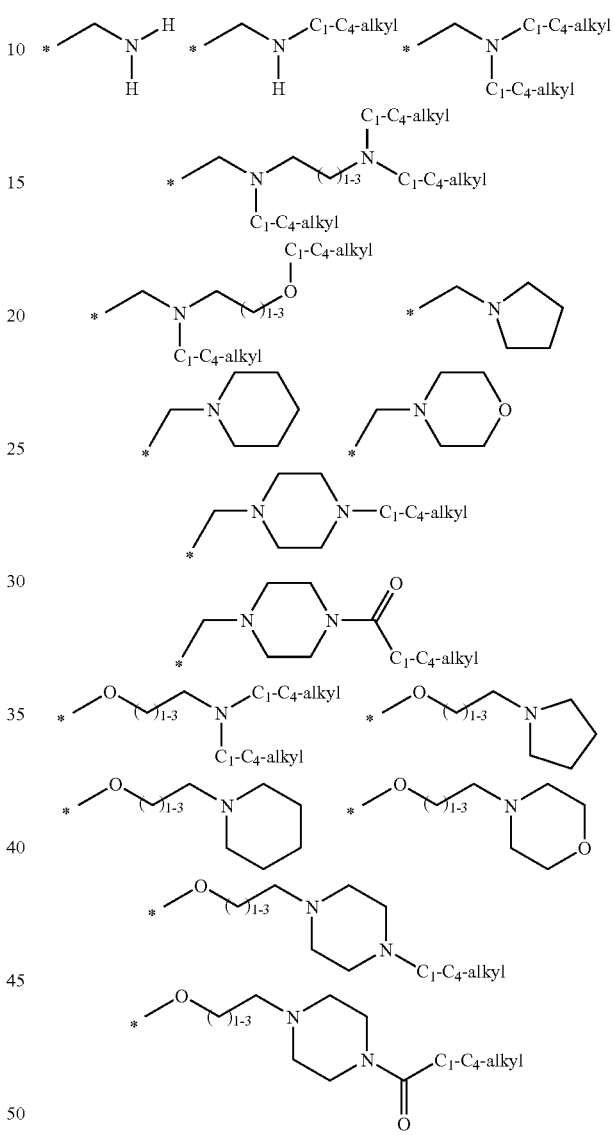

In a preferred embodiment of the present invention, the radicals A have 1 or 2 substituents R$^A$.

In a further preferred embodiment of the present invention, the radical A is unsubstituted.

In the first embodiment, the radical A is preferably a phenyl radical which has a substituent R$^A$ which is linked in position 2 or is a phenyl radical which has a first radical R$^A$ which is linked in position 2, and a further radical R$^A$ which is linked in position 3, 4 or 5, and specifically in position 5. The above statements concerning preferred radicals R$^A$ apply. The radical A is particularly preferably 2-methoxyphenyl, 2-ethoxyphenyl, 2-ethoxy-5-methylphenyl, 2-ethoxy-5-ethylphenyl, 2-ethoxy-5-isopropyl phenyl, 2-ethoxy-5-cyclopropylphenyl, 2-chlorophenyl, 2,3-dimethoxyphenyl, 2,4-dimethoxyphenyl, 2-ethoxy-4-fluorophenyl, 2,5-dimethoxyphenyl, 2-ethoxy-3-methoxyphenyl, 2-ethoxy-4-methoxyphenyl, 2-ethoxy-5-methoxyphenyl, 2-isopropyloxy-5-methoxyphenyl, 2-methoxy-5-methylphenyl, 2-ethoxy-5-ethylphenyl, 2-isobutyloxy-5-methoxyphenyl, 2-methoxy-5-(dimethylaminomethyl)phenyl or 2-methoxy-5-(methylaminomethyl)phenyl. A in this embodiment is very particularly preferably 2-methoxyphenyl, 2-ethoxyphenyl, 2,5-dimethoxyphenyl or 2-ethoxy-5-methoxyphenyl.

In the second and third embodiment of the present invention, A is preferably a pyridine radical, in particular is 3-pyridyl which is unsubstituted or has a substituent $R^A$ which is linked in position 2, or is 3-pyridyl which has a first radical $R^A$ which is linked in position 2, and a further radical $R^A$ which is linked in position 4, 5 or 6, and specifically in position 5. The above statements concerning preferred radicals $R^A$ apply. The radical A in this embodiment is particularly preferably 2-methoxypyridin-3-yl, 2-ethoxypyridin-3-yl, 2-ethoxy-5-methylpyridin-3-yl, 2-ethoxy-5-ethylpyridin-3-yl, 2-ethoxy-5-isopropylpyridin-3-yl, 2-ethoxy-5-cyclopropylpyridin-3-yl, 2-ethoxy-6-methoxypyridin-3-yl, 2-ethoxy-6-dimethylaminopyridin-3-yl, 6-chloro-2-methoxypyridin-3-yl, 6-chloro-2-ethoxy-pyridin-3-yl or 2,6-difluoropyridin-3-yl. In this embodiment, A is very particulary preferably 6-chloro-2-ethoxypyridin-3-yl. Preference is likewise given to compounds of the formula (I), their salts, their prodrugs and their N-oxides, in which A is pyridin-2-yl or 3-methylpyridin-2-yl.

In a preferred embodiment of the present invention, the radical B has 1 or 2 substituents $R^B$.

The substituents $R^B$ are selected independently of one another and independently of the specific embodiment preferably from halogen, CN, $NO_2$, amino, hydroxy, $C_1$-$C_6$-alkyl, $C_1$-$C_6$-haloalkyl, $C_1$-$C_6$-alkoxy, $C_1$-$C_6$-haloalkoxy, $C_1$-$C_4$-alkylamino, di($C_1$-$C_4$-alkyl)amino and $C_3$-$C_7$-cycloalkyl. $R^B$ is particularly preferably fluorine, chlorine, CN, $NO_2$, $C_1$-$C_4$-alkyl, $C_1$-$C_4$-haloalkyl, $C_1$-$C_4$-alkoxy, $C_1$-$C_4$-haloalkoxy or $C_3$-$C_7$-cycloalkyl. The substituents $R^B$ are very particularly preferably fluorine, chlorine, methyl, ethyl, cyclopropyl, methoxy or ethoxy.

In a further preferred embodiment of the present invention, the radical B is unsubstituted.

In the first and third embodiment, the radical B is preferably pyridin-2-yl or quinolin-8-yl, each of which are unsubstituted or have one, two, three or four substituents $R^B$. B in this embodiment is particularly preferably pyridin-2-yl or quinolin-8-yl which is unsubstituted or has a substituent $R^B$ in position 5.

Among these, preferred radicals B are those selected from pyridin-2-yl, 5-methylpyridin-2-yl, 5-methoxypyridin-2-yl, quinolin-8-yl, 3-methylquinolin-8-yl, 4-methylquinolin-8-yl, 5-methylquinolin-8-yl, 5-methoxyquinolin-8-yl, 4-ethyl-8-quinolinyl, 5-ethoxyquinolin-8-yl, 5-chloroquinolin-8-yl and 5-fluoroquinolin-8-yl. In this specific embodiment, B is very particularly preferably 5-methoxypyridin-2-yl, quinolin-8-yl or 5-methoxyquinolin-8-yl.

In the second embodiment, the radical B is preferably 2,3-dimethoxyphenyl, 2,4-dimethoxyphenyl, 3,5-dimethoxyphenyl, 2-ethoxy-4-methoxyphenyl, 4-amino-2-methoxyphenyl, 4-methoxy-2-nitrophenyl, 4-methoxynaphthyl, 2-trifluoromethyl-4-cyanophenyl, 8-methoxynaphthyl, 4,8-dimethoxynaphthyl, 4-fluoronaphthyl or 4-chloronaphthyl. In this embodiment, the radical B is particularly preferably 2,4-dimethoxyphenyl.

The substituent $R^1$ is preferably CN, chlorine, methyl or methoxy. The substituent $R^1$ is particularly preferably CN.

The substituent $R^2$ is preferably hydrogen.

In particular, $R^1$ is CN and the substituent $R^2$ is hydrogen.

In a preferred embodiment of the present invention, the substituents $R^3$ and $R^4$ in the bivalent group Y together are $C_1$-$C_3$-alkylene which may have a group $R^{5a}$. The alkylene units in the previously described embodiment are moreover independently of one another unsubstituted or 1 to 4 of the hydrogen atoms of the alkylene units are replaced by halogen, $C_1$-$C_4$-alkyl, $C_1$-$C_4$-alkoxy, $C_1$-$C_4$-haloalkyl, $C_1$-$C_4$-haloalkoxy, $C_1$-$C_4$alkylcarbonyl, di-$C_1$-$C_4$-alkylamino, di-$C_1$-$C_4$-alkylamino-$C_1$-$C_4$-alkyl or $C_3$-$C_7$-cycloalkyl, preferably by $C_1$-$C_4$-alkyl, and/or two geminal hydrogen atoms of the alkylene units together with the carbon to which they are linked are replaced by a carbonyl unit.

Preferred examples of such bivalent cyclic groups Y are shown below:

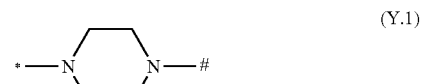

(Y.1)

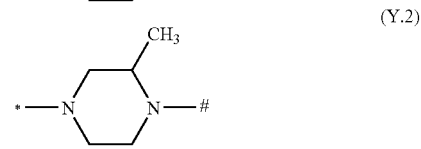

(Y.2)

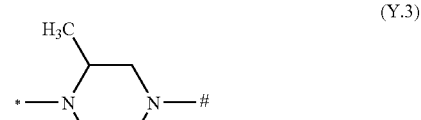

(Y.3)

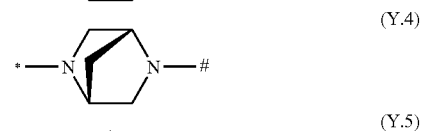

(Y.4)

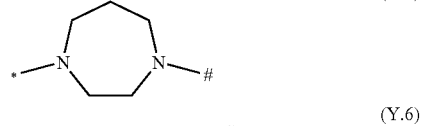

(Y.5)

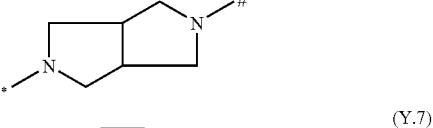

(Y.6)

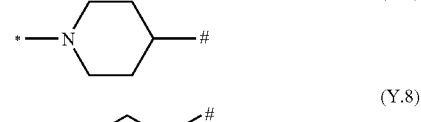

(Y.7)

(Y.8)

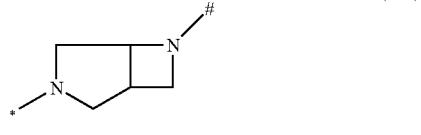

(Y.9)

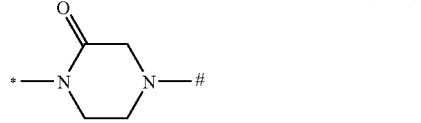

(Y.10)

-continued

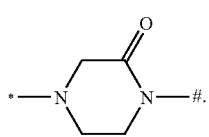
(Y.11)

The bivalent cyclic arrows Y are particularly preferably selected from the groups

(Y.1)

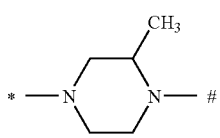
(Y.2)

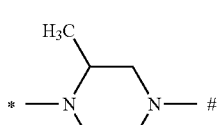
(Y.3)

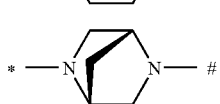
(Y.4)

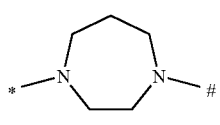
(Y.5)

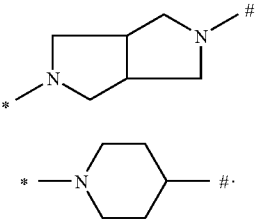
(Y.6)

(Y.7)

The cyclic groups Y in the compounds of the general formula (I) are very particularly preferably piperazine-1,4-diyl (Y.1), piperidine-1,4-diyl (Y.7) or homopiperazine-1,4-diyl (Y.5).

In a preferred embodiment of the present invention, Het in the compounds of the formula (I) is a 5- or 6-membered aromatic heterocyclic radical which has 1, 2, 3 or 4 heteroatoms which are selected from N, O and S, where the radical is unsubstituted or has one, two or three identical or different substituents $R^{Het}$ as defined above.

The group Het in this embodiment is preferably selected from 2-pyridyl, 3-pyridyl, 4-pyridyl, 4-pyrimidinyl, 2-triazinyl or 1,3-thiazol-2-yl, which are unsubstituted or have one, two or three identical or different substituents $R^{Het}$.

The substituents $R^{Het}$ are preferably selected independently of one another from halogen, CN, $NO_2$, $C_1$-$C_6$-alkyl, $C_1$-$C_6$-haloalkyl, $C_1$-$C_6$-alkyloxy, $C_1$-$C_6$-haloalkoxy and $C_3$-$C_7$-cycloalkyl. The substituents $R^{Het}$ are particularly preferably selected from fluorine, chlorine, cyano, $C_1$-$C_4$-alkyl, $C_1$-$C_4$-alkoxy and $C_3$-$C_7$-cycloalkyl.

The group Het in the compounds of the formula (I) is particularly preferably pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-isopropylpyridin-4-yl or 3-fluoropyridin-4-yl. Likewise, the group Het in the compounds of the formula (I) is particularly preferably 2-ethylpyridin-4-yl or preferably 2-isopropylpyridin-4-yl.

Het in the compounds of the general formula (I) is very particularly preferably pyridin-4-yl which is unsubstituted or has a substituent $R^{Het}$.

In a further preferred embodiment of the present invention, Het in the compounds of the formula (I) is a 5- or 6-membered saturated heterocyclic radical which has 1, 2, 3 or 4 heteroatoms which are selected from N, O and S, where the radical is unsubstituted or has one, two or three identical or different substituents $R^{Het}$ as defined in claim 1.

In this embodiment of the present invention, Het is preferably a piperidin-2-yl, piperidin-3-yl, piperidin-4-yl, piperazin-1-yl or piperazin-2-yl radical, which are in each case unsubstituted or have one, two or three identical or different substituents $R^{Het}$ which are selected independently of one another from halogen, CN, $NO_2$, $C_1$-$C_6$-haloalkyl, $C_1$-$C_6$-alkyloxy, $C_1$-$C_6$-haloalkoxy and $C_3$-$C_7$-cycloalkyl.

In a specific embodiment of the present invention, the groups Het are unsubstituted or have a substituent $R^{Het}$.

In particularly preferred embodiments, the group Y-Het stands for radicals of the following formulae:

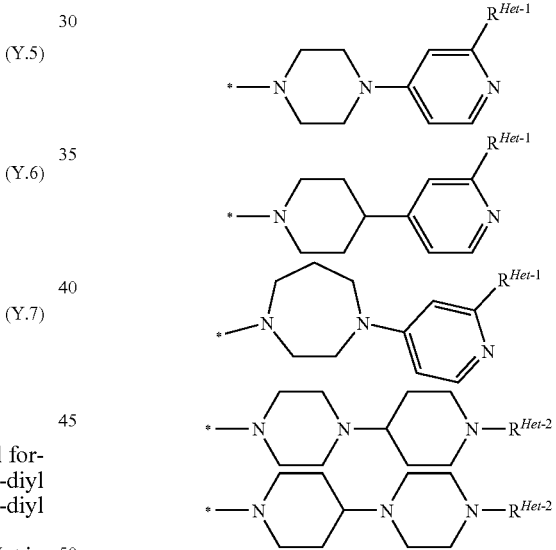

in which * indicates the linkage to the oxindole unit, $R^{Het-1}$ is hydrogen, methyl or isopropyl, and in which $R^{Het-2}$ is hydrogen or methyl.

In a very particularly preferred embodiment of the present invention, Y in the compounds of the formula (I) is piperazine-1,4-diyl and Het is pyridin-4-yl.

Preference is given to compounds of the general formula (I), their salts, their prodrugs and their N-oxides in which A is a pyridine radical, in particular is 3-pyridyl which is unsubstituted or has a substituent $R^A$ which is linked in position 2, or is 3-pyridyl which has a first radical $R^A$ which is linked in position 2 and a further radical $R^A$ which is linked in position 4, 5 or 6, and specifically in position 5, such as, for example, 2-methoxy-pyridin-3-yl, 2-ethoxypyridin-3-yl, 2-ethoxy-5-methylpyridin-3-yl, 2-ethoxy-5-ethylpyridin-3-yl, 2-ethoxy-5-isopropylpyridin-3-yl, 2-ethoxy-5-cyclopropylpyridin-3- yl, 2-ethoxy-6-methoxypyridin-3-yl, 2-ethoxy-6-dimethylaminopyridin-3-yl, 6-chloro-2-methoxy-pyridin-3-yl, 6-chloro-2-ethoxypyridin-3-yl or 2,6-difluoropyridin-3-yl and specifically is 6-chloro-2-ethoxypyridin-3-yl, and B is phenyl or naphthyl, which have in each case one or two substituents $R^B$, such as, for example, 2,3-dimethoxyphenyl, 2,4-dimethoxyphenyl, 3,5-dimethoxyphenyl, 2-ethoxy-4-methoxyphenyl, 4-amino-2-methoxyphenyl, 4-methoxy-2-nitrophenyl, 4-methoxynaphthyl, 2-trifluoromethyl-4-cyanophenyl, 8-methoxynaphthyl, 4,8-dimethoxynaphthyl, 4-fluoronaphthyl or 4-chloronaphthyl and in particular is 2,4-dimethoxyphenyl. Preference is likewise given to compounds of the general formula (I), their salts, their prodrugs and their N-oxides in which A is pyridin-2-yl or 3-methylpyridin-2-yl, and B is as defined herein.

Preference is further given to compounds of the general formula (I), their salts, their prodrugs and their N-oxides in which A is a pyridine radical, in particular is 3-pyridyl which is unsubstituted or has a substituent $R^A$ which is linked in position 2, or is 3-pyridyl which has a first radical $R^A$ which is linked in position 2 and a further radical $R^A$ which is linked in position 4, 5 or 6 and specifically in position 5, such as, for example, 2-methoxypyridin-3-yl, 2-ethoxypyridin-3-yl, 2-ethoxy-5-methylpyridin-3-yl, 2-ethoxy-5-ethylpyridin-3-yl, 2-ethoxy-5-isopropylpyridin-3-yl, 2-ethoxy-5-cyclopropylpyridin-3-yl, 2-ethoxy-6-methoxypyridin-3-yl, 2-ethoxy-6-dimethyl-aminopyridin-3-yl, 6-chloro-2-methoxypyridin-3-yl, 6-chloro-2-ethoxypyridin-3-yl or 2,6-difluoropyridin-3-yl and specifically is 6-chloro-2-ethoxypyridin-3-yl, and B is pyridin-2-yl or quinolin-8-yl, which are in each case unsubstituted or have one or two substituents $R^B$, in particular is pyridin-2-yl or quinolin-8-yl, which are in each case unsubstituted or has a substituent $R^B$ in position 5, such as, for example, pyridin-2-yl, 5-methylpyridin-2-yl, 5-methoxypyridin-2-yl, quinolin-8-yl, 3-methylquinolin-8-yl, 4-methylquinolin-8-yl, 5-methylquinolin-8-yl, 5-methoxyquinolin-8-yl, 4-ethyl-8-quinolinyl, 5-ethoxyquinolin-8-yl, 5-chloroquinolin-8-yl, or 5-fluoroquinolin-8-yl. Preference is likewise given to compounds of the general formula (I), their salts, their prodrugs and their N-oxides in which A is pyridin-2-yl or 3-methylpyridin-2-yl and B is as defined herein.

Preference is further given to compounds of the general formula (I), their salts, their prodrugs and their N-oxides in which A is a phenyl radical which has a substituent $R^A$ which is linked in position 2 or is a phenyl radical which has a first radical $R^A$ which is linked in position 2, and a further radical $R^A$ which is linked in position 3, 4 or 5 and specifically in position 5, such as, for example, 2-methoxyphenyl, 2-ethoxyphenyl, 2,5-dimethoxyphenyl, 2-ethoxy-5-ethyl-phenyl or 2-ethoxy-5-methoxyphenyl, and Y is one of the groups Y.1 to Y.7 defined above.

Preference is further given to compounds of the general formula (I), their salts, their prodrugs and their N-oxides, in which A is a pyridine radical, in particular is 3-pyridyl which is unsubstituted or has a substituent $R^A$ which is linked in position 2, or is 3-pyridyl which has a first radical $R^A$ which is linked in position 2, and a further radical $R^A$ which is linked in position 4, 5 or 6 and specifically in position 5, such as, for example, 2-methoxypyridin-3-yl, 2-ethoxypyridin-3-yl, 2-ethoxy-5-methylpyridin-3-yl, 2-ethoxy-5-ethylpyridin-3-yl, 2-ethoxy-5-isopropylpyridin-3-yl, 2-ethoxy-5-cyclopropylpyridin-3-yl, 2-ethoxy-6-methoxypyridin-3-yl, 2-ethoxy-6-dimethyl-aminopyridin-3-yl, 6-chloro-2-methoxypyridin-3-yl, 6-chloro-2-ethoxypyridin-3-yl or 2,6-difluoropyridin-3-yl and specifically is 6-chloro-2-ethoxypyridin-3-yl, and Y is one of the groups Y.1 to Y.7 defined above. Preference is likewise given to compounds of the general formula (I), their salts, their prodrugs and their N-oxides in which A is pyridin-2-yl or 3-methylpyridin-2-yl, and Y is one of the groups Y.1 to Y.7 defined herein.

Preference is further given to compounds of the general formula (I), their salts, their prodrugs and their N-oxides, in which A is a phenyl radical which has a substituent $R^A$ which is linked in position 2, or is a phenyl radical which has a first radical $R^A$ which is linked in position 2, and a further radical $R^A$ which is linked in position 3, 4 or 5 and specifically in position 5, such as, for example 2-methoxyphenyl, 2-ethoxyphenyl, 2,5-dimethoxyphenyl, 2-ethoxy-5-ethyl-phenyl or 2-ethoxy-5-methoxyphenyl, and Het is pyridin-4-yl, pyridin-3-yl, pyridin-2-yl, 2-methyl-pyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl. In this embodiment, preference is further given to compounds of the general formula (I), their salts, their prodrugs and their N-oxides, in which Het is 2-ethyl-pyridin-4-yl or 2-isopropyl-pyridin-4-yl and A is as defined herein.

Preference is further given to compounds of the general formula (I), their salts, their prodrugs and their N-oxides, in which A is a pyridine radical, in particular is 3-pyridyl which is unsubstituted or has a substituent $R^A$ which is linked in position 2, or is 3-pyridyl which has a first radical $R^A$ which is linked in position 2, and a further radical $R^A$ which is linked in position 4, 5 or 6 and specifically in position 5, such as, for example, 2-methoxypyridin-3-yl, 2-ethoxypyridin-3-yl, 2-ethoxy-5-methylpyridin-3-yl, 2-ethoxy-5-ethylpyridin-3-yl, 2-ethoxy-5-isopropylpyridin-3-yl, 2-ethoxy-5-cyclopropylpyridin-3-yl, 2-ethoxy-6-methoxypyridin-3-yl, 2-ethoxy-6-dimethyl-aminopyridin-3-yl, 6-chloro-2-methoxypyridin-3-yl, 6-chloro-2-ethoxypyridin-3-yl or 2,6-difluoropyridin-3-yl and specifically is 6-chloro-2-ethoxy-pyridin-3-yl and Het is pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl. In this embodiment, preference is further given to compounds of the general formula (I), their salts, their prodrugs and their N-oxides, in which Het is 2-ethyl-pyridin-4-yl or 2-isopropyl-pyridin-4-yl and A is as defined herein. Preference is likewise given to compounds of the general formula (I), their salts, their prodrugs and their N-oxides in which A is pyridin-2-yl or 3-methylpyridin-2-yl, and Het is as defined herein.

Preference is further given to compounds of the general formula (I), their salts, their prodrugs and their N-oxides in which B is pyridin-2-yl or quinolin-8-yl, each of which are unsubstituted or have one or two substituents $R^B$, in particular are pyridin-2-yl or quinolin-8-yl, each of which are unsubstituted or has a substituent $R^B$ in position 5, such as, for example, pyridin-2-yl, 5-methylpyridin-2-yl, 5-methoxypyridin-2-yl, quinolin-8-yl, 3-methylquinolin-8-yl, 4-methylquinolin-8-yl, 5-methylquinolin-8-yl, 5-methoxyquinolin-8-yl, 4-ethyl-8-quinolinyl, 5-ethoxyquinolin-8-yl, 5-chloroquinolin-8-yl, or 5-fluoro-quinolin-8-yl, and Y is one of the groups Y.1 to Y.7 defined above.

Preference is further given to compounds of the general formula (I), their salts, their prodrugs and their N-oxides, in which B is phenyl or naphthyl, each of which have one or two substituents $R^B$, such as, for example, 2,3-dimethoxyphenyl, 2,4-dimethoxyphenyl, 3,5-dimethoxyphenyl, 2-ethoxy-4-methoxyphenyl, 4-amino-2-methoxyphenyl, 4-methoxy-2- nitrophenyl, 4-methoxynaphthyl, 2-trifluoromethyl-4-cyanophenyl, 8-methoxynaphthyl, 4,8-dimethoxynaphthyl, 4-fluoronaphthyl or 4-chloronaphthyl and specifically is 2,4-dimethoxyphenyl, and Y is one of the groups Y.1 to Y.7 defined above.

Preference is further given to compounds of the general formula (I), their salts, their prodrugs and their N-oxides, in which B is pyridin-2-yl or quinolin-8-yl, each of which are unsubstituted or have one or two substituents $R^B$, in particular are pyridin-2-yl or quinolin-8-yl, each of which are unsubstituted or has a substituent $R^B$ in position 5, such as, for example, pyridin-2-yl, 5-methylpyridin-2-yl, 5-methoxypyridin-2-yl, quinolin-8-yl, 3-methylquinolin-8-yl, 4-methylquinolin-8-yl, 5-methylquinolin-8-yl, 5-methoxyquinolin-8-yl, 4-ethyl-8-quinolinyl, 5-ethoxyquinolin-8-yl, 5-chloroquinolin-8-yl, or 5-fluoro-quinolin-8-yl, and Het is pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl.

Preference is further given to compounds of the general formula (I), their salts, their prodrugs and their N-oxides, in which B is phenyl or naphthyl, each of which have one or two substituents $R^B$, such as, for example, 2,3-dimethoxyphenyl, 2,4-dimethoxyphenyl, 3,5-dimethoxyphenyl, 2-ethoxy-4-methoxyphenyl, 4-amino-2-methoxyphenyl, 4-methoxy-2-nitrophenyl, 4-methoxynaphthyl, 2-trifluoromethyl-4-cyanophenyl, 8-methoxynaphthyl, 4,8-dimethoxynaphthyl, 4-fluoronaphthyl or 4-chloronaphthyl and specifically is 2,4-dimethoxyphenyl, and Het is pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl.

Preference is further given to compounds of the general formula (I), their salts, their prodrugs and their N-oxides, in which Y is one of the groups Y.1 to Y.7 defined above, and Het is pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl. Preference is further given to compounds of the general formula (I), their salts, their prodrugs and their N-oxides, in which Y is one of the groups Y.1 to Y.7 defined above, and Het is 2-ethyl-pyridin-4-yl or 2-isopropyl-pyridin-4-yl.

Particular preference is given to compounds of the general formula (I), their salts, their prodrugs and their N-oxides, in which A is a phenyl radical which has a substituent $R^A$ which is linked in position 2, or is a phenyl radical which has a first radical $R^A$ which is linked in position 2, and a further radical $R^A$ which is linked in position 3, 4 or 5 and specifically in position 5, such as, for example, 2-methoxyphenyl, 2-ethoxyphenyl, 2,5-dimethoxyphenyl, 2-ethoxy-5-ethylphenyl or 2-ethoxy-5-methoxyphenyl, B is pyridin-2-yl or quinolin-8-yl, each of which are unsubstituted or have one or two substituents $R^B$, in particular is pyridin-2-yl or quinolin-8-yl, each of which are unsubstituted or has a substituent $R^B$ in position 5, such as, for example, pyridin-2-yl, 5-methylpyridin-2-yl, 5-methoxypyridin-2-yl, quinolin-8-yl, 3-methylquinolin-8-yl, 4-methylquinolin-8-yl, 5-methylquinolin-8-yl, 5-methoxyquinolin-8-yl, 4-ethyl-8-quinolinyl, 5-ethoxyquinolin-8-yl, 5-chloroquinolin-8-yl, or 5-fluoroquinolin-8-yl, and Y is one of the groups Y.1 to Y.7 defined above.

Particular preference is further given to compounds of the general formula (I), their salts, their prodrugs and their N-oxides, in which A is a pyridine radical, in particular is 3-pyridyl which is unsubstituted or has a substituent $R^A$ which is linked in position 2, or is 3-pyridyl which has a first radical $R^A$ which is linked in position 2, and a further radical $R^A$ which is linked in position 4, 5 or 6 and specifically in position 5, such as, for example, 2-methoxypyridin-3-yl, 2-ethoxypyridin-3-yl, 2-ethoxy-5-methylpyridin-3-yl, 2-ethoxy-5-ethylpyridin-3-yl, 2-ethoxy-5-isopropylpyridin-3-yl, 2-ethoxy-5-cyclopropylpyridin-3-yl, 2-ethoxy-6-methoxypyridin-3-yl, 2-ethoxy-6-dimethyl-aminopyridin-3-yl, 6-chloro-2-methoxypyridin-3-yl, 6-chloro-2-ethoxypyridin-3-yl or 2,6-difluoropyridin-3-yl and specifically is 6-chloro-2-ethoxypyridin-3-yl, B is pyridin-2-yl or quinolin-8-yl, each of which are unsubstituted or have one or two substituents $R^B$, in particular is pyridin-2-yl or quinolin-8-yl, each of which are unsubstituted or has a substituent $R^B$ in position 5, such as, for example, pyridin-2-yl, 5-methylpyridin-2-yl, 5-methoxypyridin-2-yl, quinolin-8-yl, 3-methylquinolin-8-yl, 4-methylquinolin-8-yl, 5-methylquinolin-8-yl, 5-methoxyquinolin-8-yl, 4-ethyl-8-quinolinyl, 5-ethoxyquinolin-8-yl, 5-chloroquinolin-8-yl, or 5-fluoroquinolin-8-yl, and Y is one of the groups Y.1 to Y.7 defined above. Preference is likewise given to compounds of the general formula (I), their salts, their prodrugs and their N-oxides, in which A is pyridin-2-yl or 3-methylpyridin-2-yl, and B and Y are as defined herein.

Particular preference is further given to compounds of the general formula (I), their salts, their prodrugs and their N-oxides, in which A is a pyridine radical, in particular is 3-pyridyl which is unsubstituted or has a substituent $R^A$ which is linked in position 2, or is 3-pyridyl which has a first radical $R^A$ which is linked in position 2, and a further radical $R^A$ which is linked in position 4, 5 or 6 and specifically in position 5, such as, for example, 2-methoxypyridin-3-yl, 2-ethoxypyridin-3-yl, 2-ethoxy-5-methylpyridin-3-yl, 2-ethoxy-5-ethylpyridin-3-yl, 2-ethoxy-5-isopropylpyridin-3-yl, 2-ethoxy-5-cyclopropylpyridin-3-yl, 2-ethoxy-6-methoxypyridin-3-yl, 2-ethoxy-6-dimethyl-aminopyridin-3-yl, 6-chloro-2-methoxypyridin-3-yl, 6-chloro-2-ethoxypyridin-3-yl or 2,6-difluoropyridin-3-yl and specifically is 6-chloro-2-ethoxypyridin-3-yl, B is pyridin-2-yl or quinolin-8-yl, each of which are unsubstituted or have one or two substituents $R^B$, in particular is pyridin-2-yl or quinolin-8-yl, each of which are unsubstituted or has a substituent $R^B$ in position 5, such as, for example, pyridin-2-yl, 5-methylpyridin-2-yl, 5-methoxypyridin-2-yl, quinolin-8-yl, 3-methylquinolin-8-yl, 4-methylquinolin-8-yl, 5-methylquinolin-8-yl, 5-methoxyquinolin-8-yl, 4-ethyl-8-quinolinyl, 5-ethoxyquinolin-8-yl, 5-chloroquinolin-8-yl, or 5-fluoroquinolin-8-yl, and Y is one of the groups Y.1 to Y.7 defined above. Preference is likewise given to compounds of the general formula (I), their salts, their prodrugs and their N-oxides, in which A is pyridin-2-yl or 3-methylpyridin-2-yl, and B and Y are as defined herein.

Particular preference is further given to compounds of the general formula (I), their salts, their prodrugs and their N-oxides, in which A is a phenyl radical which has a substituent $R^A$ which is linked in position 2, or is a phenyl radical which has a first radical $R^A$ which is linked in position 2, and a further radical $R^A$ which is linked in position 3, 4 or 5 and specifically in position 5, such as, for example, 2-methoxyphenyl, 2-ethoxyphenyl, 2,5-dimethoxyphenyl, 2-ethoxy-5-ethylphenyl or 2-ethoxy-5-methoxyphenyl, B is pyridin-2-yl or quinolin-8-yl, each of which are unsubstituted or have one or two substituents $R^B$, in particular is pyridin-2-yl or quinolin-8-yl, each of which are unsubstituted or has a substituent $R^B$ in position 5, such as, for example, pyridin-2-yl, 5-methylpyridin-2-yl, 5-methoxypyridin-2-yl, quinolin-8-yl, 3-methylquinolin-8-yl, 4-methylquinolin-8-yl, 5-methylquinolin-8-yl, 5-methoxyquinolin-8-yl, 4-ethyl-8-quinolinyl, 5-ethoxyquinolin-8-yl, 5-chloroquinolin-8-yl, or 5-fluoroquinolin-8-yl, and Het is pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl. In this embodiment, preference is further given to compounds of the general formula (I), their salts, their prodrugs and their N-oxides, in which Het is 2-ethyl-pyridin-4-yl or 2-isopropyl-pyridin-4-yl and A and B are as defined herein.

Particular preference is further given to compounds of the general formula (I), their salts, their prodrugs and their N-oxides, in which A pyridine radical, in particular is 3-pyridyl which is unsubstituted or has a substituent $R^A$ which is linked in position 2, or is 3-pyridyl which has a first radical $R^A$ which is linked in position 2, and a further radical $R^A$ which is linked in position 4, 5 or 6 and specifically in position 5, such as, for example, 2-methoxypyridin-3-yl, 2-ethoxypyridin-3-yl, 2-ethoxy-5-methylpyridin-3-yl, 2-ethoxy-5-ethylpyridin-3-yl, 2-ethoxy-5-isopropylpyridin-3-yl, 2-ethoxy-5-cyclopropylpyridin-3-yl, 2-ethoxy-6-methoxypyridin-3-yl, 2-ethoxy-6-dimethyl-aminopyridin-3-yl, 6-chloro-2-methoxypyridin-3-yl, 6-chloro-2-ethoxypyridin-3-yl or 2,6-difluoropyridin-3-yl and specifically is 6-chloro-2-ethoxypyridin-3-yl, B is phenyl or naphthyl, each of which has one or two substituents $R^B$, such as, for example, 2,3-dimethoxyphenyl, 2,4-dimethoxyphenyl, 3,5-dimethoxyphenyl, 2-ethoxy-4-methoxyphenyl, 4-amino-2-methoxyphenyl, 4-methoxy-2-nitrophenyl, 4-methoxynaphthyl, 2-trifluoromethyl-4-cyanophenyl, 8-methoxynaphthyl, 4,8-dimethoxynaphthyl, 4-fluoronaphthyl or 4-chloronaphthyl and in particular is 2,4-dimethoxyphenyl, and Het is pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl. In this embodiment, preference is also given to compounds of the general formula (I), their salts, their prodrugs and their N-oxides, in which Het is 2-ethylpyridin-4-yl or 2-isopropyl-pyridin-4-yl and A and B are as defined herein. Preference is likewise given to compounds of the general formula (I), their salts, their prodrugs and their N-oxides, in which A is pyridin-2-yl or 3-methylpyridin-2-yl, and B and Het are as defined herein.

Particular preference is further given to compounds of the general formula (I), their salts, their prodrugs and their N-oxides, in which A is a pyridine radical, in particular is 3-pyridyl which is unsubstituted or has a substituent $R^A$ which is linked in position 2, or is 3-pyridyl which has a first radical $R^A$ which is linked in position 2, and a further radical $R^A$ which is linked in position 4, 5 or 6 and specifically in position 5, such as, for example, 2-methoxypyridin-3-yl, 2-ethoxypyridin-3-yl, 2-ethoxy-5-methylpyridin-3-yl, 2-ethoxy-5-ethylpyridin-3-yl, 2-ethoxy-5-isopropylpyridin-3-yl, 2-ethoxy-5-cyclopropylpyridin-3-yl, 2-ethoxy-6-methoxypyridin-3-yl, 2-ethoxy-6-dimethyl-aminopyridin-3-yl, 6-chloro-2-methoxypyridin-3-yl, 6-chloro-2-ethoxypyridin-3-yl or 2,6-difluoropyridin-3-yl and specifically is 6-chloro-2-ethoxypyridin-3-yl, B is phenyl or quinolin-8-yl, each of which are unsubstituted or have one or two substituents $R^B$, in particular is pyridin-2-yl or quinolin-8-yl, each of which are unsubstituted or has a substituent $R^B$ in position 5, such as, for example, pyridin-2-yl, 5-methylpyridin-2-yl, 5-methoxypyridin-2-yl, quinolin-8-yl, 3-methylquinolin-8-yl, 4-methylquinolin-8-yl, 5-methylquinolin-8-yl, 5-methoxyquinolin-8-yl, 4-ethyl-8-quinolinyl, 5-ethoxyquinolin-8-yl, 5-chloroquinolin-8-yl, or 5-fluoroquinolin-8-yl, and Het is pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl. In this embodiment, preference is also given to compounds of the general formula (I), their salts, their prodrugs and their N-oxides, in which Het is 2-ethylpyridin-4-yl or 2-isopropyl-pyridin-4-yl and A and B are as defined herein. Likewise, preference is given to compounds of the general formula (I), their salts, their prodrugs and their N-oxides, in which A is pyridin-2-yl or 3-methylpyridin-2-yl, and B and Het are as defined herein.

Particular preference is further given to compounds of the general formula (I), their salts, their prodrugs and their N-oxides, in which A is a phenyl radical which has a substituent $R^A$ which is linked in position 2, or is a phenyl radical which has a first radical $R^A$ which is linked in position 2, and a further radical $R^A$ which is linked in position 3, 4 or 5 and specifically in position 5, such as, for example, 2-methoxyphenyl, 2-ethoxyphenyl, 2,5-dimethoxyphenyl, 2-ethoxy-5-ethylphenyl or 2-ethoxy-5-methoxyphenyl, Y is one of the groups Y.1 to Y.7 defined above, and Het is pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl. In this embodiment, preference is also given to compounds of the general formula (I), their salts, their prodrugs and their N-oxides, in which Het is 2-ethylpyridin-4-yl or 2-isopropyl-pyridin-4-yl and A and Y are as defined herein Particular preference is further given to compounds of the general formula (I), their salts, their prodrugs and their N-oxides, in which A is a pyridine radical, in particular is 3-pyridyl which is unsubstituted or has a substituent $R^A$ which is linked in position 2, or is 3-pyridyl which has a first radical $R^A$ which is linked in position 2, and a further radical $R^A$ which is linked in position 4, 5 or 6 and specifically in position 5, such as, for example, 2-methoxypyridin-3-yl, 2-ethoxypyridin-3-yl, 2-ethoxy-5-methylpyridin-3-yl, 2-ethoxy-5-ethylpyridin-3-yl, 2-ethoxy-5-isopropylpyridin-3-yl, 2-ethoxy-5-cyclopropylpyridin-3-yl, 2-ethoxy-6-methoxypyridin-3-yl, 2-ethoxy-6-dimethyl-aminopyridin-3-yl, 6-chloro-2-methoxypyridin-3-yl, 6-chloro-2-ethoxypyridin-3-yl or 2,6-difluoropyridin-3-yl and specifically is 6-chloro-2-ethoxypyridin-3-yl, Y is one of the groups Y.1 to Y.7 defined above, and Het is pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl. In this embodiment, preference is also given to compounds of the general formula (I), their salts, their prodrugs and their N-oxides, in which Het is 2-ethylpyridin-4-yl or 2-isopropyl-pyridin-4-yl and A and Y are as defined herein. Likewise, preference is given to compounds of the general formula (I), their salts, their prodrugs and their N-oxides, in which A is pyridin-2-yl or 3-methylpyridin-2-yl, Y is one of the groups Y.1 to Y.7 defined herein, and Het is as defined herein.

Particular preference is further given to compounds of the general formula (I), their salts, their prodrugs and their N-oxides, in which B is pyridin-2-yl or quinolin-8-yl, each of which are unsubstituted or have one or two substituents $R^B$, in particular is pyridin-2-yl or quinolin-8-yl, each of which are unsubstituted or has a substituent $R^B$ in position 5, such as, for example, pyridin-2-yl, 5-methylpyridin-2-yl, 5-methoxypyridin-2-yl, quinolin-8-yl, 3-methylquinolin-8-yl, 4-methylquinolin-8-yl, 5-methylquinolin-8-yl, 5-methoxy-quinolin-8-yl, 4-ethyl-8-quinolinyl, 5-ethoxyquinolin-8-yl, 5-chloroquinolin-8-yl, or 5-fluoroquinolin-8-yl, Y is one of the groups Y.1 to Y.7 defined above, and Het is pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl. In this embodiment, preference is also given to compounds of the general formula (I), their salts, their prodrugs and their N-oxides, in which Het is 2-ethylpyridin-4-yl or 2-isopropyl-pyridin-4-yl and B and Y are as defined herein.

Particular preference is further given to compounds of the general formula (I), their salts, their prodrugs and their N-oxides, in which B is phenyl or naphthyl, each of which has one or two substituents $R^B$, such as, for example, 2,3-dimethoxyphenyl, 2,4-dimethoxyphenyl, 3,5-dimethoxyphenyl, 2-ethoxy-4-methoxyphenyl, 4-amino-2-methoxyphenyl, 4-methoxy-2-nitrophenyl, 4-methoxynaphthyl, 2-trifluoromethyl-4-cyanophenyl, 8-methoxynaphthyl, 4,8-dimethoxynaphthyl, 4-fluoronaphthyl or 4-chloronaphthyl, Y is one of the groups Y.1 to Y.7 defined above, and Het is pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl. In this embodiment, preference is also given to compounds of the general formula (I), their salts, their prodrugs and their N-oxides, in which Het is 2-ethylpyridin-4-yl or 2-isopropyl-pyridin-4-yl and Y and B are as defined herein.

Very particular preference is given to compounds of the general formula (I), their salts, their prodrugs and their N-oxides, in which A is a phenyl radical which has a substituent $R^A$ which is linked in position 2, or is a phenyl radical which has a first radical $R^A$ which is linked in position 2, and a further radical $R^A$ which is linked in position 3, 4 or 5 and specifically in position 5, such as, for example, 2-methoxyphenyl, 2-ethoxyphenyl, 2,5-dimethoxyphenyl, 2-ethoxy-5-ethylphenyl or 2-ethoxy-5-methoxyphenyl, B is pyridin-2-yl or quinolin-8-yl, each of which are unsubstituted or have one or two substituents $R^B$, in particular is pyridin-2-yl or quinolin-8-yl, each of which are unsubstituted or has a substituent $R^B$ in position 5, such as, for example, pyridin-2-yl, 5-methylpyridin-2-yl, 5-methoxypyridin-2-yl, quinolin-8-yl, 3-methylquinolin-8-yl, 4-methylquinolin-8-yl, 4-methylquinolin-8-yl, 5-methylquinolin-8-yl, 5-methoxyquinolin-8-yl, 4-ethylquinolin-8-yl, 5-ethoxyquinolin-8-yl, 5-chloroquinolin-8-yl, or 5-fluoroquinolin-8-yl, Y is one of the groups Y.1 to Y.7 defined above, and Het is pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl. In this embodiment, preference is also given to compounds of the general formula (I), their salts, their prodrugs and their N-oxides, in which Het is 2-ethylpyridin-4-yl or 2-isopropyl-pyridin-4-yl and A, Y and B are as defined herein.

Very particular preference is further given to compounds of the general formula (I), their salts, their prodrugs and their N-oxides, in which A is a pyridine radical, in particular is 3-pyridyl which is unsubstituted or has a substituent $R^A$ which is linked in position 2, or is 3-pyridyl which has a first radical $R^A$ which is linked in position 2, and a further radical $R^A$ which is linked in position 4, 5 or 6 and specifically in position 5, such as, for example, 2-methoxypyridin-3-yl, 2-ethoxypyridin-3-yl, 2-ethoxy-5-methylpyridin-3-yl, 2-ethoxy-5-ethylpyridin-3-yl, 2-ethoxy-5-isopropylpyridin-3-yl, 2-ethoxy-5-cyclopropylpyridin-3-yl, 2-ethoxy-6-methoxypyridin-3-yl, 2-ethoxy-6-dimethyl-aminopyridin-3-yl, 6-chloro-2-methoxypyridin-3-yl, 6-chloro-2-ethoxypyridin-3-yl or 2,6-difluoropyridin-3-yl and specifically is 6-chloro-2-ethoxypyridin-3-yl, B is phenyl or naphthyl, each of which has one or two substituents $R^B$, such as, for example, 2,3-dimethoxyphenyl, 2,4-dimethoxyphenyl, 3,5-dimethoxyphenyl, 2-ethoxy-4-methoxyphenyl, 4-amino-2-methoxyphenyl, 4-methoxy-2-nitrophenyl, 4-methoxynaphthyl, 2-trifluoromethyl-4-cyanophenyl, 8-methoxynaphthyl, 4,8-dimethoxynaphthyl, 4-fluoronaphthyl or 4-chloronaphthyl and specifically is 2,4-dimethoxyphenyl, Y is one of the groups Y.1 to Y.7 defined above, and Het is pyridin-4-yl, pyridin-3-yl, pyridin-2-yl, 2-methyl-pyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl. In this embodiment, preference is also given to compounds of the general formula (I), their salts, their prodrugs and their N-oxides, in which Het is 2-ethylpyridin-4-yl or 2-isopropyl-pyridin-4-yl and A, B, and Y are as defined herein. Preference is likewise given to compounds of the general formula (I), their salts, their prodrugs and their N-oxides, in which A is pyridin-2-yl or 3-methylpyridin-2-yl, and B, Y and Het are as defined herein.

Very particular preference is further given to compounds of the general formula (I), their salts, their prodrugs and their N-oxides, in which A is a pyridine radical, in particular is 3-pyridyl which is unsubstituted or has a substituent $R^A$ which is linked in position 2, or is 3-pyridyl which has a first radical $R^A$ which is linked in position 2, and a further radical $R^A$ which is linked in position 4, 5 or 6 and specifically in position 5, such as, for example, 2-methoxypyridin-3-yl, 2-ethoxypyridin-3-yl, 2-ethoxy-5-methylpyridin-3-yl, 2-ethoxy-5-ethylpyridin-3-yl, 2-ethoxy-5-isopropylpyridin-3-yl, 2-ethoxy-5-cyclopropylpyridin-3-yl, 2-ethoxy-6-methoxypyridin-3-yl, 2-ethoxy-6-dimethyl-aminopyridin-3-yl, 6-chloro-2-methoxypyridin-3-yl, 6-chloro-2-ethoxypyridin-3-yl or 2,6-difluoropyridin-3-yl and specifically is 6-chloro-2-ethoxypyridin-3-yl, B is pyridin-2-yl or quinolin-8-yl, each of which are unsubstituted or have one or two substituents $R^B$, in particular is pyridin-2-yl or quinolin-8-yl, each of which are unsubstituted or has a substituent $R^B$ in position 5, such as, for example, pyridin-2-yl, 5-methylpyridin-2-yl, 5-methoxypyridin-2-yl, quinolin-8-yl, 3-methylquinolin-8-yl, 4-methylquinolin-8-yl, 5-methylquinolin-8-yl, 5-methoxyquinolin-8-yl, 4-ethyl-8-quinolinyl, 5-ethoxyquinolin-8-yl, 5-chloroquinolin-8-yl, or 5-fluoroquinolin-8-yl, Y is one of the groups Y.1 to Y.7 defined above, and Het is pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 3-methylpyridin-4-yl, 3-fluoropyridin-4-yl, 5-cyanopyridin-4-yl, 1,3-pyrimidin-4-yl, 1,3,5-triazin-2-yl or 1,3-thiazol-2-yl. In this embodiment, preference is also given to compounds of the general formula (I), their salts, their prodrugs and their N-oxides, in which Het is 2-ethylpyridin-4-yl or 2-isopropyl-pyridin-4-yl and A, B and Y are as defined herein. Preference is likewise given to compounds of the general formula (I), their salts, their prodrugs and their N-oxides, in which A is pyridin-2-yl or 3-methylpyridin-2-yl, and B is as defined herein, Y is as defined herein, and Het is as defined herein.

Preferred examples of compounds of the invention of the formula I are the compounds of the formulae I.A to I.K shown below in Tables 1 to 10.

TABLE 1

Compounds of the formula (I) in which A is 6-chloro-2-ethoxypyridin-3-yl and B is 2,4-dimethoxyphenyl (compounds of the formula I.A). The meaning of Y and Het in the compounds I.A.1 to I.A.105 is in each case that given in lines 1 to 105 of Table A.

(I.A)

TABLE A

| Line | Y | Het |
|---|---|---|
| 1 | Y.1 | pyridin-4-yl |
| 2 | Y.1 | 2-methylpyridin-4-yl |
| 3 | Y.1 | 2-ethylpyridin-4-yl |
| 4 | Y.1 | 2-isopropylpyridin-4-yl |
| 5 | Y.1 | 2-cyclopropylpyridin-4-yl |
| 6 | Y.1 | piperazin-1-yl |
| 7 | Y.1 | 4-methylpiperazin-1-yl |
| 8 | Y.1 | 4-ethylpiperazin-1-yl |
| 9 | Y.1 | 4-isopropylpiperazin-1-yl |
| 10 | Y.1 | 4-cyclopropylpiperazin-1-yl |
| 11 | Y.1 | piperidin-4-yl |
| 12 | Y.1 | 1-methylpiperidin-4-yl |
| 13 | Y.1 | 1-ethylpiperidin-4-yl |
| 14 | Y.1 | 1-isopropylpiperidin-4-yl |
| 15 | Y.1 | 1-cyclopropylpiperidin-4-yl |
| 16 | Y.2 | pyridin-4-yl |
| 17 | Y.2 | 2-methylpyridin-4-yl |
| 18 | Y.2 | 2-ethylpyridin-4-yl |
| 19 | Y.2 | 2-isopropylpyridin-4-yl |
| 20 | Y.2 | 2-cyclopropylpyridin-4-yl |
| 21 | Y.2 | piperazin-1-yl |
| 22 | Y.2 | 4-methylpiperazin-1-yl |
| 23 | Y.2 | 4-ethylpiperazin-1-yl |
| 24 | Y.2 | 4-isopropylpiperazin-1-yl |
| 25 | Y.2 | 4-cyclopropylpiperazin-1-yl |
| 26 | Y.2 | piperidin-4-yl |
| 27 | Y.2 | 1-methylpiperidin-4-yl |
| 28 | Y.2 | 1-ethylpiperidin-4-yl |
| 29 | Y.2 | 1-isopropylpiperidin-4-yl |
| 30 | Y.2 | 1-cyclopropylpiperidin-4-yl |
| 31 | Y.3 | pyridin-4-yl |
| 32 | Y.3 | 2-methylpyridin-4-yl |
| 33 | Y.3 | 2-ethylpyridin-4-yl |
| 34 | Y.3 | 2-isopropylpyridin-4-yl |
| 35 | Y.3 | 2-cyclopropylpyridin-4-yl |
| 36 | Y.3 | piperazin-1-yl |
| 37 | Y.3 | 4-methylpiperazin-1-yl |
| 38 | Y.3 | 4-ethylpiperazin-1-yl |
| 39 | Y.3 | 4-isopropylpiperazin-1-yl |
| 40 | Y.3 | 4-cyclopropylpiperazin-1-yl |
| 41 | Y.3 | piperidin-4-yl |
| 42 | Y.3 | 1-methylpiperidin-4-yl |
| 43 | Y.3 | 1-ethylpiperidin-4-yl |
| 44 | Y.3 | 1-isopropylpiperidin-4-yl |
| 45 | Y.3 | 1-cyclopropylpiperidin-4-yl |
| 46 | Y.4 | pyridin-4-yl |
| 47 | Y.4 | 2-methylpyridin-4-yl |
| 48 | Y.4 | 2-ethylpyridin-4-yl |
| 49 | Y.4 | 2-isopropylpyridin-4-yl |
| 50 | Y.4 | 2-cyclopropylpyridin-4-yl |
| 51 | Y.4 | piperazin-1-yl |
| 52 | Y.4 | 4-methylpiperazin-1-yl |
| 53 | Y.4 | 4-ethylpiperazin-1-yl |
| 54 | Y.4 | 4-isopropylpiperazin-1-yl |
| 55 | Y.4 | 4-cyclopropylpiperazin-1-yl |
| 56 | Y.4 | piperidin-4-yl |
| 57 | Y.4 | 1-methylpiperidin-4-yl |
| 58 | Y.4 | 1-ethylpiperidin-4-yl |
| 59 | Y.4 | 1-isopropylpiperidin-4-yl |
| 60 | Y.4 | 1-cyclopropylpiperidin-4-yl |
| 61 | Y.5 | pyridin-4-yl |
| 62 | Y.5 | 2-methylpyridin-4-yl |
| 63 | Y.5 | 2-ethylpyridin-4-yl |
| 64 | Y.5 | 2-isopropylpyridin-4-yl |
| 65 | Y.5 | 2-cyclopropylpyridin-4-yl |
| 66 | Y.5 | piperazin-1-yl |
| 67 | Y.5 | 4-methylpiperazin-1-yl |
| 68 | Y.5 | 4-ethylpiperazin-1-yl |
| 69 | Y.5 | 4-isopropylpiperazin-1-yl |
| 70 | Y.5 | 4-cyclopropylpiperazin-1-yl |
| 71 | Y.5 | piperidin-4-yl |
| 72 | Y.5 | 1-methylpiperidin-4-yl |
| 73 | Y.5 | 1-ethylpiperidin-4-yl |
| 74 | Y.5 | 1-isopropylpiperidin-4-yl |
| 75 | Y.5 | 1-cyclopropylpiperidin-4-yl |
| 76 | Y.6 | pyridin-4-yl |
| 77 | Y.6 | 2-methylpyridin-4-yl |
| 78 | Y.6 | 2-ethylpyridin-4-yl |
| 79 | Y.6 | 2-isopropylpyridin-4-yl |
| 80 | Y.6 | 2-cyclopropylpyridin-4-yl |
| 81 | Y.6 | piperazin-1-yl |
| 82 | Y.6 | 4-methylpiperazin-1-yl |
| 83 | Y.6 | 4-ethylpiperazin-1-yl |
| 84 | Y.6 | 4-isopropylpiperazin-1-yl |
| 85 | Y.6 | 4-cyclopropylpiperazin-1-yl |
| 86 | Y.6 | piperidin-4-yl |
| 87 | Y.6 | 1-methylpiperidin-4-yl |
| 88 | Y.6 | 1-ethylpiperidin-4-yl |
| 89 | Y.6 | 1-isopropylpiperidin-4-yl |
| 90 | Y.6 | 1-cyclopropylpiperidin-4-yl |
| 91 | Y.7 | pyridin-4-yl |
| 92 | Y.7 | 2-methylpyridin-4-yl |
| 93 | Y.7 | 2-ethylpyridin-4-yl |
| 94 | Y.7 | 2-isopropylpyridin-4-yl |
| 95 | Y.7 | 2-cyclopropylpyridin-4-yl |
| 96 | Y.7 | piperazin-1-yl |
| 97 | Y.7 | 4-methylpiperazin-1-yl |
| 98 | Y.7 | 4-ethylpiperazin-1-yl |
| 99 | Y.7 | 4-isopropylpiperazin-1-yl |
| 100 | Y.7 | 4-cyclopropylpiperazin-1-yl |
| 101 | Y.7 | piperidin-4-yl |
| 102 | Y.7 | 1-methylpiperidin-4-yl |
| 103 | Y.7 | 1-ethylpiperidin-4-yl |
| 104 | Y.7 | 1-isopropylpiperidin-4-yl |
| 105 | Y.7 | 1-cyclopropylpiperidin-4-yl |

TABLE 2

Compounds of the formula (I) in which A is 2-ethoxyphenyl and B is 3-methoxypyridin-6-yl (compounds of the formula I.B). The meaning of Y and Het in the compounds I.B.1 to I.B.105 is in each case that given in lines 1 to 105 of Table A.

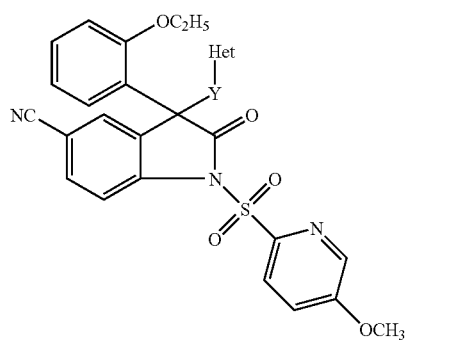
(I.B)

TABLE 3

Compounds of the formula (I) in which A is 2-ethoxy-5-methoxyphenyl and B is 3-methoxypyridin-6-yl (compounds of the formula I.C). The meaning of Y and Het in the compounds I.C.1 to I.C.105 is in each case that given in lines 1 to 105 of Table A.

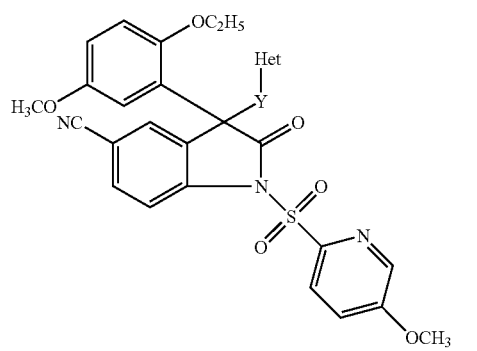
(I.C)

TABLE 4

Compounds of the formula (I) in which A is 6-chloro-2-ethoxypyridin-3-yl and B is 3-methoxypyridin-6-yl (compounds of the formula I.D). The meaning of Y and Het in the compounds I.D.1 to I.D.105 is in each case that given in lines 1 to 105 of Table A.

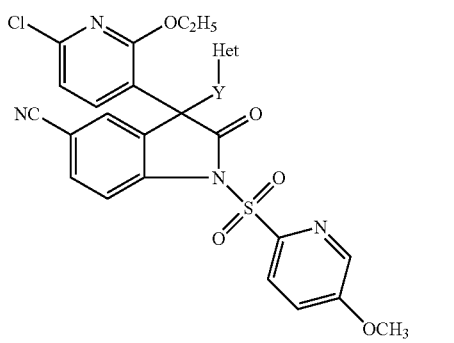
(I.D)

TABLE 5

Compounds of the formula (I) in which A is 2-ethoxyphenyl and B is quinolin-8-yl (compounds of the formula I.E). The meaning of Y and Het in the compounds I.E.1 to I.E.105 is in each case that given in lines 1 to 105 of Table A.

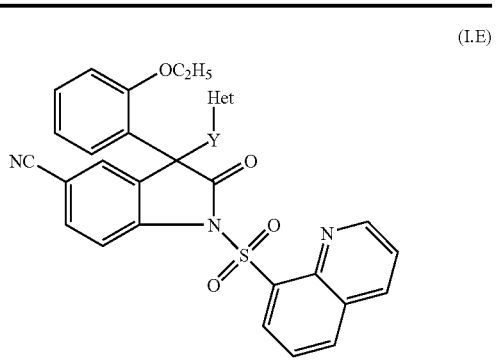
(I.E)

TABLE 6

Compounds of the formula (I) in which A is 2-ethoxy-5-methoxyphenyl and B is quinolin-8-yl (compounds of the formula I.F). The meaning of Y and Het in the compounds I.F.1 to I.F.105 is in each case that given in lines 1 to 105 of Table A.

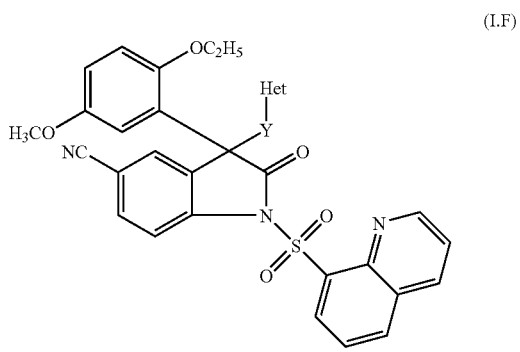
(I.F)

TABLE 7

Compounds of the formula (I) in which A is 6-chloro-2-ethoxypyridin-3-yl and B is quinolin-8-yl (compounds of the formula I.G). The meaning of Y and Het in the compounds I.G.1 to I.G.105 is in each case that given in lines 1 to 105 of Table A.

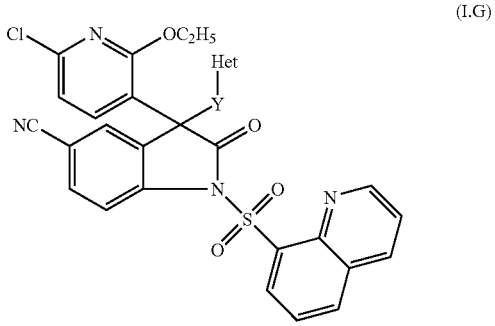
(I.G)

TABLE 8

Compounds of the formula (I) in which A is 2-ethoxyphenyl and
B is 5-methoxyquinolin-8-yl (compounds of the formula I.H).
The meaning of Y and Het in the compounds I.H.1 to I.H.105 is
in each case that given in lines 1 to 105 of Table A.

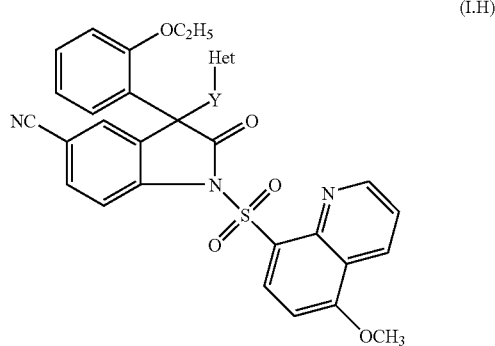

(I.H)

TABLE 9

Compounds of the formula (I) in which A is 2-ethoxy-5-methoxyphenyl and
B is 5-methoxyquinolin-8-yl (compounds of the formula I.I).
The meaning of Y and Het in the compounds I.I.1 to I.I.105 is
in each case that given in lines 1 to 105 of Table A.

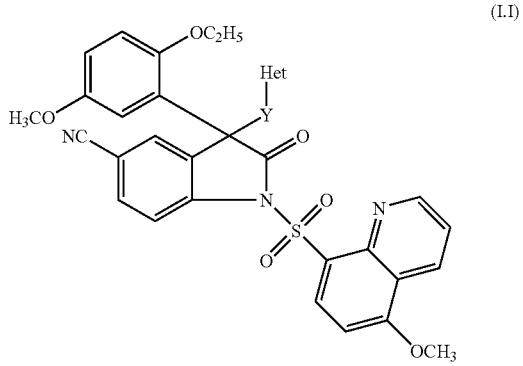

(I.I)

TABLE 10

Compounds of the formula (I) in which A is
6-chloro-2-ethoxypyridin-3-yl and
B is 5-methoxyquinolin-8-yl (compounds of the formula I.K).
The meaning of Y and Het in the compounds I.K.1 to I.K.105 is
in each case that given in lines 1 to 105 of Table A.

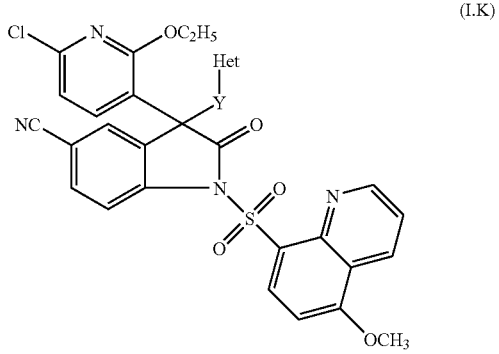

(I.K)

A further aspect of the present invention relates to the use of a compound of the general formula (I) its salts, its prodrugs or its N-oxides for the manufacture of a medicament for the treatment and/or for the prophylaxis of vasopressin-dependent and/or oxytocin-dependent disease.

A further aspect of the present invention relates to the use of a compound of the general formula (I), its salts, its prodrugs or its N-oxides for the manufacture of a medicament for the treatment and/or prophylaxis of disorders selected from diabetes, insulin resistance, nocturnal enuresis, incontinence, diseases in which blood coagulation disorders occur and/or for delaying micturition. The term "diabetes" refers to all forms of diabetes, especially diabetes mellitus (including type 1 and especially type 2), diabetes renalis and in particular diabetes insipidus. The forms of diabetes preferably include type 2 diabetes mellitus (non-insulin-dependent diabetes mellitus) or diabetes insipidus.

A further aspect of the present invention relates to the use of a compound of the general formula (I), its salts, its prodrugs or its N-oxides for the manufacture of a medicament for the treatment and/or prophylaxis of a disorder selected from hypertension, pulmonary hypertension, heart failure, myocardial infarction, coronary spasm, unstable angina, PTCA (percutaneous transluminal coronary angioplasty), ischemias of the heart, disorders of the renal system, edemas, renal vasospasm, necrosis of the renal cortex, hyponatremia, hypokalemia, Schwartz-Bartter syndrome, disorders of the gastrointestinal tract, gastritic vasospasm, hepatocirrhosis, gastric and intestinal ulcer, emesis, emesis occurring during chemotherapy and/or travel sickness.

A further aspect of the present invention relates to the use of a compound of the general formula (I), its salts, its prodrugs or its N-oxides for the manufacture of a medicament for the treatment of affective disorders.

A further aspect of the present invention relates to the use of a compound of the general formula (I), its salts, its prodrugs or its N-oxides for the manufacture of a medicament for the treatment of anxiety disorders and/or stress-dependent anxiety disorders.

A further aspect of the present invention relates to the use of a compound of the general formula (I), its salts, its prodrugs or its N-oxides for the manufacture of a medicament for the treatment of memory impairments and/or Alzheimer's disease.

A further aspect of the present invention relates to the use of a compound of the general formula (I), its salts, its prodrugs or its N-oxides for the manufacture of a medicament for the treatment of psychoses and/or psychotic disorders.

A further aspect of the present invention relates to the use of a compound of the general formula (I), its salts, its prodrugs or its N-oxides for the manufacture of a medicament for the treatment of Cushing's syndrome and stress-dependent diseases.

A further aspect of the present invention relates to the use of a compound of the general formula (I), its salts, its prodrugs or its N-oxides for the manufacture of a medicament for the treatment of sleep disorders.

A further aspect of the present invention relates to the use of a compound of the general formula (I), its salts, its prodrugs or its N-oxides for the manufacture of a medicament for the treatment of disorders selected from depressive disorders. A specific form of depressive disorders are childhood onset mood disorders, i.e. depressive moods starting in childhood.

A further aspect of the present invention relates to the use of a compound of the general formula (I), its salts, its prodrugs or its N-oxides for the manufacture of a medicament for the treatment and/or prophylaxis of vasomotor disorders and thermoregulatory dysfunctions.

A further aspect of the present invention relates to the use of a compound of the general formula (I), its salts, its prodrugs or its N-oxides for the manufacture of a medicament for the treatment and/or prophylaxis of addiction mediated by drugs, medicaments and/or other factors; of stress induced by withdrawal from one or more addiction-mediating factors; and/or of stress-induced relapse to addiction mediated by drugs, medicaments and/or other factors.

A further aspect of the present invention relates to the use of a compound of the general formula (I), its salts, its prodrugs or its N-oxides for the manufacture of a medicament for the treatment and/or prophylaxis of disorders selected from schizophrenia and psychoses.

A further aspect of the present invention relates to a method for the treatment and/or prophylaxis of a disorder selected from diabetes, insulin resistance, nocturnal enuresis, incontinence, diseases in which blood coagulation disorders occur, and for delaying micturition in a patient, which comprises administering to the patient an effective amount of a compound of the general formula (I), its salts, its prodrugs or its N-oxides. As regards the disorder diabetes, reference is made to the above-mentioned explanations.

A further aspect of the present invention relates to a method for the treatment and/or prophylaxis of a disorder selected from hypertension, pulmonary hypertension, heart failure, myocardial infarction, coronary spasm, unstable angina, PTCA (percutaneous transluminal coronary angioplasty), ischemias of the heart, disorders of the renal system, edemas, renal vasospasm, necrosis of the renal cortex, hyponatremia, hypokalemia, Schwartz-Bartter syndrome, disorders of the gastrointestinal tract, gastritic vasospasm, hepatocirrhosis, gastric and intestinal ulcer, emesis, emesis occurring during chemotherapy and/or travel sickness in a patient, which comprises administering to the patient an effective amount of a compound of the general formula (I), its salts, its prodrugs or its N-oxides.

A further aspect of the present invention relates to a method for the treatment and/or prophylaxis of affective disorders in a patient, which comprises administering to the patient an effective amount of a compound of the general formula (I), its salts, its prodrugs or its N-oxides.

A further aspect of the present invention relates to a method for the treatment of anxiety disorders and/or stress-dependent anxiety disorders in a patient, which comprises administering to the patient an effective amount of a compound of the general formula (I), its salts, its prodrugs or its N-oxides.

A further aspect of the present invention relates to a method for the treatment of memory impairments and/or Alzheimer's disease in a patient, which comprises administering to the patient an effective amount of a compound of the general formula (I), its salts, its prodrugs or its N-oxides.

A further aspect of the present invention relates to a method for the treatment of psychoses and/or psychotic disorders in a patient, which comprises administering to the patient an effective amount of a compound of the general formula (I), its salts, its prodrugs or its N-oxides.

A further aspect of the present invention relates to a method for the treatment of Cushing's syndrome and stress-dependent diseases in a patient, which comprises administering to the patient an effective amount of a compound of the general formula (I), its salts, its prodrugs or its N-oxides.

A further aspect of the present invention relates to a method for the treatment of sleep disorders in a patient, which comprises administering to the patient an effective amount of a compound of the general formula (I), its salts, its prodrugs or its N-oxides.

A further aspect of the present invention relates to a method for the treatment and/or prophylaxis of disorders selected from depressive disorders in a patient, which comprises administering to the patient an effective amount of a compound of the general formula (I), its salts, its prodrugs or its N-oxides. The depressive disorders especially encompass childhood onset mood disorders, i.e. depressive moods starting in childhood.

A further aspect of the present invention relates to a method for the treatment and/or prophylaxis of vasomotor disorders and thermoregulatory dysfunctions in a patient, which comprises administering to the patient an effective amount of a compound of the general formula (I), its salts, its prodrugs or its N-oxides.

A further aspect of the present invention relates to a method for the treatment and/or prophylaxis of addiction mediated by drugs, medicaments and/or other factors; of stress induced by withdrawal from one or more addiction-mediating factors; and/or of stress-induced relapse to addiction mediated by drugs, medicaments and/or other factors in a patient, which comprises administering to the patient an effective amount of a compound of the general formula (I), its salts, its prodrugs or its N-oxides.

A further aspect of the present invention relates to a method for the treatment and/or prophylaxis of disorders selected from schizophrenia and psychoses in a patient, which comprises administering to the patient an effective amount of a compound of the general formula (I), its salts, its prodrugs or its N-oxides.

A further aspect of the present invention relates to the use of a compound of the general formula (I), its salts, its prodrugs or its N-oxides for inhibiting development of tolerance to analgesic effects elicited by administration of analgesic agents such as, for example, morphines.

Accordingly, a further aspect of the present invention relates to a method for inhibiting the development of tolerance to analgesic effects elicited by administration of analgesic agents in a patient, which comprises administering to the patient an effective amount of a compound of the general formula (I), its salts, its prodrugs or its N-oxides.

Preferred compounds of the general formula (I), their salts, their prodrugs or their N-oxides are distinguished by a binding affinity Ki for the vasopressin V1b receptor subtype of less than about 100 nM, for example by a Ki in the range from 1 nM to 100 nM. Compounds of the formula (I) with a Ki of less than or equal to 20 nM are particularly preferred.

Preferred compounds of the general formula (I), their salts, their prodrugs or their N-oxides are further distinguished by having a selectivity for the vasopressin V1b receptor subtype vis-a-vis at least one of the closely related vasopressin/oxytocin receptor subtypes (for example vasopressin V1a, vasopressin V2 and/or oxytocin).

Preferred compounds of the general formula (I), their salts, their prodrugs or their N-oxides are further distinguished by having an improved metabolic stability.

The metabolic stability of a compound can be determined for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible to conclude from larger half-lives that the metabolic stability of the compound is improved. The stability in the presence of human liver microsomes is of particular interest since it makes it possible to predict the metabolic degradation of the compound in the human liver. Compounds with increased metabolic stability are therefore probably also degraded more slowly in the liver.

The slower metabolic degradation in the liver usually leads to higher and/or longer-lasting concentrations (effective levels) of the compound in the body and specifically in the brain, so that the elimination half-life of the compounds of the invention is increased. Increased and/or longer-lasting effective levels may lead to a better efficacy of the compound in the treatment or prophylaxis of various vasopressin-dependent or oxytocin-dependent diseases. An improved metabolic stability may additionally lead to an increased bioavailability after oral administration, because the compound is subjected, after being absorbed in the intestine, to less metabolic degradation in the liver (so-called first pass effect). An increased oral bioavailability may, because the concentration (effective level) of the compound is increased, lead to a better efficacy of the compound of the formula I after oral administration.

The compounds of the invention of the formula (I), their salts, their prodrugs or their N-oxides can be administered in various ways to achieve an effect. Mention may be made by way of example of intravenous, intramuscular or oral administration. Oral administration is particularly suitable.

The present invention also relates to pharmaceutical compositions which comprise an effective dose of a compound of the invention of the formula (I) or its salts, its prodrugs or its N-oxides, and suitable pharmaceutical carriers (drug carriers). Drug carriers are chosen according to the pharmaceutical form and the desired mode of administration.

The compounds of the invention of the general formula (I) or, where appropriate, suitable salts, prodrugs and N-oxides of these compounds can be used to manufacture pharmaceutical compositions for oral, sublingual, subcutaneous, intramuscular, intravenous, topical, intratracheal, intranasal, transdermal or rectal administration and be administered to animals or humans in unit dose forms mixed with conventional drug carriers for the prophylaxis and/or treatment of the above disorders or impairments.

Suitable unit dose forms include forms for oral administration, such as tablets, gelatin capsules, powders, granules, solutions or suspensions, forms for sublingual, buccal, intratracheal or intranasal administration, aerosols, implants, forms of subcutaneous, intramuscular or intravenous administration and forms of rectal administration.

The compounds of the invention can be used in creams, ointments or solutions for topical administration.

In order to achieve the desired prophylactic and/or therapeutic effect, the dose of the active compound of the formula (I), its salts, its prodrugs or its N-oxides can vary between 0.01 and 50 mg per kg of body weight and per day.

Each unit dose form may comprise from 0.05 to 5000 mg, preferably 1 to 1000 mg, of the active compound of the formula (I), its salts, its prodrugs or its N-oxides, in combination with a pharmaceutical carrier. This unit dose can be administered 1 to 5 times a day so that a daily dose of from 0.5 to 25 000 mg, preferably 1 to 5000 mg, is administered.

If a solid composition in the form of tablets is prepared, the compound of the formula (I), its salts, its prodrugs or its N-oxides, is mixed with a pharmaceutical carrier such as gelatin, starch, lactose, magnesium stearate, talc, silicon dioxide or the like.

The tablets can be coated with sucrose, a cellulose derivative or another suitable substance or be treated otherwise in order to display a prolonged or delayed activity and in order to release a predetermined amount of the active basic ingredient continuously.

A preparation in the form of gelatin capsules is obtained by mixing the active compound of the formula (I), its salts, its prodrugs or its N-oxides, with an extender and taking up the resulting mixture in soft or hard gelatin capsules.

A preparation in the form of a syrup or elixir or for administration in the form of drops may comprise the compound of the formula (I), its salts, its prodrugs or its N-oxides, together with a sweetener which is preferably calorie-free, methylparaben or propylparaben as antiseptics, a flavoring and a suitable coloring.

The water-dispersible powders or granules may comprise the compound of the formula (I), its salts, its prodrugs or its N-oxides, mixed with dispersants, wetting agents or suspending agents, such as polyvinylpyrrolidone, and sweeteners or taste improvers.

Rectal administration is achieved by the use of suppositories which are prepared with binders which melt at the rectal temperature, for example cocoa butter or polyethylene glycols. Parenteral administration is effected by using aqueous suspensions, isotonic salt solutions or sterile and injectable solutions which comprise pharmacologically suitable dispersants and/or wetting agents, for example propylene glycol or polyethylene glycol.

The compounds of the formula (I), their salts, their prodrugs or their N-oxides, can also be formulated as microcapsules or centrosome, if suitable with one or more carriers or additives.

In addition to the compounds of the general formula (I), their salts, their prodrugs or their N-oxides, the compositions of the invention may comprise further active components which may be beneficial for the treatment of the impairments or disorders indicated above.

A further embodiment of the present invention therefore relates to pharmaceutical compositions which comprise a plurality of active components, where at least one of these components is a compound of the invention of the formula (I), its salts, its prodrugs or its N-oxides.

Examples of synthetic routes for preparing the compounds of the invention of the general formula (I) or of the formula (I'), their salts, their prodrugs or their N-oxides, are described below. The compounds of the formula (I') are precursor compounds of the compounds of the invention of the formula (I) which can be converted by simple reactions known to the skilled worker, such as, for example, by deprotection and/or alkylation, under standard conditions into the compounds of the formula (I), or are compounds of the formula (I).

The oxindole compounds of the invention of the formula (I) and the compounds (I') can be prepared for example by the route outlined in Synthesis Scheme 1. In the following Synthesis Schemes 1 to 6, the groups A, B, Y, Het, $R^1$, $R^2$, $R^{Het\,and}$ $R^B$ have one of the meanings given above.

SYNTHESIS SCHEME 1

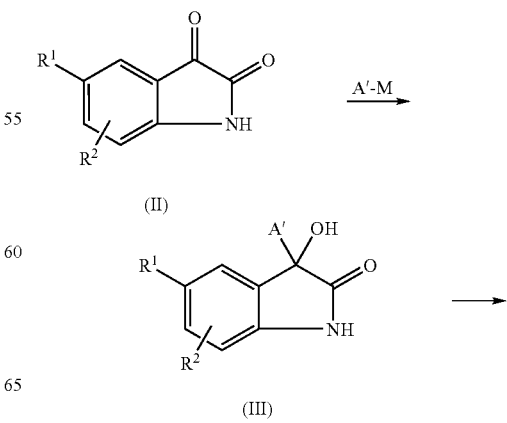

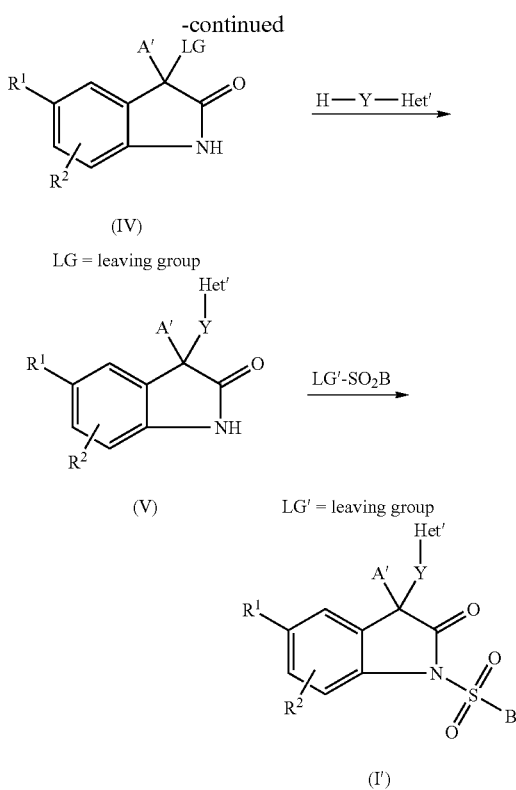

(IV) LG = leaving group (V) LG' = leaving group (I')

In Synthesis Scheme 1, Het' is a Het radical or is an optionally protected precursor or a surrogate of such a Het radical. An optionally protected precursor is a substituent which can be converted into the Het radical by conversion of functional groups, where appropriate by or after a deprotection. A' is an A radical or an optionally protected precursor of A which is converted into the A radical by conversion of functional groups, where appropriate by or after a deprotection. A surrogate in the sense of the present invention may be for example a leaving group or protective group which can subsequently be exchanged for a Het radical of the invention. The exchange in this connection can take place in one stage, for example by substitution, or in a plurality of stages, for example by deprotection and subsequent alkylation. It is further possible for the exchange to take place at the stage of compound (V) or at the stage of compound (I'). 3-Hydroxy-oxindoles (III) with a substituent A' in position 3, in which A' has one of the meanings given for A, or is a protected precursor of A, can be prepared by addition of organometallic compounds A'-M (M=Li, MgCl, MgBr) onto the 3-keto group of substituted isatins (II) in an ethereal solvent such as, for example, THF. For example, the lithium species of the formula A'-Li can be obtained from the iodoaryl compound A'-I by treatment with organolithium reagents such as, for example, n-butyllithium, in THF at low temperatures. It is possible alternatively to prepare from A'-Hal (Hal=Cl, Br, I) the corresponding Grignard compound by treatment with magnesium in an ethereal solvent such as, for example, THF. Compounds of the formula (III) in which the radical $R^1$ is a cyano group can be prepared starting from the corresponding compounds in which $R^1$ is iodine. For example, compounds of the formula (III) in which $R^1$ is halogen, such as bromine or iodine, are heated with zinc cyanide in dimethylformamide (DMF) in the presence of catalytic amounts of palladium tetrakis(triphenylphosphine) or instead with potassium cyanide in the presence of catalytic amounts of palladium tetrakis(triphenylphosphine) in tetrahydrofuran (THF) in accordance with the method described in J. Med. Chem. 1996, 39, 5072-5082.

The hydroxy group of the 3-hydroxyoxindoles (III) obtained in this way can be exchanged by methods known to the skilled worker for a leaving group LG (LG is for example halogen). LG is in this case normally selected from halide, mesylate, tosylate or similar groups. Thus, for example, the intermediate (IV) in which LG is chlorine can be prepared by treating the hydroxy compound (III) with thionyl chloride in the presence of a base such as, for example, pyridine, in a solvent such as, for example, dichloromethane.

Reaction of the compounds (IV) obtained in this way with primary or secondary amines of the formula H—Y-Het' in which Het' has one of the meanings given for Het in the description, is a protected precursor or a surrogate of such a Het group leads to 3-"Y-Het'"-substituted 3-aminooxindoles (V). The compounds of the formula (IV) are normally reacted in the presence of a base such as, for example, N,N-diisopropyl-ethylamine with primary or secondary amines of the formula H—Y-Het' in a solvent such as, for example, dichloromethane to give the corresponding 3-aminooxindoles (V) in which the linkage of the Y-Het' radical in position 3 of the oxindole structure takes place via a nitrogen atom. Deprotonation of the oxindole nitrogen with a suitable base, for example NaH or alcoholate such as potassium tert-butoxide, in an inert solvent such as tetrahydrofuran, and sulfonylation with compounds of the formula LG'-$SO_2$B (LG' is for example halogen, specifically chlorine) results in optionally protected compounds of the general formula (I). If A' is a protected precursor of a group A, compounds of the general formula (I) are obtained by deprotection following the synthetic sequence indicated above.

Further compounds of the general formula (I) can be obtained by subsequent functionalization and/or derivatization by methods known to the skilled worker. The indicated synthetic route can also be applied to analogous compounds.

Thus, compounds of the formula I in which A has a group $CH_2$—$R^{a2}$ (benzylic amines) can be prepared from compounds of the formula I which have an aldehyde group or a protected aldehyde group (e.g. a 5-methyl-1,3-dioxane ring) instead of the group $CH^2$—$R^{a2}$. The appropriately protected aldehyde-metal compounds A'-M can be prepared from commercially available iodo- or bromoaromatic compounds which have an aldehyde group by protecting the aldehyde group and metallation. In the case where A is an aromatic heterocycle, metallated heteroaromatic compounds having a protected formyl group can be prepared in an analogous manner (protection of the formyl function as cyclic acetal followed by lithium-halogen exchange or insertion of magnesium into the heteroaryl-halogen bond), e.g. from commercially available 2-bromo-4-formyl-3-methoxypyridine, 6-bromo-2-formylpyridine, 5-bromo-3-formylpyridine, 2-bromo-4-formylpyridine, 2-bromo-5-formylpyridine, 4-bromo-2-formylthiophene, 3-bromo-2-formylthiophene, 5-bromo-2-formylthiophene or 3-bromo-4-formylthiophene.

The lactams of the formula (III) which are obtained as intermediates in the synthetic sequence described above may where appropriate result as mixtures of enantiomers from the organometallic addition reaction, but the subsequent products (IV), (V) and (I') and the target compound (I) may also be in the form of mixtures of enantiomers. The enantiomers can be separated for example by HPLC chromatography with a chiral column or by chemical resolution by addition of L-leucinol in analogy to the method described in WO 03/008407.

The enantiomers are preferably separated at the stage of the compounds of the formulae (V) or (I).

Compounds of the formula H—Y-Het' are known or can be prepared in analogy to Synthesis Schemes 2 to 4 shown below. One of the preferred Y-Het radicals is pyridin-4-ylpiperazin-1-yl. The corresponding pyridin-4-yl-piperazine or its N-oxide can be prepared by the method described in Chem. Pharm. Bull. 2001, 41, 1314-1320.

SYNTHESIS SCHEME 2

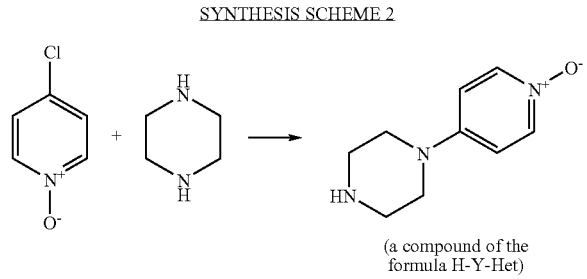

(a compound of the formula H-Y-Het)

Further compounds of the formula H—Y-Het' can be prepared in analogy to the reactions shown starting from halogenated (Cl, Br) heteroaromatic compounds.

One example thereof is the synthesis shown in Synthesis Scheme 3.

SYNTHESIS SCHEME 3

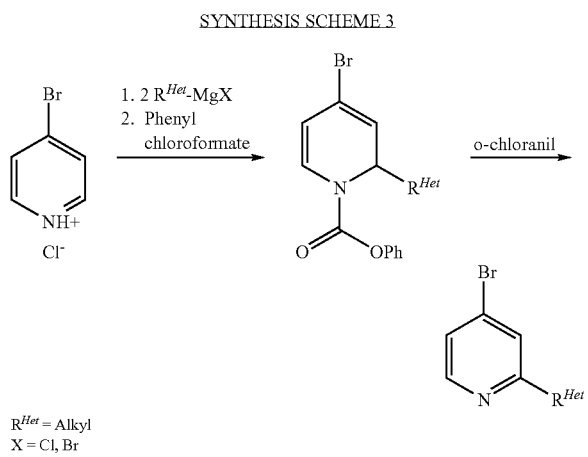

$R^{Het}$ = Alkyl
X = Cl, Br

Alkylated 2-alkyl-4-halopyridines can be prepared as shown by Grignard addition onto appropriate pyridinium salts. The dihydropyridine compounds formed as intermediates can be converted by aromatization with tetrachloro-o-benzoquinone (o-chloranil) in toluene/acetic acid into the corresponding compounds of the formula H—Y-Het.

Sulfonyl chlorides of the formula B—SO₂Cl can be converted as shown in Synthesis Scheme 4 in analogy to methods known from the literature, as described for example in Synthesis 1986, 852 or J. Org. Chem. 2003, 68, 8274-8276, by reaction of halogenated aromatic or heteroaromatic compounds with suitable organometallic compounds (e.g. butyllithium, methylmagnesium bromide) into compounds of the formula B-M (M=Li, MgCl, MgBr). These can be converted by successive reaction with SO₂ and thionyl chloride into the corresponding compounds of the formula B—SO₂Cl. Mention may be made by way of example thereof of the synthesis of 5-fluoropyridin-2-ylsulfonyl chloride, 5-methoxypyridin-2-ylsulfonyl chloride or 4-cyano-2-fluorobenzenesulfonyl chloride. It is possible alternatively to prepare sulfonyl chlorides also by reacting an aromatic compound of the formula H—B with bistrimethylsilyl sulfate (Eur. J. Med. Chem. 2001, 36, 809-828). Suitable halogenated aromatic or heteroaromatic compounds are known or can be prepared in analogy to known compounds.

SYNTHESIS SCHEME 4

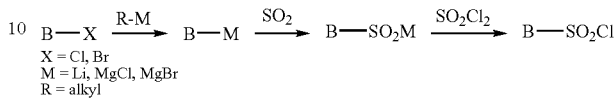

X = Cl, Br
M = Li, MgCl, MgBr
R = alkyl

A preferred example of the preparation of sulfonyl chlorides of the formula B—SO₂Cl in which B is an optionally substituted quinolin-8-yl radical is shown in Synthesis Scheme 5. In accordance with DE 4241303, the sulfonyl chloride is obtained starting from a quinoline which is unsubstituted in position 8 by reaction with chlorosulfonic acid and thionyl chloride. Quinolin-8-ylsulfonyl chlorides with further substitution can be prepared in analogy to this method.

SYNTHESIS SCHEME 5

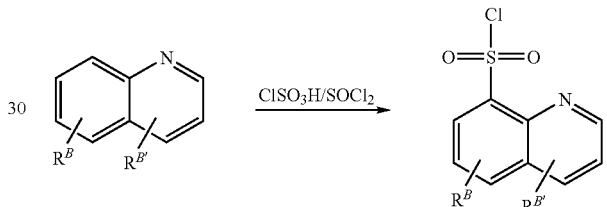

Substituted quinolines are known or can be prepared for example in analogy to the method described in J. Org. Chem. 1991, 56, 7288-7291.

The invention is explained in more detail below by means of examples without being restricted to the examples mentioned.

EXAMPLE 1

(±)-5-Chloro-3-(2,4-dimethoxyphenyl)-3-(4-pyridin-4-ylpiperazin-1-yl)-1-(quinoline-8-sulfonyl)-1,3-dihydroindol-2-one 1.1 5-Chloro-3-(2,4-dimethoxyphenyl)-3-(4-pyridin-4-ylpiperazin-1-yl)-1,3-dihydro-indol-2-one Pyridine (1.51 mL, 18.76 mmol) and thionyl chloride (1.03 mL, 14.07 mmol) were added to a solution of 5-chloro-3-(2, 4-dimethoxyphenyl)-3-hydroxy-1,3-dihydroindol-2-one (prepared as described in WO 2005/030755, 3.00 g, 9.38 mmol) in dichloromethane (70 mL) while cooling in ice. The reaction mixture was then stirred at 0° C. for 1 hour. While stirring, water was added to the reaction mixture, and it was then extracted with dichloromethane. The organic phase was washed with water and saturated brine, dried over sodium sulfate and concentrated under reduced pressure. 1-Pyridin-4-yl-piperazine (2.17 g, 13.31 mmol) was added to a solution of the 3-chloro-oxindole intermediate obtained in this way in dimethylformamide (25 mL), and the reaction mixture was stirred at room temperature for 12 h. The reaction mixture was concentrated under reduced pressure and the residue was partitioned between ethyl acetate and water. The aqueous phase was extracted again with ethyl acetate. The combined organic phase was dried over sodium sulfate and concentrated under reduced pressure, resulting in 1.00 g of the title compound which was employed without further purification in the next step.

ESI-MS: [M+H]$^+$=465.25;

1.2 5-Chloro-3-(2,4-dimethoxyphenyl)-3-(4-pyridin-4-ylpiperazin-1-yl)-1-(quinoline-8-sulfonyl)-1,3-dihydroindol-2-one Potassium tert-butoxide (26.6 mg, 0.24 mmol) was added to a solution of 5-chloro-3-(2,4-dimethoxyphenyl)-3-(4-pyridin-4-ylpiperazin-1-yl)-1,3-dihydroindol-2-one (0.10 g, 0.22 mmol) in dimethylformamide (4 mL) at 0° C., and the mixture was stirred at 0° C. for 1 hour. Then 8-quinolinesulfonyl chloride (53.9 mg, 0.24 mmol) was added to the reaction solution while cooling in ice, and the mixture was stirred at room temperature for 12 hours. Water was cautiously added to the mixture, which was extracted twice with ethyl acetate. The combined organic phase was washed with water and saturated brine, dried over sodium sulfate and concentrated under reduced pressure. Chromatographic purification of the residue on silica gel (mobile phase gradient 0-7% methanol in dichloromethane) afforded 57.0 mg of the title compound.

ESI-MS: 658.15, [M+H]$^+$=657.15, 656.15;
$^1$H-NMR (400 MHz, DMSO) δ (ppm): 8.76 (1H, m sym.), 8.65 (1H, d), 8.58 (1H, d), 8.39 (1H, d), 8.15 (1H, d), 8.10 (2H, d), 7.85 (1H, t), 7.67 (2H, d), 7.54 (1H, d), 6.85 (1H, s), 6.65 (1H, d), 6.54 (2H, d), 6.44 (1H, s), 3.73 (3H, s), 3.05 (3H, s), 2.92-2.63 (2H, m br.), 2.10 (2H, m br.).

The following compounds 2 to 139 were prepared in analogous manner to the description in Example 1. In some examples, the compounds were purified by preparative reversed phase HPLC (mobile phase: gradient from 10% to 80% acetonitrile in water, 0.1% trifluoroacetic acid or 0.2% acetic acid as modulator) and were, if they contain a basic nitrogen in the molecule, isolated as trifluoroacetic acid salts or acetic acid salts.

EXAMPLE 2

(±)-5-Chloro-3-(2,3-dimethoxyphenyl)-3-(4-pyridin-4-ylpiperazin-1-yl)-1-(quinoline-8-sulfonyl)-1,3-dihydroindol-2-one (hydrochloride)

ESI-MS: 658.15, [M+H]$^+$=657.15, 656.15;
$^1$H-NMR (400 MHz, DMSO) δ (ppm): 13.42 (1H, s br.), 8.75 (1H, m), 8.64 (1H, d), 8.55 (1H, d), 8.36 (1H, d), 8.23 (1H, d), 8.19 (1H, d), 7.84 (1H, t), 7.67 (1H, m sym.), 7.60 (1H, d), 7.43 (1H, d), 7.17 (1H, t), 7.00 (1H, d), 6.93 (2H, m sym.), 6.82 (1H, s), 3.68 (3H, s), 2.84 (3H, s), 2.27-2.10 (2H, m br.).

EXAMPLE 3

(±)-5-Cyano-1-(2,4-dimethoxybenzenesulfonyl)-3-(2-ethoxypyridin-3-yl)-3-(4-pyridin-4-ylpiperazin-1-yl)-2,3-dihydro-1H-indol-2-one ESI-MS: [M+H]$^+$=641.55;
1H-NMR (400 MHz, DMSO) δ (ppm): 8.24 (1H, d), 8.15 (3H, m), 8.03-7.92 (3H, m), 7.42 (1H, s), 7.16 (1H, m sym.), 6.71 (4H, m), 4.04 (2H, quint.), 3.82 (3H, s), 3.66 (3H, s), 2.30 (2H, m), 0.94 (3H, t).

EXAMPLE 4

(±)-5-Cyano-3-(2-methoxypyridin-3-yl)-3-(4-pyridin-4-ylpiperazin-1-yl)-1-(quinoline-8-sulfonyl)-2,3-dihydro-1H-indol-2-one ESI-MS: [M+H]$^+$=618.15;
$^1$H-NMR (400 MHz, DMSO) δ (ppm): 8.75 (1H, d), 8.68 (1H, d), 8.59 (1H, d), 8.45 (1H, d), 8.37 (1H, d), 8.22 (1H, d), 8.12 (3H, m), 8.03 (1H, d), 7.88 (1H, t), 7.68 (1H, m sym.), 7.44 (1H, s), 7.15 (1H, t), 6.58 (2H, d), 3.05 (3H, s), 2.16 (2H, m br.).

EXAMPLE 5

(±)-5-Cyano-3-(2-ethoxypyridin-3-yl)-3-(4-pyridin-4-ylpiperazin-1-yl)-1-(quinoline-8-sulfonyl)-2,3-dihydro-1H-indol-2-one ESI-MS: [M+H]$^+$=632.15;
$^1$H-NMR (400 MHz, DMSO) δ (ppm): 8.74 (1H, d), 8.68 (1H, d), 8.58 (1H, d), 8.44-8.33 (2H, m sym.), 8.17 (1H, d), 8.14-8.06 (3H, m), 8.04 (1H, d), 7.87 (1H, t), 7.68 (1H, m sym.), 7.38 (1H, s), 7.12 (1H, t), 6.53 (2H, d), 3.73 (1H, quint.), 3.57 (1H, quint.), 2.06 (2H, m br.), 0.68 (3H, t).

EXAMPLE 6

(±)-5-Cyano-3-(2-ethoxyphenyl)-3-(2-methyl-4-pyridin-4-ylpiperazin-1-yl)-1-(quinoline-8-sulfonyl)-2,3-dihydro-1H-indol-2-one

ESI-MS: [M+H]$^+$=645.25;

EXAMPLE 7

(±)-5-Cyano-3-(2-ethoxyphenyl)-1-(3-methylquinoline-8-sulfonyl)-3-(4-pyridin-4-yl-piperazin-1-yl)-2,3-dihydro-1H-indol-2-one ESI-MS: [M+H]$^+$=645.15;
$^1$H-NMR (400 MHz, CDCl$_3$) δ (ppm): 8.71 (1H, d), 8.55 (1H, s), 8.47 (1H, d), 8.20 (2H, d), 8.04-7.93 (2H, m), 7.81-7.70 (3H, m), 7.33-7.22 (m+ CHCl$_3$), 7.15 (1H, s), 7.01 (1H, t), 6.74 (1H, d), 6.39 (2H, d), 3.74 (1H, quint.), 3.55 (1H, quint.), 2.51 (3H, s), 0.97 (3H, t).

EXAMPLE 8

(±)-5-Chloro-3-pyridin-2-yl-3-(4-pyridin-4-ylpiperazin-1-yl)-1-(quinoline-8-sulfonyl)-1,3-dihydroindol-2-one ESI-MS: 597.15;
$^1$H-NMR (400 MHz, CDCl$_3$) δ (ppm): 8.80 (1H, d), 8.47 (1H, d), 8.26-8.15 (4H, m), 8.12 (1H, d), 7.87 (1H, d), 7.74 (1H, t), 7.63-7.50 (2H, m), 7.44-7.35 (2H, m), 7.28-7.20 (1H, m), 7.01 (1H, t), 6.46 (2H, d), 3.11 (4H, m sym.), 2.66 (2H, m), 2.31 (2H, m), 1.60 (6H, s).

EXAMPLE 9

(±)-5-Chloro-3-(3-methylpyridin-2-yl)-3-(4-pyridin-4-ylpiperazin-1-yl)-1-(quinoline-8-sulfonyl)-1,3-dihydroindol-2-one

ESI-MS: 611.15;

EXAMPLE 10

(±)-5-Chloro-3-(6-chloro-2-methoxypyridin-3-yl)-3-(4-pyridin-4-ylpiperazin-1-yl)-1-(quinoline-8-sulfonyl)-1,3-dihydroindol-2-one ESI-MS: 663.15, 661.15;
$^1$H-NMR (400 MHz, CDCl$_3$) δ (ppm): 8.77 (1H, d), 8.73 (1H, d), 8.30 (1H, d), 8.27-8.18 (3H, m), 8.12 (1H, d), 8.01 (1H, d), 7.74 (1H, t), 7.48 (1H, m sym.), 7.44 (1H, d), 6.99 (1H, d), 6.82 (1H, s), 6.46 (2H, d), 3.20 (3H, s), 3.05 (2H, m br.), 2.40 (2m br.).

EXAMPLE 11

(±)-5-Cyano-3-(2-ethoxyphenyl)-1-(5-methylpyridine-2-sulfonyl)-3-(4-pyridin-4-yl-piperazin-1-yl)-2,3-dihydro-1H-indol-2-one ESI-MS: [M+H]$^+$=595.25;
$^1$H-NMR (400 MHz, CDCl$_3$) δ (ppm): 8.35 (1H, s), 8.27 (2H, d), 8.22 (1H, d), 8.13 (1H, d), 7.84 (1H, d), 7.75 (1H, d), 7.65 (1H, d), 7.28 (1H, t), 7.15 (1H, s), 7.06 (1H, t), 6.79 (1H, d), 6.56 (2H, d), 3.92 (1H, quint.), 3.78 (1H, quint.), 3.72-3.57 (m br.), 3.22-2.78 (3H, m br.), 2.37 (5H, s), 2.03 (1H, s br.), 1.10 (3H, t).

EXAMPLE 12

(±)-5-Cyano-1-(5-chloroquinoline-8-sulfonyl)-3-(2-ethoxyphenyl)-3-(4-pyridin-4-yl-piperazin-1-yl)-2,3-dihydro-1H-indol-2-one ESI-MS: 665.05;
$^1$H-NMR (400 MHz, CDCl$_3$) δ (ppm): 8.76-8.70 (2H, m), 8.67 (1H, d), 8.43 (1H, d), 8.22 (2H, s br.), 7.82 (1H, d), 7.79 (1H, d), 7.73 (1H, d), 7.58 (1H, m sym.), 7.31-7.20 (m+CHCl$_3$), 7.14 (1H, s), 7.02 (1H, t), 6.76 (1H, d), 6.37 (2H, s br.), 3.81 (1H, quint.), 3.61 (1H, quint.), 3.54-1.95 (m br.), 1.00 (3H, t).

EXAMPLE 13

(±)-5-Cyano-3-(2-ethoxy-5-methoxyphenyl)-3-(4-pyridin-4-yl-piperazin-1-yl)-1-(quinoline-8-sulfonyl)-2,3-dihydro-1H-indol-2-one ESI-MS: [M+H]$^+$=661.15;

EXAMPLE 14

(±)-5-Cyano-3-(2-ethoxyphenyl)-1-(pyridine-2-sulfonyl)-3-(4-pyridin-4-yl-piperazin-1-yl)-2,3-dihydro-1H-indol-2-one ESI-MS: [M+H]$^+$=581.15;
$^1$H-NMR (500 MHz, DMSO) δ (ppm): 8.67 (1H, d), 8.30 (1H, d), 8.22-8.11 (3H, m), 8.01 (1H, d), 7.93 (1H, d), 7.88 (1H, d), 7.74 (1H, m), 7.36-7.30 (2H, m), 7.11 (1H, t), 6.94 (1H, d), 6.73 (2H, d), 3.77 (1H, quint.), 3.70 (1H, quint.), 2.95 (m br.), 2.22 (m br.), 1.81 (m br.), 0.93 (3H, t).

EXAMPLE 15

(±)-5-Cyano-3-(2-ethoxyphenyl)-3-[4-(3-methylpyridin-4-yl)-piperazin-1-yl]-1-(quinoline-8-sulfonyl)-2,3-dihydro-1H-indol-2-one ESI-MS: [M+H]$^+$=645.15;
$^1$H-NMR (400 MHz, CDCl$_3$) δ (ppm): 8.95 (1H, d), 8.67 (1H, d), 8.46 (1H, d), 8.22 (2H, s), 8.19 (1H, d), 8.13 (1H, d), 7.78 (2H, t), 7.73 (1H, d), 7.45 (1H, m sym.), 7.32-7.20 (m+CHCl$_3$), 7.14 (1H, s), 7.02 (1H, t), 6.78 (1H, d), 6.56 (1H, d), 3.87 (1H, quint.), 3.66 (1H, quint.), 3.48 (3H, s), 3.11-2.22 (m br.), 1.86 (3H, s), 1.10 (3H, t), 0.92 (1H, s br.).

EXAMPLE 16

(±)-5-Cyano-3-(2-ethoxyphenyl)-1-(4-methylquinoline-8-sulfonyl)-3-(4-pyridin-4-yl-piperazin-1-yl)-2,3-dihydro-1H-indol-2-one

ESI-MS: [M+H]$^+$=645.25;

EXAMPLE 17

(±)-5-Cyano-3-(2-ethoxyphenyl)-3-(3-methyl-4-pyridin-4-ylpiperazin-1-yl)-1-(quinoline-8-sulfonyl)-2,3-dihydro-1H-indol-2-one

ESI-MS: [M+H]$^+$=645.25;

EXAMPLE 18

(±)-5-Cyano-3-(2-ethoxy-5-methoxyphenyl)-3-[4-(2-methylpyridin-4-yl)piperazin-1-yl]-1-(4-methylquinoline-8-sulfonyl)-2,3-dihydro-1H-indol-2-one ESI-MS: [M+H]$^+$=689.15;
$^1$H-NMR (500 MHz, CDCl$_3$) δ (ppm): 8.69 (1H, d), 8.50 (1H, d), 8.44 (1H, d), 8.29 (1H, d), 8.10 (1H, d), 7.52 (2H, t), 7.39 (1H, s), 7.29 (1H, d), 7.16 (1H, s), 6.78 (1H, dd), 6.69 (1H, d), 6.27 (1H, s), 6.20 (1H, m sym.), 3.78 (3H, s), 3.75 (1H, quint.), 3.56 (1H, quint.), 3.50-2.78 (4H, m br.), 2.70 (3H, s), 2.39 (3H, s), 2.33-1.92 (4H, m br.), 1.00 (3H, t).

EXAMPLE 19

(±)-5-Cyano-3-(6-chloro-2-methoxypyridin-3-yl)-3-(4-pyridin-4-ylpiperazin-1-yl)-1-(quinoline-8-sulfonyl)-2,3-dihydro-1H-indol-2-one ESI-MS: 652.0;
$^1$H-NMR (500 MHz, CDCl$_3$) δ (ppm): 8.78 (1H, d), 8.70 (1H, d), 8.50 (1H, d), 8.27 (1H, d), 8.22 (2H, d), 8.15 (1H, d), 8.03 (1H, d), 7.82-7.71 (2H, m), 7.48 (1H, m), 7.17 (1H, s), 7.02 (1H, d), 6.44 (2H, d), 3.36-2.90 [7H, m br, incl, 3.19 (3H, s)], 2.48-2.20 (4H, m br.).

EXAMPLE 20

(±)-5-Cyano-3-(2-ethoxy-5-methoxyphenyl)-1-(5-methylpyridine-2-sulfonyl)-3-((1S, 4S)-5-pyridin-4-yl-2,5-diazabicyclo[2.2.1]hept-2-yl)-2,3-dihydro-1H-indol-2-one

ESI-MS: [M+H]$^+$=637.25;

EXAMPLE 21

(±)-5-Cyano-3-(2-isopropoxy-5-methoxyphenyl)-1-(5-methylpyridine-2-sulfonyl)-3-(4-pyridin-4-ylpiperazin-1-yl)-2,3-dihydro-1H-indol-2-one ESI-MS: [M+H]$^+$=639.25;
$^1$H-NMR (500 MHz, CDCl$_3$) δ (ppm): 8.32 (1H, s), 8.26 (2H, d), 8.22 (1H, d), 8.11 (1H, d), 7.73 (1H, d), 7.66 (1H, d), 7.44 (1H, s), 7.16 (1H, s), 6.82 (1H, m), 6.71 (1H, d), 6.54 (1H, d), 4.35 (1H, quint.), 3.80 (3H, s), 3.65 (1H, s br.), 3.49 (1H, s br.), 3.18 (1H, s br.), 3.02 (1H, s br.), 2.86 (1H, s br.), 2.36-2.22 [5H, m incl. 2.32 (3H, s)], 1.95 (1H, s br.), 1.16 (3H, d), 0.80 (3H, d),

EXAMPLE 22

(±)-5-Cyano-3-(2-ethoxyphenyl)-1-(5-methoxypyridine-2-sulfonyl)-3-(4-pyridin-4-yl-piperazin-1-yl)-2,3-dihydro-1H-indol-2-one

ESI-MS: [M+H]$^+$=611.25;

EXAMPLE 23

(±)-5-Cyano-3-(6-chloro-2-ethoxypyridin-3-yl)-1-(5-methylpyridine-2-sulfonyl)-3-(4-pyridin-4-ylpiperazin-1-yl)-2,3-dihydro-1H-indol-2-one ESI-MS: 630.15;
$^1$H-NMR (500 MHz, CDCl$_3$) δ (ppm): 8.36 (1H, s), 8.28 (2H, d), 8.21 (1H, d), 8.15 (1H, d), 8.05 (1H, d), 7.78 (1H, d), 7.70 (1H, d), 7.13 (1H, s), 7.03 (1H, d), 6.56 (2H, d), 4.13 (2H, m sym.), 2.44 (2H, m sym.), 2.38 (3H, s), 1.73 (2H, s br.), 3.65 (1H, s br.), 3.49 (1H, s br.), 3.18 (1H, s br.), 3.02 (1H, s br.), 2.86 (1H, s br.), 1.00 (3H, t).

EXAMPLE 24

(±)-5-Cyano-3-(6-chloro-2-ethoxypyridin-3-yl)-3-(4-pyridin-4-ylpiperazin-1-yl)-1-(quinoline-8-sulfonyl)-2,3-dihydro-1H-indol-2-one

ESI-MS: 666.15;

EXAMPLE 25

(±)-5-Cyano-3-(2-ethoxyphenyl)-1-(5-methoxyquinoline-8-sulfonyl)-3-(4-pyridin-4-yl-piperazin-1-yl)-2,3-dihydro-1H-indol-2-one ESI-MS: [M+H]$^+$=661.15;
$^1$H-NMR (400 MHz, CDCl$_3$) δ (ppm): 8.73 (1H, d), 8.63 (1H, m), 8.60 (1H, d), 8.45 (1H, d), 8.19 (2H, d), 7.78 (1H, d), 7.72 (1H, d), 7.43 (1H, m), 7.30-7.22 (m+ CHCl$_3$), 7.13 (1H, s), 7.00 (1H, t), 6.95 (1H, d), 6.77 (1H, d), 6.33 (2H, d), 4.06 (3H, s), 3.84 (1H, quint.), 3.70 (1H, quint.), 3.19-2.53 (4H, m br.), 2.36-1.85 (3H, m br.), 1.60 (3H, s br.), 1.08 (3H, t).

EXAMPLE 26

(±)-5-Cyano-3-(2-ethoxyphenyl)-1-(5-fluoroquinoline-8-sulfonyl)-3-(4-pyridin-4-yl-piperazin-1-yl)-2,3-dihydro-1H-indol-2-one ESI-MS: [M+H]$^+$=649.15;
$^1$H-NMR (500 MHz, DMSO) δ (ppm): 8.83 (1H, s), 8.70 (1H, t), 8.62 (1H, d), 8.32 (1H, d), 8.26 (2H, d), 8.02 (1H, d), 7.85 (1H, d), 7.76 (1H, m), 7.70 (1H, t), 7.30 (1H, t), 7.26 (1H, s), 7.08 (1H, t), 6.97-6.80 (3H, m), 4.00 (1H, s br.), 3.66-2.78 [m br, +H$_2$O incl, 3.60 (1H, quint.)], 2.00 (2H, s br.), 0.99-0.67 [4H, m br. incl. 0.76 (3H, t)].

EXAMPLE 27

(±)-5-Cyano-3-(6-chloro-2-ethoxypyridin-3-yl)-3-[4-(2-methylpyridin-4-yl)-piperazin-1-yl]-1-(quinoline-8-sulfonyl)-2,3-dihydro-1H-indol-2-one ESI-MS: 680.70;
$^1$H-NMR (500 MHz, CDCl$_3$) δ (ppm): 8.80 (1H, d), 8.70 (1H, s), 8.50 (1H, d), 8.25 (1H, d), 8.20-8.08 (2H, m), 8.00 (1H, d), 7.87-7.71 (2H, m), 7.50 (1H, m), 7.12 (1H, s), 6.98 (1H, d), 6.32 (1H, s), 6.25 (1H, d), 3.97 (1H, quint.), 3.75 (1H, quint.), 2.97 (2H, s br.), 2.43 (3H, s), 2.24 (2H, s br.), 0.86 (3H, t).

EXAMPLE 28

(±)-5-Cyano-3-(6-chloro-2-ethoxypyridin-3-yl)-1-(2,4-dimethoxybenzenesulfonyl)-3-[4-(2-methylpyridin-4-yl)piperazin-1-yl]-2,3-dihydro-1H-indol-2-one ESI-MS: 699.70;
$^1$H-NMR (500 MHz, DMSO) δ (ppm): 8.25 (1H, d), 8.05-7.90 (4H, m), 7.50 (1H, s), 7.23 (1H, d), 6.76-6.66 (2H, m), 6.58 (1H, s), 6.53 (1H, m), 4.04 (2H, m sym.), 3.82 (3H, s), 3.65 (3H, s), 2.29 (3H, s), 0.94 (3H, t).

EXAMPLE 29

(±)-5-Cyano-3-(6-chloro-2-ethoxypyridin-3-yl)-1-(2,4-dimethoxybenzenesulfonyl)-3-(4-pyridin-4-ylpiperazin-1-yl)-2,3-dihydro-1H-indol-2-one

ESI-MS: 675.70;

EXAMPLE 30

(±)-5-Cyano-3-(6-chloro-2-ethoxypyridin-3-yl)-1-(4-methylquinoline-8-sulfonyl)-3-(4-pyridin-4-ylpiperazin-1-yl)-2,3-dihydro-1H-indol-2-one ESI-MS: 680.70;
$^1$H-NMR (500 MHz, CDCl$_3$) δ (ppm): 8.78 (1H, d), 8.53 (1H, d), 8.45 (1H, d), 8.33 (1H, d), 8.22 (2H, d), 8.00 (1H, d), 7.81-7.73 (2H, m), 7.31 (1H, s), 7.12 (1H, s), 7.00 (1H, d), 6.42 (2H, d), 3.97 (1H, quint.), 3.73 (1H, quint.), 3.11-2.68 [4H, m br, incl, 2.74 (3H, s)], 2.35-2.01 (2H, m br.), 0.86 (3H, t).

EXAMPLE 31

(±)-5-Cyano-3-(2-ethoxy-4-fluorophenyl)-1-(5-methoxyquinoline-8-sulfonyl)-3-(4-pyridin-4-ylpiperazin-1-yl)-2,3-dihydro-1H-indol-2-one ESI-MS: [M+H]$^+$=679.20;
$^1$H-NMR (500 MHz, CDCl$_3$) δ (ppm): 8.72 (1H, d), 8.64 (1H, m), 8.60 (1H, d), 8.44 (1H, d), 8.20 (2H, m), 7.73 (2H, m), 7.42 (1H, m), 7.12 (1H, s), 6.95 (1H, d), 6.73 (1H, td), 6.50 (1H, d), 6.33 (2H, d), 4.07 (3H, s), 3.80 (1H, quint.), 3.63 (1H, quint.), 3.11-2.54 (4H, m), 2.40-1.88 (3H, m), 1.10 (3H, t).

EXAMPLE 32

(±)-5-Cyano-3-(2-ethoxy-4-fluorophenyl)-1-(5-methoxypyridine-2-sulfonyl)-3-(4-pyridin-4-ylpiperazin-1-yl)-2,3-dihydro-1H-indol-2-one ESI-MS: [M+H]$^+$=629.15;
$^1$H-NMR (500 MHz, CDCl$_3$) δ (ppm): 8.30 (1H, d), 8.25 (2H, m), 8.22 (1H, s), 8.13 (1H, d), 7.80 (1H, t), 7.65 (1H, d), 7.31 (1H, d), 7.14 (1H, s), 6.77 (1H, t), 6.59-6.50 (3H, m), 3.88 (1H, quint.), 3.83 (3H, s), 3.75 (1H, quint.), 3.70-2.72 (5H, m br.), 2.34 (2H, d br.), 1.90 (1H, s br.), 1.13 (3H, t).

EXAMPLE 33

(±)-5-Cyano-3-(2-ethoxy-5-methoxyphenyl)-1-(5-methoxyquinoline-8-sulfonyl)-3-[4-(2-methylpyridin-4-yl)piperazin-1-yl]-2,3-dihydro-1H-indol-2-one ESI-MS: [M+H]$^+$=705.30;
$^1$H-NMR (500 MHz, CDCl$_3$) δ (ppm): 8.73 (1H, d), 8.64 (1H, s), 8.60 (1H, d), 8.43 (1H, d), 8.10 (1H, d), 7.71 (1H, d), 7.41 (1H, m), 7.37 (1H, s), 7.15 (1H, s), 6.95 (1H, d), 6.79 (1H, d), 6.70 (1H, d), 6.25 (1H, s), 6.18 (1H, m), 4.07 (3H, s), 3.79 (3H, s), 3.74 (1H, quint.), 3.57 (1H, quint.), 3.47 (1H, s br.), 3.07 (1H, s br.), 2.87 (2H, m br.), 2.61 (1H, s br.), 2.40 (3H, s), 2.28 (1H, s br.), 1.01 (3H, t).

EXAMPLE 34

(±)-5-Cyano-3-(6-chloro-2-ethoxypyridin-3-yl)-1-(5-methoxypyridine-2-sulfonyl)-3-[4-(2-methylpyridin-4-yl)piperazin-1-yl]-2,3-dihydro-1H-indol-2-one ESI-MS: 660.20;
$^1$H-NMR (500 MHz, CDCl$_3$) δ (ppm): 8.30 (1H, d), 8.25 (1H, s), 8.15 (2H, m), 8.04 (1H, d), 7.69 (1H, d), 7.34 (1H, d), 7.13 (1H, s), 7.03 (1H, d), 6.44 (1H, s), 6.40 (1H, d), 4.14 (2H, m sym.), 3.88 (3H, s), 2.45 (6H, s), 1.03 (3H, t).

EXAMPLE 35

(±)-5-Cyano-3-(2-ethoxy-5-methoxyphenyl)-1-(5-methoxypyridine-2-sulfonyl)-3-[4-(2-methylpyridin-4-yl)piperazin-1-yl]-2,3-dihydro-1H-indol-2-one ESI-MS: [M+H]$^+$=655.25;
$^1$H-NMR (500 MHz, CDCl$_3$) δ (ppm): 8.30 (1H, d), 8.22 (1H, s), 8.16-8.10 (2H, m), 7.64 (1H, d), 7.43 (1H, s), 7.31 (1H, d), 7.19 (1H, s), 6.80 (1H, d), 6.71 (1H, d), 6.44 (1H, s), 6.39 (1H, d), 3.83 (2H, s), 3.80 (6H, s), 3.75-2.75 [3H, m br, incl, 3.70 (1H, quint.)], 2.45 (3H, s), 2.36 (1H, s br.), 1.08 (3H, t).

EXAMPLE 36

(±)-5-Cyano-3-(6-chloro-2-ethoxypyridin-3-yl)-1-(5-methoxypyridine-2-sulfonyl)-3-(4-pyridin-4-ylpiperazin-1-yl)-2,3-dihydro-1H-indol-2-one ESI-MS: 646.20;
$^1$H-NMR (500 MHz, CDCl$_3$) δ (ppm): 8.33-8.20 (4H, m), 8.16 (1H, d), 8.05 (1H, d), 7.70 (1H, d), 7.34 (1H, d), 7.13 (1H, s), 7.03 (1H, s), 6.58 (2H, d), 4.12 (2H, m sym.), 3.86 (3H, s), 3.26 (6H, s br.), 2.55 (2H, m br.), 1.01 (3H, t).

EXAMPLE 37

(±)-5-Chloro-3-(2-methoxyphenyl)-3-(4-pyridin-4-ylpiperazin-1-yl)-1-(quinoline-8-sulfonyl)-1,3-dihydroindol-2-one ESI-MS: 628.3, M=626.2,314.5, M/2=313.6, 119.1, 101.1;
$^1$H-NMR (400 MHz, CDCl$_3$) δ (ppm): 8.78 (1H, d), 8.73 (1H, m), 8.28 (1H, d), 8.24 (1H, d), 8.18 (2H, s br.), 8.11 (1H, d), 7.82-7.70 (2H, m), 7.50 (1H, m sym.), 7.40 (1H, d), 7.31-7.18 (m+ CHCl$_3$), 7.02 (1H, t), 6.87 (1H, s), 6.73 (1H, d), 6.44 (2H, m), 3.23 (3H, s), 3.06 (s br.), 2.33 (s br.).

EXAMPLE 38

(±)-5-Cyano-3-(2-ethoxyphenyl)-3-(4-pyridin-4-ylpiperazin-1-yl)-1-(quinoline-8-sulfonyl)-2,3-dihydro-1H-indol-2-one ESI-MS: [M+H]$^+$=631.20;
$^1$H-NMR (400 MHz, CDCl$_3$) δ (ppm): 8.80 (1H, d), 8.67 (1H, d), 8.46 (1H, d), 8.27-8.16 (3H, m), 8.08 (1H, d), 7.81-7.68 (3H, m), 7.48 (1H, m sym.), 7.33-7.22 (m+ CHCl$_3$), 3.18-2.53 (4H, m br.), 2.31-1.92 (2H, m br.), 1.06 (3H, t).

EXAMPLE 39

(±)-3-(2-Methoxyphenyl)-6-methyl-3-(4-pyridin-4-ylpiperazin-1-yl)-1-(quinoline-8-sulfonyl)-1,3-dihydroindol-2-one ESI-MS: [M+H]$^+$=606.35; 303.65;
$^1$H-NMR (500 MHz, CDCl$_3$) δ (ppm): 8.86-8.74 (2H, m), 8.32-8.05 (5H, m), 7.83-7.70 (2H, m), 7.51-7.43 (1H, m), 7.20 (1H, t), 6.92 (1H, d), 6.78 (1H, d), 6.71 (1H, d), 6.57 (2H, m), 3.3 (m br.), 3.10 (3H, s), 2.48 (3H, s).

EXAMPLE 40

(±)-5-Chloro-3-(2-chlorophenyl)-3-(4-pyridin-4-ylpiperazin-1-yl)-1-(quinoline-8-sulfonyl)-1,3-dihydroindol-2-one

EXAMPLE 41

(±)-5-Chloro-3-(5-dimethylaminomethyl-2-methoxyphenyl)-3-(4-pyridin-4-ylpiperazin-1-yl)-1-(quinoline-8-sulfonyl)-1,3-dihydroindol-2-one

ESI-MS: [M+H]$^+$=683.20, 342.1;

EXAMPLE 42

(±)-5-Chloro-3-(2-methoxypyridin-3-yl)-3-(4-pyridin-4-ylpiperazin-1-yl)-1-(quinoline-8-sulfonyl)-1,3-dihydroindol-2-one

ESI-MS: 627.15, 314.15, 101.05;

EXAMPLE 43

(±)-5-Cyano-3-(2-methoxyphenyl)-3-(4-pyridin-4-ylpiperazin-1-yl)-1-(quinoline-8-sulfonyl)-2,3-dihydro-1H-indol-2-one

ESI-MS: [M+H]$^+$=617.15, 309.1;

EXAMPLE 44

(±)-5-Cyano-3-(2-ethoxyphenyl)-3-[4-(2-methylpyridin-4-yl)piperazin-1-yl]-1-(quinoline-8-sulfonyl)-2,3-dihydro-1H-indol-2-one ESI-MS: 647.20, 646.25, [M+H]$^+$, [M+2H]$^{2+}$=645.25, 323.10;
$^1$H-NMR (400 MHz, CDCl$_3$) δ (ppm): 8.80 (1H, d), 8.67 (1H, m), 8.46 (1H, d), 8.25 (1H, d), 8.11 (2H, t), 7.75 (3H, q), 7.49 (1H, m), 7.13 (1H, s), 7.02 (1H, t), 6.76 (1H, d), 6.29 (1H, s), 6.17 (1H, m), 3.81 (1H, m sym.), 3.61 (1H, m sym.), 2.93 (m br.), 2.44 (3H, s), 1.00 (3H, t).

EXAMPLE 45

(±)-5-Chloro-3-(2-methoxy-5-methylaminomethylphenyl)-3-(4-pyridin-4-ylpiperazin-1-yl)-1-(quinoline-8-sulfonyl)-1,3-dihydroindol-2-one

ESI-MS: 669.15, 334.95.

EXAMPLE 46

(±)-5-Cyano-3-(2-ethoxy-4-fluorophenyl)-3-(4-pyridin-4-ylpiperazin-1-yl)-1-(quinoline-8-sulfonyl)-2,3-dihydro-1H-indol-2-one

ESI-MS: $[M+H]^+$=649.25, 325.10;

EXAMPLE 47

(±)-5-Cyano-3-(2-ethoxy-5-methoxyphenyl)-1-(5-methylpyridine-2-sulfonyl)-3-(4-pyridin-4-ylpiperazin-1-yl)-2,3-dihydro-1H-indol-2-one ESI-MS: $[M+H]^+$=625.35;
$^1$H-NMR (500 MHz, DMSO) δ (ppm): 8.46 (1H, s), 8.21-8.12 (3H, m), 7.97 (2H, d), 7.91 (1H, d), 7.46 (2H, s), 6.88 (2H, s), 6.73 (2H, d), 3.89-3.56 [7H, m incl, 3.78 (3H, s), 3.70 (1H, quint.), 3.60 (1H, quint.)], 3.07-2.73 (3H, m br.), 2.30 (3H, s), 2.26-2.15 (2H, m br.), 1.84 (1H, s br.), 0.92 (3H, t).

EXAMPLE 48

(±)-5-Cyano-1-(5-chloroquinoline-8-sulfonyl)-3-(2-ethoxy-5-methoxyphenyl)-3-(4-pyridin-4-ylpiperazin-1-yl)-2,3-dihydro-1H-indol-2-one

ESI-MS: $[M+H]^+$=695.40;

EXAMPLE 49

(±)-5-Cyano-3-(2-ethoxy-4-fluorophenyl)-1-(5-methylpyridine-2-sulfonyl)-3-(4-pyridin-4-ylpiperazin-1-yl)-2,3-dihydro-1H-indol-2-one ESI-MS: $[M+H]^+$=613.15;
$^1$H-NMR (500 MHz, CDCl$_3$) δ (ppm): 8.35 (1H, s), 8.25 (2H, d), 8.21 (1H, d), 8.13 (1H, d), 7.82 (1H, t), 7.76 (1H, d), 7.67 (1H, d), 7.15 (1H, s), 6.77 (1H, m sym.), 6.56 (2H, d), 6.52 (1H, d), 3.89 (1H, quint.), 3.76 (1H, quint.), 3.58-3.40 (2H, m br.), 3.20-2.61 (3H, m br.), 2.43-2.30 [5H, m incl, 2.36 (3H, s)], 2.13-1.95 (1H, m br.), 1.11 (3H, t).

EXAMPLE 50

(±)-5-Cyano-3-(2,5-dimethoxyphenyl)-1-(4-methylquinoline-8-sulfonyl)-3-(4-pyridin-4-yl-piperazin-1-yl)-2,3-dihydro-1H-indol-2-one

ESI-MS: $[M+H]^+$=661.15;

EXAMPLE 51

(±)-5-Cyano-3-(2-methoxy-5-methylphenyl)-3-(4-pyridin-4-ylpiperazin-1-yl)-1-quinoline-8-sulfonyl)-2,3-dihydro-1H-indol-2-one

ESI-MS: $[M+H]^+$=631.15;

EXAMPLE 52

(±)-5-Cyano-3-(2-ethoxy-5-methoxyphenyl)-1-(5-methylpyridine-2-sulfonyl)-3-[4-(2-methylpyridin-4-yl)piperazin-1-yl]-2,3-dihydro-1H-indol-2-one ESI-MS: $[M+H]^+$=639.25;
$^1$H-NMR (500 MHz, CDCl$_3$) δ (ppm): 8.36 (1H, s), 8.21 (1H, d), 8.17-8.08 (2H, m), 7.74 (1H, d), 7.65 (1H, d), 7.45 (1H, s), 7.20 (1H, s), 6.80 (1H, d), 6.71 (1H, d), 6.44 (1H, s), 6.40 (1H, d), 6.40 (1H, d), 3.88-3.75 (4H, m), 3.69 (1H, quint.), 3.57-2.76 (m br.), 2.57-2.28 [m incl, 2.43 (2H, s), 2.35 (3H, s)], 1.06 (3H, t).

EXAMPLE 53

(±)-5-Cyano-1-(5-chloroquinoline-8-sulfonyl)-3-(2-ethoxy-5-methoxyphenyl)-3-[4-(2-methylpyridin-4-yl)piperazin-1-yl]-2,3-dihydro-1H-indol-2-one

ESI-MS: 709.15;

EXAMPLE 54

(±)-5-Cyano-3-(2-ethoxy-5-methoxyphenyl)-3-[4-(2-methylpyridin-4-yl)piperazin-1-yl]-1-(quinoline-8-sulfonyl)-2,3-dihydro-1H-indol-2-one

ESI-MS: $[M+H]^+$=675.25;

EXAMPLE 55

(±)-5-Cyano-3-(2,6-difluoropyridin-3-yl)-1-(2,4-dimethoxybenzenesulfonyl)-3-(4-pyridin-4-ylpiperazin-1-yl)-2,3-dihydro-1H-indol-2-one

EXAMPLE 56

(±)-5-Cyano-3-(2-ethoxyphenyl)-3-[4-(2-ethylpyridin-4-yl)piperazin-1-yl]-1-(quinoline-8-sulfonyl)-2,3-dihydro-1H-indol-2-one ESI-MS: $[M+H]^+$=659.70;
$^1$H-NMR (500 MHz, CDCl$_3$) δ (ppm): 8.78 (1H, d), 8.65 (1H, s), 8.44 (1H, d), 8.21 (1H, d), 8.13 (1H, d), 8.10 (1H, d), 7.77 (1H, d), 7.71 (2H, t), 7.46 (1H, m), 7.14 (1H, s), 7.00 (1H, t), 6.76 (1H, d), 6.27 (1H, s), 6.20 (1H, s), 3.82 (1H, quint.), 3.63 (1H, quint.), 3.55-3.33 (m br.), 3.12-2.57 [m br, incl, 2.87 (2H, q), 2.68 (2H, q)], 2.31-1.88 (m br.), 1.25 (3H, t), 1.06 (3H, t).

EXAMPLE 57

(±)-5-Cyano-3-(2-ethoxy-5-methoxyphenyl)-3-[4-(2-isopropylpyridin-4-yl)piperazin-1-yl]-1-(quinoline-8-sulfonyl)-2,3-dihydro-1H-indol-2-one ESI-MS: $[M+H]^+$=703.80;
$^1$H-NMR (500 MHz, CDCl$_3$) δ (ppm): 8.80 (1H, d), 8.68 (1H, s), 8.44 (1H, d), 8.21 (1H, d), 8.15 (1H, d), 8.09 (1H, d), 7.71 (2H, m), 7.46 (1H, m), 7.36 (1H, s), 7.16 (1H, s), 6.76

(1H, d), 6.67 (1H, d), 6.28 (1H, s), 6.20 (1H, s), 3.85-3.66 (4H, m br.), 3.63-3.36 [m br, incl, 3.54 (1H, quint.)], 3.16-1.89 [m br, incl, 2.88 (2H, m)], 1.38-0.91 [m incl. 1.24 (6H, d)], 1.00 (3H, t).

EXAMPLE 58

(±)-5-Cyano-3-(2-ethoxy-5-methoxyphenyl)-3-[4-(2-ethylpyridin-4-yl)piperazin-1-yl]-1-(quinoline-8-sulfonyl)-2,3-dihydro-1H-indol-2-one

ESI-MS: [M+H]$^+$=703.80;

EXAMPLE 59

(±)-3-(2,5-Dimethoxyphenyl)-5-methoxy-3-(4-pyridin-4-ylpiperazin-1-yl)-1-(quinoline-8-sulfonyl)-1,3-dihydroindol-2-one

ESI-MS: [M+H]$^+$=652.50, 326.90.

EXAMPLE 60

(+)-5-Cyano-3-(2-ethoxyphenyl)-3-(4-pyridin-4-ylpiperazin-1-yl)-1-(quinolin-8-sulfonyl)-2,3-dihydro-1H-indol-2-one ESI-MS: [M+H]$^+$=631.15;
$^1$H-NMR (500 MHz, CDCl$_3$) δ (ppm): 8.80 (1H, d), 8.68 (1H, s), 8.46 (1H, d), 8.29-8.16 (3H, m), 8.10 (1H, d), 7.83-7.69 (3H, m), 7.53-7.46 (1H, m), 7.31 (m+CHCl$_3$), 7.14 (3H, m), 7.02 (1H, t), 6.76 (1H, d), 6.35 (2H, d), 3.83 (1H, quint.), 3.64 (1H, quint.), 3.20-2.57 (m br.), 2.30-1.77 (m br.+H$_2$O), 1.03 (3H, t).
α (20° C., c=1 mg/ml, CHCl$_3$, l=1 dm): +121°;

EXAMPLE 61

(+)-5-Cyano-3-(2-ethoxyphenyl)-1-(5-methylpyridine-2-sulfonyl)-3-(4-pyridin-4-yl-piperazin-1-yl)-2,3-dihydro-1H-indol-2-one ESI-MS: [M+H$^+$]=595.25;
$^1$H-NMR (500 MHz, CDCl$_3$) δ (ppm): 8.37 (1H, s), 8.30-8.18 (3H, m), 8.13 (1H, m), 7.84 (1H, d), 7.75 (1H, d), 7.65 (1H, d), 7.27 (1H, d), 7.05 (1H, m), 6.78 (1H, m), 6.56 (2H, m br.), 3.90 (1H, m), 3.78 (1H, m), 3.72-3,41 (m br.), 3.24-2.81 (m br.), 2.64-2.30 (m br.), 1.10 (3H, s br.).
α (20° C., c=1 mg/ml, CHCl$_3$, l=1 dm): +119°;

EXAMPLE 62

(±)-5-Cyano-3-(2-ethoxy-5-methoxyphenyl)-3-[4-(2-methylpyridin-4-yl)-[1,4]diazepan-1-yl]-1-(quinoline-8-sulfonyl)-2,3-dihydro-1H-indol-2-one

ESI-MS: [M+H]$^+$=689.25;

EXAMPLE 63

(+)-5-Cyano-3-(2-ethoxyphenyl)-1-(4-methylquinoline-8-sulfonyl)-3-(4-pyridin-4-yl-piperazin-1-yl)-2,3-dihydro-1H-indol-2-one ESI-MS: [M+H]$^+$+=645.25;
$^1$H-NMR (500 MHz, CDCl$_3$) δ (ppm): 8.78 (1H, d), 8.50 (1H, s), 8.43 (1H, d), 8.28 (1H, d), 8.19 (1H, d), 7.80-7.68 (3H, m), 7.28 (1H, d), 7.26 (m+CHCl$_3$), 7.14 (1H, s), 7.01 (1H, t), 6.76 (1H, d), 6.36 (2H, d), 3.82 (1H, quint.), 3.63 (1H, quint.), 3.54-3.35 (m br.), 3.11-2.82 (m br.), 2.71 (3H, s), 2.35-1.93 (m br.), 1.03 (3H, t).
α (20° C., c=1 mg/ml, CHCl$_3$, l=1 dm): +80°;

EXAMPLE 64

(+)-5-Cyano-3-(2-ethoxyphenyl)-1-(5-methoxypyridine-2-sulfonyl)-3-(4-pyridin-4-yl-piperazin-1-yl)-2,3-dihydro-1H-indol-2-one ESI-MS: [M+H$^+$]=611.20;
α (20° C., c=1 mg/ml, CHCl$_3$, l=1 dm): +90°;

EXAMPLE 65

(±)-5-Cyano-3-(2-ethoxy-5-methoxyphenyl)-1-(5-methoxypyridine-2-sulfonyl)-3-[4-(2-methylpyridin-4-yl)-[1,4]diazepan-1-yl]-2,3-dihydro-1H-indol-2-one

ESI-MS: [M+H$^+$]=669.25;

EXAMPLE 66

(±)-5-Cyano-3-[4-(2-cyclopropylpyridin-4-yl)piperazin-1-yl]-3-(2-ethoxy-5-methoxyphenyl)-1-(quinoline-8-sulfonyl)-2,3-dihydro-1H-indol-2-one ESI-MS: [M+H]$^+$=701.25;
$^1$H-NMR (500 MHz, CDCl$_3$) δ (ppm): 8.80 (1H, d), 8.68 (1H, s), 8.45 (1H, d), 8.21 (1H d), 8.04 (2H, t), 7.71 (2H, m), 7.46 (1H, m), 7.39 (1H, s), 7.15 (1H, s), 6.78 (1H, m), 6.69 (1H, d), 6.25 (1H, s), 6.14 (1H, s), 3.77 (4H, s), 3.58 (1H, quint.), 3.46 (1H, s br.), 3.14 (4H, m br.), 2.31-1.76 (3H, m br.), 1.08-0.82 (7H, m).

EXAMPLE 67

(+)-5-Cyano-3-(2-ethoxyphenyl)-1-(5-ethoxyquinoline-8-sulfonyl)-3-(4-pyridin-4-yl-piperazin-1-yl)-2,3-dihydro-1H-indol-2-one ESI-MS: [M+H]$^+$=675.30;
$^1$H-NMR (500 MHz, CDCl$_3$) δ (ppm): 8.71 (1H, d), 8.66-8.60 (2H, m), 8.43 (1H, d), 8.20 (2H, m), 7.77 (1H, d), 7.71 (1H, d), 7.41 (1H, m), 7.24 (m+CHCl$_3$), 7.13 (1H, s), 7.02 (1H, t), 6.92 (1H, d), 6.77 (1H, d), 6.35 (1H, d), 4.30 (2H, q), 3.82 (1H, quint.), 3.65 (1H, quint.), 3.50 (1H, s br.), 3.11-2.57 (m br.), 2.36-1.85 (m br.), 1.57 (3H, t), 1.08 (3H, t), 1.08 (3H, t).
α (20° C., c=1 mg/ml, CHCl$_3$, l=1 dm): +72°;

EXAMPLE 68

(±)-5-Cyano-3-(2-ethoxy-5-methoxyphenyl)-1-(5-methoxypyridine-2-sulfonyl)-3-(5-pyridin-4-yl-hexahydropyrrolo[3,4-c]pyrrol-2-yl)-2,3-dihydro-1H-indol-2-one

ESI-MS: [M+H]$^+$=667.25;

EXAMPLE 69

(±)-5-Cyano-3-(2-ethoxy-5-methoxyphenyl)-1-(5-methoxyquinoline-8-sulfonyl)-3-(4-piperidin-4-ylpiperazin-1-yl)-2,3-dihydro-1H-indol-2-one hydrochloride ESI-MS: [M+H]$^+$=697.30;
$^1$H-NMR (500 MHz, CH$_3$OD) δ (ppm): 8.83 (1H, d), 8.80 (1H, d), 8.73 (1H, d), 8.43 (1H, d), 7.86 (1H, d), 7.65 (1H, m), 7.37 (1H, s), 7.32-7.26 (2H, m), 6.86 (1H, d), 6.80 (1H, d), 4.20 (3H, s), 3.70 (3H, s), 3.51 (6H, m sym.), 3.35-3.25 (m+H$_2$0), 3.20 (1H, t), 3.13-3.00 (4H, m), 2.73 (1H, t), 2.40 (1H, d), 2.30 (2H, t), 1.92 (2H, quint.), 1,83 (1H, s br.), 0.83 (3H, t).

EXAMPLE 70

(±)-5-Cyano-3-[4-(2-cyclopropylpyridin-4-yl)piperazin-1-yl]-3-(2-ethoxy-5-methoxyphenyl)-1-(5-methoxyquinoline-8-sulfonyl)-2,3-dihydro-1H-indol-2-one ESI-MS: [M+H]$^+$=731.30;
$^1$H-NMR (500 MHz, CDCl$_3$) δ (ppm): 8.74 (1H, d), 8.64 (1H, d), 8.60 (1H, d), 8.07 (1H, d), 7.72 (1H, d), 7.42 (1H, m), 7.37 (1H, s), 7.16 (1H, s), 6.94 (1H, d), 6.78 (1H, d), 6.70 (1H, d), 6.24 (1H, s), 6.15 (1H, m), 4.07 (3H, s), 3.82-3.71 [4H, m incl. 3.78 (3H, s)], 3.58 (1H, quint.), 3.50 (1H, s br.), 3.41-2.81 (m br.), 2.64 (1H, s br.), 2.28 (m br.), 1.96 (1H, s br.), 1.88 (1H, m), 1.03 (3H, t), 0.99-0.87 (4H, m).

EXAMPLE 71

(±)-5-Cyano-3-(6-chloro-2-ethoxypyridin-3-yl)-1-(5-methoxyquinoline-8-sulfonyl)-3-(4-pyridin-4-yl-[1,4]diazepan-1-yl)-2,3-dihydro-1H-indol-2-one ESI-MS: [M+Na]$^+$=7321.20, 710.15;

EXAMPLE 72

(±)-5-Cyano-3-(2-ethoxy-5-methoxyphenyl)-3-[4-(2-ethylpyridin-4-yl)piperazin-1-yl]-1-(5-methoxyquinoline-8-sulfonyl)-2,3-dihydro-1H-indol-2-one

ESI-MS: [M+H]$^+$=719.25;

EXAMPLE 73

(±)-5-Cyano-3-(2-ethoxy-5-methoxyphenyl)-1-(5-methoxyquinoline-8-sulfonyl)-3-[4-(2-methylpyridin-4-yl)-[1,4]diazepan-1-yl]-2,3-dihydro-1H-indol-2-one

ESI-MS: [M+H]$^+$=719.25;

EXAMPLE 74

(±)-5-Cyano-3-(2-ethoxy-5-methoxyphenyl)-1-(5-methoxyquinoline-8-sulfonyl)-3-(5-pyridin-4-yl-hexahydropyrrolo[3,4-c]pyrrol-2-yl)-2,3-dihydro-1H-indol-2-one

ESI-MS: [M+H$^+$]=717.25;

EXAMPLE 75

(−)-5-Cyano-3-(2-ethoxy-5-methoxyphenyl)-1-(5-methoxypyridine-2-sulfonyl)-3-[4-(2-methylpyridin-4-yl)piperazin-1-yl]-2,3-dihydro-1H-indol-2-one ESI-MS: [M+H$^+$]=655.20;
$^1$H-NMR (500 MHz, CDCl$_3$) δ (ppm): 8.31 (1H, d), 8.22 (1H, s), 8.18-8.10 (2H, m), 7.66 (1H, d), 7.43 (1H, s), 7.32 (1H, d), 7.18 (1H, s), 6.81 (1H, d), 6.72 (1H, s), 6.38 (1H, m), 3.83-3.76 [7H, m incl. 3.83 (3H, s), 3.80 (3H, s)], 3.74-3.60 (2H, m incl. 3.70 (1H, quint.)], 3.48 (1H, s br.), 3.18 (1H, s br.), 2.99 (1H, s br.), 2.83 (1H, s br.), 2.45 (3H, s), 1.91 (3H, s br.), 1.08 (3H, t).
α (20° C., c=1 mg/ml, CHCl$_3$, I=1 dm): −62°;

EXAMPLE 76

(+)-5-Cyano-3-(2-ethoxy-5-methoxyphenyl)-1-(5-methylpyridine-2-sulfonyl)-3-[4-(2-methylpyridin-4-yl)-piperazin-1-yl]-2,3-dihydro-1H-indol-2-one ESI-MS: [M+H]$^+$=639.20;
$^1$H-NMR (500 MHz, CDCl$_3$) δ (ppm): 8.37 (1H, s), 8.23 (1H, d), 8.16 (1H, d), 8.13 (1H, d), 7.76 (1H, d), 7.66 (1H, d), 7.46 (1H, s), 7.20 (1H, s), 6.82 (1H, d), 6.73 (1H, d), 6.45 (1H, s), 6.40 (1H, d), 3.83-3.79 [4H, m incl. 3.88 (3H, s)], 3.74-3.59 (2H, m incl. 3.70 (1H, quint.)], 3.59-3.44 (1H, s br.), 3.23-2.77 (m br.), 2.48 (3H, s), 2.45-2.30 [5H, m incl. 2.39 (3H, s)], 2.01 (2H, s br.), 1.07 (3H, t).
α (20° C., c=1 mg/ml, CHCl$_3$, I=1 dm): +117°.

EXAMPLE 77

(+)-5-Cyano-3-(2-ethoxy-5-methoxyphenyl)-3-[4-(4-methylpiperazin-1-yl)piperidin-1-yl]-1-(4-methylquinoline-8-sulfonyl)-2,3-dihydro-1H-indol-2-one ESI-MS: [M+H]$^+$=695.30;
$^1$H-NMR (500 MHz, CDCl$_3$) δ (ppm): 8.80 (1H, d), 8.50 (1H, s), 8.42 (1H, d), 8.33 (1 H, d), 7.76 (1H, t), 7.69 (1 H, d), 7.33 (1H, s), 7.25 (1H, s), 7.08 (1H, s), 6.73 (1H, d), 6.62 (1H, d), 3.77 (3H, s), 3.63 (1H, quint.), 3.45 (1H, quint.), 3.03 (1H, m br.), 2.73 (3H, s), 2.43 (8H, s br.), 2.26 (3H, s), 2.00 (1H, m br.), 1.92 (1H, t), 1.68-1.57 (2H, m br.), 1.38 (1H, q), 1.22-1.06 (2H, m br.), 0.90 (3H, t), 0.78 (1H, m br.).
α (20° C., c=1 mg/ml, CHCl$_3$, I=1 dm): +132°.

EXAMPLE 78

(±)-5-Cyano-3-(2-ethoxyphenyl)-1-(5-methoxypyridine-2-sulfonyl)-3-(4-pyridin-4-yl-[1,4]diazepan-1-yl)-2,3-dihydro-1H-indol-2-one ESI-MS: [M+H]$^+$=625.20;
$^1$H-NMR (500 MHz, CDCl$_3$) δ (ppm): 8.30-8.00 (5H, m), 7.77 (1H, m br.), 7.63 (1H, d), 7.33-7.20 (m+CHCl$_3$), 7.16 (1H, s), 7.03 (1H, t), 6.77 (1H, d), 6.38 (2H, d br.), 4.00-3.06 (9H, m br.), 2.54-1.85 (5H, m br.), 1.71-1.37 (1H, m br.), 1.18 (3H, t).

EXAMPLE 79

(±)-5-Cyano-3-(2-ethoxyphenyl)-1-(5-methoxypyridine-2-sulfonyl)-3-[4-(2-methyl-pyridin-4-yl)piperazin-1-yl]-2,3-dihydro-1H-indol-2-one ESI-MS: [M+H]$^+$=625.20;
$^1$H-NMR (500 MHz, CDCl$_3$) δ (ppm): 8.31 (1H, d), 8.22 (1H, s), 8.17-8.11 (2H, m), 7.82 (1H, d), 7.65 (1H, d), 7.35-7.24 (m+CHCl$_3$), 7.16 (1H, s), 7.06 (1H, t), 6.80 (1H, d), 6.46 (1H, s), 6.38 (1H, m sym.), 3.90 (1H, quint.), 3.84 (3H, s), 3.72 (1H, quint.), 3.72-2.80 (5H, m br.), 2.46 (3H, s), 2.36 (2H, m br.), 1.89 (s br.), 1.13 (3H, t).

EXAMPLE 80

(±)-5-Cyano-3-(2-ethoxy-5-methoxyphenyl)-1-(5-methoxyquinoline-8-sulfonyl)-3-(4-pyridin-4-ylpiperazin-1-yl)-2,3-dihydro-1H-indol-2-one ESI-MS: [M+H$^+$]=691.25;
$^1$H-NMR (500 MHz, CDCl$_3$) δ (ppm): 8.73 (1H, d), 8.65 (1H, s), 8.60 (1H, d), 8.44 (1H, d), 8.19 (2H, d), 7.72 (1H, d), 7.41 (1H, m), 7.37 (1H, s), 7.15 (1H, s), 6.94 (1H, d), 6.78 (1H, d), 6.70 (1H, d), 6.33 (2H, d), 4.06 (3H, s), 3.84-3.70 [4H, m incl. 3.79 (3H, s)], 3.60 (1H, quint.), 3.50 (1H, s br.), 3.15-2.57 (m br.), 2.37-1.67 (m br.), 1.05 (3H, t).

EXAMPLE 81

(±)-5-Cyano-3-(2-ethoxy-5-methoxyphenyl)-1-(5-fluoroquinoline-8-sulfonyl)-3-(4-pyridin-4-ylpiperazin-1-yl)-2,3-dihydro-1H-indol-2-one ESI-MS: [M+H]$^+$=679.25;
$^1$H-NMR (500 MHz, CDCl$_3$) δ (ppm): 8.80 (1H, t), 8.75 (1H, s), 8.49 (1H, d), 8.42 (1H, d), 8.21 (2H, d), 7.73 (1H, d), 7.54 (1H, m), 7.43-7.37 (2H, m), 7.18 (1H, s), 6.79 (1H, d), 6.70 (1H, d), 6.38 (2H, d), 3.86-3.69 [4H, m incl. 3.79 (3H, s)], 2.79-1.97 (m br.). 0.97 (3H, t).

EXAMPLE 82

(±)-5-Cyano-3-(2-ethoxy-5-methoxyphenyl)-1-(5-methoxypyridine-2-sulfonyl)-3-(4-pyridin-4-ylpiperazin-1-yl)-2,3-dihydro-1H-indol-2-one ESI-MS: [M+H]$^+$=641.25;
$^1$H-NMR (500 MHz, CDCl$_3$) δ (ppm): 8.30 (1H, d), 8.25 (2H, s), 8.22 (1H, s), 8.13 (1H, d), 7.65 (1H, d), 7.44 (1H, s), 7.31 (1H, d), 7.19 (1H, s), 6.81 (1H, d), 6.72 (1H, d), 6.54 (2H, d), 3.87-3.77 [7H, m incl. 3.83 (3H, s), 3.80 (3H, s)], 3.70 (1H, quint.), 3.53-2.75 (m br.), 2.36 (2H, s br.), 1.88 (1H, s br.), 1.08 (3H, t).

EXAMPLE 83

(±)-5-Cyano-3-(2-ethoxyphenyl)-1-(5-methoxypyridine-2-sulfonyl)-3-[4-(1-methyl-piperidin-4-yl)piperazin-1-yl]-2,3-dihydro-1H-indol-2-one ESI-MS: [M+H]$^+$=631.25;
$^1$H-NMR (500 MHz, CDCl$_3$) δ (ppm): 8.36-8.28 (2H, m), 8.10 (1H, d), 7.80 (1H, d), 7.60 (1H, d), 7.37 (1H, d), 7.30-7.20 (m+CHCl$_3$), 7.11 (1H, s), 7.03 (1H, t), 6.75 (1H, d), 3.96 (3H, s), 3.85 (1H, quint.), 3.73 (1H, quint.), 2.82-1.48 (m br.), 1.05 (3H, t).

EXAMPLE 84

(±)-5-Cyano-3-(2-ethoxyphenyl)-1-(4-ethylquinoline-8-sulfonyl)-3-(4-pyridin-4-yl-piperazin-1-yl)-2,3-dihydro-1H-indol-2-one ESI-MS: [M+H]$^+$=659.25;
$^1$H-NMR (500 MHz, CDCl$_3$) δ (ppm): 8.77 (1H, d), 8.54 (1H, s), 8.46 (1H, d), 8.32 (1H, d), 8.20 (2H, d), 7.79 (1H, d), 7.76-7.70 (2H, m), 7.30 (1H, s), 7.27-7.21 (m+CHCl$_3$), 7.13 (1H, s), 7.01 (1H, t), 6.75 (1H, d), 6.35 (2H, d), 3.82 (1H, quint.), 3.61 (1H, quint.), 3.43 (1H, s br.), 3.05 (3H, m sym.), 2.86 (2H, m br.), 2.61 (1H, s br.), 2.32-1.90 (m, br.), 1.34 (3H, t), 1.05 (3H, t).

EXAMPLE 85

(±)-5-Cyano-3-(6-chloro-2-ethoxypyridin-3-yl)-1-(5-methoxyquinoline-8-sulfonyl)-3-[4-(2-methylpyridin-4-yl)piperazin-1-yl]-2,3-dihydro-1H-indol-2-one ESI-MS: 710.15;
$^1$H-NMR (500 MHz, CDCl$_3$) δ (ppm): 8.72 (1H, d), 8.64 (1H, s), 8.60 (1H, d), 8.48 (1H, d), 8.11 (1H, d), 7.99 (1H, d), 7.76 (1H, d), 7.44 (1H, m), 7.10 (1H, s), 6.98 (2H, d), 6.30 (1H, s), 6.24 (1H, d), 4.10 (3H, s), 3.96 (1H, quint.), 3.80 (1H, quint.), 2.95 (2H, s br.), 2.43 (3H, s), 2.24 (2H, s br.), 2.02 (2H, s br.), 0.89 (3H, t).

EXAMPLE 86

(±)-5-Cyano-3-(2-ethoxy-5-methoxyphenyl)-1-(5-methoxypyridine-2-sulfonyl)-3-(4-piperazin-1-ylpiperidin-1-yl)-2,3-dihydro-1H-indol-2-one

ESI-MS: [M+H]$^+$=647.25;

EXAMPLE 87

(±)-5-Cyano-3-(2-ethoxy-5-methoxyphenyl)-1-(5-methoxyquinoline-8-sulfonyl)-3-(4-piperazin-1-ylpiperidin-1-yl)-2,3-dihydro-1H-indol-2-one hydrochloride

ESI-MS: [M+H]$^+$=697.25;

EXAMPLE 88

(±)-5-Cyano-3-(2-ethoxyphenyl)-1-(5-methylquinoline-8-sulfonyl)-3-(4-pyridin-4-yl-piperazin-1-yl)-2,3-dihydro-1H-indol-2-one ESI-MS: [M+H]$^+$=645.20;
$^1$H-NMR (500 MHz, CDCl$_3$) δ (ppm): 8.70-8.63 (2H, m), 8.45 (1H, d), 8.36 (1H, d), 8.20 (2H, d), 7.77 (1H, d), 7.72 (1H, d), 7.54 (1H, d), 7.48 (1H, m), 7.27-7.21 (m+CHCl$_3$), 7.13 (1H, s), 7.00 (1H, t), 6.77 (1H, d), 6.35 (2H, d), 3.84 (1H, quint.), 3.64 (1H, quint.), 3.54-2.55 [m br. incl. 2.72 (3H, s)], 2.31-1.92 (m br.), 1.05 (3H, t).

EXAMPLE 89

(±)-5-Cyano-3-(2-ethoxy-5-methoxyphenyl)-1-(5-methoxypyridine-2-sulfonyl)-3-[4-(1-methylpiperidin-4-yl)piperazin-1-yl]-2,3-dihydro-1H-indol-2-one ESI-MS: [M+H]$^+$=661.30;
$^1$H-NMR (500 MHz, CDCl$_3$) δ (ppm): 8.36-8.29 (2H, m), 8.11 (1H, d), 7.61 (1H, d), 7.42 (1H, s), 7.37 (1H, d), 7.15 (1H, s), 6.78 (1H, d), 6.68 (1H, d), 3.96 (3H, s), 3.83-3.73 [4H, m incl. 3.80 (3H, s)], 3.65 (1H, quint.), 3.09-1.51 [m br. incl. 2.94 (2H, d br.), 2.32 (3H, s), 1.58 (2H, quint. br.)], 1.02 (3H, t).

EXAMPLE 90

(±)-5-Cyano-3-[4-(2-cyclopropylpyridin-4-yl)piperazin-1-yl]-3-(2-ethoxy-5-methoxyphenyl)-1-(5-methoxypyridine-2-sulfonyl)-2,3-dihydro-1H-indol-2-one ESI-MS: [M+H]$^+$=681.20;
$^1$H-NMR (500 MHz, CDCl$_3$) δ (ppm): 8.31 (1H, d), 8.23 (1H, s), 8.15-8.07 (2H, m), 7.65 (1H, d), 7.43 (1H, s), 7.32 (1H, d), 7.20 (1H, s), 6.82 (1H, d), 6.73 (1H, s), 6.35 (1H, m), 3.89-3.78 [7H, m incl. 3.85 (3H, s), 3.83 (3H, s)], 3.74-3.59 [2H, m incl. 3.70 (1H, quint.)], 3.48 (1H, s br.), 3.18 (1H, s br.), 2.83 (1H, s br.), 2.35 (2H, s br.), 1.88 (2H, m sym.), 1.08 (3H, t), 1.02-0.87(4H, m),

EXAMPLE 91

(±)-5-Cyano-3-(2-ethoxy-5-methoxyphenyl)-3-[4-(2-isopropylpyridin-4-yl)piperazin-1-yl]-1-(5-methoxypyridine-2-sulfonyl)-2,3-dihydro-1H-indol-2-one ESI-MS: [M+H]$^+$=683.25;
$^1$H-NMR (500 MHz, CDCl$_3$) δ (ppm): 8.31 (1H, d), 8.24 (1H, s), 8.21 (1H, d), 8.13 (1H, d), 7.65 (1H, d), 7.45 (1H, s), 7.34 (1H, d), 7.20 (1H, s), 6.80 (1H, d), 6.72 (1H, d), 6.45 (1H, s), 6.40 (1H, m), 3.87-3.77 [7H, m incl. 3.84 (3H, s), 3.81 (3H, s)], 3.77-3.59 [2H, m incl. 3.69 (1H, quint.)], 3.50 (1H, s br.), 3.19 (1H, s br.), 3.05-2.77 (3H, m br.), 2.37 (2H, s br.), 2.16-1.80 (3H, m br.), 1.27 (3H, s), 1.25 (3H, s), 1.08 (3H, t).

EXAMPLE 92

(±)-5-Chloro-1-(4-methoxybenzenesulfonyl)-3-(2-methoxypyridin-3-yl)-3-(4-thiazol-2-yl-piperazin-1-yl)-1,3-dihydroindol-2-one

EXAMPLE 93

(±)-5-Chloro-1-(2,4-dimethoxybenzenesulfonyl)-3-(2-methoxypyridin-3-yl)-3-(4-thiazol-2-ylpiperazin-1-yl)-1,3-dihydroindol-2-one

EXAMPLE 94

(±)-5-Chloro-1-(2,4-dimethoxybenzenesulfonyl)-3-(2-methoxypyridin-3-yl)-3-(4-pyridin-4-ylpiperazin-1-yl)-1,3-dihydroindol-2-one

EXAMPLE 95

(±)-5-Chloro-1-(4-methoxybenzenesulfonyl)-3-(2-methoxypyridin-3-yl)-3-(4-pyridin-4-yl-piperazin-1-yl)-1,3-dihydroindol-2-one

EXAMPLE 96

(±)-5-Chloro-1-(2,4-dimethoxybenzenesulfonyl)-3-(2-methoxypyridin-3-yl)-3-[4-(4-cyanopyridin-2-yl)piperazin-1-yl]-1,3-dihydroindol-2-one

EXAMPLE 97

(±)-5-Chloro-1-(2-methoxy-4-methylbenzenesulfonyl)-3-(2-methoxypyridin-3-yl)-3-(4-pyridin-4-ylpiperazin-1-yl)-1, 3-dihydroindol-2-one

EXAMPLE 98

(±)-5-Chloro-1-(4-cyanobenzenesulfonyl)-3-(2-methoxypyridin-3-yl)-3-(4-pyridin-4-yl-piperazin-1-yl)-1,3-dihydroindol-2-one

EXAMPLE 99

(±)-5-Chloro-1-(2-methoxybenzenesulfonyl)-3-(2-methoxypyridin-3-yl)-3-(4-pyridin-4-yl-piperazin-1-yl)-1,3-dihydroindol-2-one

EXAMPLE 100

(±)-5-Chloro-1-(2,4-dimethoxybenzenesulfonyl)-3-[4-(4-methoxyphenyl)piperazin-1-yl]-3-(2-methoxypyridin-3-yl)-1,3-dihydroindol-2-one

EXAMPLE 101

(±)-5-Chloro-1-(2,4-dimethoxybenzenesulfonyl)-3-(2-methoxypyridin-3-yl)-3-(4-pyridin-2-ylpiperazin-1-yl)-1,3-dihydroindol-2-one

EXAMPLE 102

(±)-5-Chloro-1-(2-fluorobenzenesulfonyl)-3-(2-methoxypyridin-3-yl)-3-(4-pyridin-4-yl-piperazin-1-yl)-1,3-dihydroindol-2-one

EXAMPLE 103

(±)-5-Chloro-1-(4-fluorobenzenesulfonyl)-3-(2-methoxypyridin-3-yl)-3-(4-pyridin-4-yl-piperazin-1-yl)-1,3-dihydroindol-2-one

EXAMPLE 104

(±)-5-Chloro-1-(3,4-dimethoxybenzenesulfonyl)-3-(2-methoxypyridin-3-yl)-3-(4-pyridin-2-ylpiperazin-1-yl)-,3-dihydroindol-2-one

EXAMPLE 105

(±)-5-Chloro-3-(benzofuran-7-yl)-3-(4-pyridin-4-ylpiperazin-1-yl)-1-(quinoline-8-sulfonyl)-1,3-dihydroindol-2-one

EXAMPLE 106

(±)-5-Chloro-3-(3,4-dimethoxyphenyl)-3-(4-pyridin-4-ylpiperazin-1-yl)-1-(quinoline-8-sulfonyl)-1,3-dihydroindol-2-one as trifluoroacetic acid addition salt

EXAMPLE 107

(±)-5-Chloro-3-(3-dimethylaminomethylphenyl)-3-(4-pyridin-4-ylpiperazin-1-yl)-1-1-(quinoline-8-sulfonyl)-1,3-dihydroindol-2-one

EXAMPLE 108

(±)-5-Chloro-3-(2-methoxymethylphenyl)-3-(4-pyridin-4-ylpiperazin-1-yl)-1-quinoline-8-sulfonyl)-1,3-dihydroindol-2-one

EXAMPLE 109

(±)-5-Cyano-3-(2-ethoxyphenyl)-3-[4-(2-ethoxypyridin-4-yl)piperazin-1-yl]-1-(quinoline-8-sulfonyl)-1,3-dihydroindol-2-one

EXAMPLE 110

(±)-5-Cyano-3-(2-ethoxyphenyl)-3-[4-(2-chloropyridin-4-yl)piperazin-1-yl]-1-(quinoline-8-sulfonyl)-1,3-dihydroindol-2-one

EXAMPLE 111

(±)-5-Cyano-3-(2-ethoxyphenyl)-3-[4-(1-oxidopyridin-4-yl)piperazin-1-yl]-1-(quinoline-8-sulfonyl)-1,3-dihydroindol-2-one

EXAMPLE 112

(±)-5-Cyano-3-(2-ethoxyphenyl)-3-(4-[1,3,5]triazin-2-ylpiperazin-1-yl)-1-(quinoline-8-sulfonyl)-1,3-dihydroindol-2-one

EXAMPLE 113

(±)-5-Cyano-3-(2-ethoxyphenyl)-3-(4-pyrimidin-4-ylpiperazin-1-yl)-1-(quinoline-8-sulfonyl)-1,3-dihydroindol-2-one

EXAMPLE 114

(±)-5-Cyano-3-(2-ethoxyphenyl)-3-((1S,4S)-5-pyridin-4-yl-2,5-diazabicyclo[2.2.1]hept-2-yl)-1-(quinoline-8-sulfonyl)-1,3-dihydroindol-2-one

EXAMPLE 115

(±)-5-Chloro-3-(2-methoxyphenyl)-3-((1S,4S)-5-pyridin-4-yl-2,5-diazabicyclo[2.2.1]hept-2-yl)-1-(quinoline-8-sulfonyl)-1,3-dihydroindol-2-one

EXAMPLE 116

(±)-5-Cyano-3-(2-ethoxyphenyl)-1-(2-methylquinoline-8-sulfonyl)-3-(4-pyridin-4-piperazin-1-yl)-1,3-dihydroindol-2-one

EXAMPLE 117

(±)-5-Cyano-3-(2-ethoxyphenyl)-3-[4-(3-fluoropyridin-4-yl)piperazin-1-yl]-1-(quinoline-8-sulfonyl)-1,3-dihydroindol-2-one

EXAMPLE 118

(±)-5-Cyano-3-(2-ethoxyphenyl)-3-[4-(2-fluoropyridin-4-yl)piperazin-1-yl]-1-(quinoline-8-sulfonyl)-1,3-dihydroindol-2-one

EXAMPLE 119

(±)-5-Cyano-1-(2,5-dimethylthiophene-3-sulfonyl)-3-(2-ethoxyphenyl)-3-(4-pyridin-4-yl-piperazin-1-yl)-1,3-dihydroindol-2-one

EXAMPLE 120

(±)-5-Cyano-1-(thiophene-2-sulfonyl)-3-(2-ethoxyphenyl)-3-(4-pyridin-4-ylpiperazin-1-yl)-1,3-dihydroindol-2-one

EXAMPLE 121

(±)-5-Cyano-1-(5-chlorothiophene-2-sulfonyl)-3-(2-ethoxyphenyl)-3-(4-pyridin-4-yl-piperazin-1-yl)-1,3-dihydroindol-2-one

EXAMPLE 122

(±)-5-Cyano-1-(thiophene-3-sulfonyl)-3-(2-ethoxyphenyl)-3-(4-pyridin-4-ylpiperazin-1-yl)-1,3-dihydroindol-2-one

EXAMPLE 123

(±)-5-Cyano-3-(2-ethoxyphenyl)-1-(8-methoxyquinoline-5-sulfonyl)-3-(4-pyridin-4-yl-piperazin-1-yl)-1,3-dihydroindol-2-one

EXAMPLE 124

(±)-5-Cyano-3-(2-ethoxyphenyl)-3-(4-pyridin-4-ylpiperazin-1-yl)-1-(6-methylquinoline-8-sulfonyl)-1,3-dihydroindol-2-one

EXAMPLE 125

(±)-5-Cyano-3-(2-ethoxyphenyl)-3-(4-pyridin-4-ylpiperazin-1-yl)-1-(7-methylquinoline-8-sulfonyl)-1,3-dihydroindol-2-one

EXAMPLE 126

(±)-5-Furan-2-yl-3-(2-ethoxyphenyl)-3-(4-pyridin-4-ylpiperazin-1-yl)-1-(quinoline-8-sulfonyl)-1,3-dihydroindol-2-one

EXAMPLE 127

(±)-5-Furan-2-yl-3-(2-ethoxyphenyl)-1-(5-methylpyridine-2-sulfonyl)-3-(4-pyridin-4-yl-piperazin-1-yl)-1,3-dihydroindol-2-one

EXAMPLE 128

(±)-5-Cyano-3-(6-chloro-2-methoxypyridin-3-yl)-3-(4-pyridin-4-ylpiperazin-1-yl)-1-(2,4-dimethoxybenzenesulfonyl)-2,3-dihydro-1H-indol-2-one

EXAMPLE 129

(±)-5-Cyano-3-(2-ethoxy-5-methoxyphenyl)-1-(4-methylquinoline-8-sulfonyl)-3-((1S,4S)-5-pyridin-4-yl-2,5-diazabicyclo[2.2.1]hept-2-yl)-2,3-dihydro-1H-indol-2-one

EXAMPLE 130

(±)-5-Cyano-3-(2-ethoxy-5-methoxyphenyl)-1-(quinoline-8-sulfonyl)-3-((1S,4S)-5-pyridin-4-yl-2,5-diazabicyclo[2.2.1]hept-2-yl)-2,3-dihydro-1H-indol-2-one

EXAMPLE 131

(3R)-5-Cyano-3-(2-ethoxy-5-methoxyphenyl)-1-(quinoline-8-sulfonyl)-3-((1S,4S)-5-pyridin-4-yl-2,5-diazabicyclo[2.2.1]hept-2-yl)-2,3-dihydro-1H-indol-2-one

EXAMPLE 132

(±)-5-Cyano-3-(2-ethoxyphenyl)-1-(5-methylpyridine-2-sulfonyl)-3-(4-pyridin-4-yl-piperazin-1-yl)-2,3-dihydro-1H-indol-2-one as trifluoroacetic acid addition salt

EXAMPLE 133

(±)-5-Cyano-3-(2,6-dimethoxypyridin-3-yl)-3-(4-pyridin-4-ylpiperazin-1-yl)-1-(quinoline-8-sulfonyl)-1,3-dihydroindol-2-one

EXAMPLE 134

(±)-5-Cyano-3-(2,6-dimethoxypyridin-3-yl)-1-(2,4-dimethoxybenzenesulfonyl)-3-(4-pyridin-4-ylpiperazin-1-yl)-2,3-dihydro-1H-indol-2-one

EXAMPLE 135

(±)-5-Cyano-3-(6-chloro-2-ethoxypyridin-4-yl)-1-(5-methylpyridine-2-sulfonyl)-3-(4-pyridin-4-ylpiperazin-1-yl)-2,3-dihydro-1H-indol-2-one

EXAMPLE 136

(±)-5-Cyano-3-(6-chloro-2-ethoxypyridin-4-yl)-3-(4-pyridin-4-ylpiperazin-1-yl)-1-(quinoline-8-sulfonyl)-1,3-dihydroindol-2-one

EXAMPLE 137

(±)-5-Cyano-3-(2-ethoxyphenyl)-3-[4-(3,5-dichloro-pyridin-4-yl)piperazin-1-yl]-1(quinoline-8-sulfonyl)-2,3-dihydro-1H-indol-2-one

EXAMPLE 138

(±)-5-Cyano-3-(2,5-dimethoxyphenyl)-1-(5-methylpyridine-2-sulfonyl)-3-[4-(2-trifluoromethylpyridin-4-yl)piperazin-1-yl]-2,3-dihydro-1H-indol-2-one

EXAMPLE 139

(±)-5-Cyano-3-(2-ethoxyphenyl)-1-(5-methylpyridine-2-sulfonyl)-3-[4-(2-trifluoromethyl-pyridin-4-yl)piperazin-1-yl]-2,3-dihydro-1H-indol-2-one

EXAMPLE 140

(+)-5-Cyano-3-(2-ethoxy-5-methoxy-phenyl)-1-(5-methoxy-pyridine-2-sulfonyl)-3-(4-piperidin-4-yl-piperazin-1-yl)-2,3-dihydro-1H-indol-2-one ESI-MS: [M+H]$^+$=647.30
α (20° C., c=1 mg/ml, CHCl$_3$, I=1 dm): +111°

EXAMPLE 141

(+)-5-Cyano-3-(2-ethoxy-5-methoxy-phenyl)-1-(5-methoxy-pyridine-2-sulfonyl)-3-[4-(1-methyl-piperidin-4-yl)-piperazin-1-yl]-2,3-dihydro-1H-indol-2-one as trifluoroacetic acid addition salt

ESI-MS: [M+H]$^+$=661.25

EXAMPLE 142

(+)-5-Cyano-3-(2-ethoxy-4-methoxy-phenyl)-1-(5-methoxy-pyridine-2-sulfonyl)-3-(4-piperazin-1-yl-piperidin-1-yl)-2,3-dihydro-1H-indol-2-one

ESI-MS: [M+H]$^+$=647.30

EXAMPLE 143

(+)-5-Cyano-3-(2-ethoxy-5-methoxy-phenyl)-3-[4-(2-isopropyl-pyridin-4-yl)-piperazin-1-yl]-1-(5-methoxy-pyridine-2-sulfonyl)-2,3-dihydro-1H-indol-2-one as methylsulfonic acid addition salt α (20° C., c=1 mg/ml, CHCl$_3$, I=1 dm): +119°

EXAMPLE 144

(±)-5-Cyano-3-(2-ethoxy-4-fluoro-phenyl)-1-(5-methoxy-pyridine-2-sulfonyl)-3-[4-(2-methyl-pyridin-4-yl)-piperazin-1-yl]-2,3-dihydro-1H-indol-2-one

ESI-MS: [M+H]$^+$=643.10

EXAMPLE 145

(±)-5-Cyano-3-(2-ethoxy-5-methoxy-phenyl)-3-[4-(4-ethyl-piperazin-1-yl)-piperidin-1-yl]-1-(5-methoxy-pyridine-2-sulfonyl)-2,3-dihydro-1H-indol-2-one

ESI-MS: [M+H]$^+$=675.25

EXAMPLE 146

(±)-5-Cyano-3-(2-ethoxy-5-methoxy-phenyl)-3-[4-(2-ethyl-pyridin-4-yl)-piperazin-1-yl]-1-(5-methoxy-pyridine-2-sulfonyl)-2,3-dihydro-1H-indol-2-one

ESI-MS: [M+H]$^+$=669.25

Example147

(±)-5-Cyano-3-(2-ethoxy-4-fluoro-phenyl)-1-(5-methoxy-pyridine-2-sulfonyl)-3-(4-pyridin-4-yl-[1,4]diazepan-1-yl)-2,3-dihydro-1H-indol-2-one

ESI-MS: [M+H]$^+$=643.25

EXAMPLE 148

(±)-5-Cyano-3-(6-chloro-2-ethoxy-pyridin-3-yl)-1-(5-methoxy-pyridine-2-sulfonyl)-3-(5-pyridin-4-yl-hexahydro-pyrrolo[3,4-c]pyrrol-2-yl)-2,3-dihydro-1H-indol-2-one

ESI-MS:[M]$^+$=672.20

EXAMPLE 149

(±)-5-Cyano-3-(6-chloro-2-ethoxy-pyridin-3-yl)-1-(5-methoxy-pyridine-2-sulfonyl)-3-[5-(2-methyl-pyridin-4-yl)-hexahydro-pyrrolo[3,4-c]pyrrol-2-yl]-2,3-dihydro-1H-indol-2-one

[ESI-MS:[M]$^+$=686.15

EXAMPLE 150

(±)-5-Cyano-3-(2-ethoxy-phenyl)-3-[4-(2-isopropyl-pyridin-4-yl)-piperazin-1-yl]-1-(5-methoxy-pyridine-2-sulfonyl)-2,3-dihydro-1H-indol-2-one

ESI-MS: [M+H]$^+$=653.25

EXAMPLE 151

(+)-5-Cyano-3-(6-chloro-2-ethoxy-pyridin-3-yl)-1-(5-methoxy-pyridine-2-sulfonyl)-3-[4-(2-methyl-pyridin-4-yl)-piperazin-1-yl]-2,3-dihydro-1H-indol-2-one as methylsulfonic acid addition salt ESI-MS: [M]$^+$=660.15
α (20° C., c=1 mg/ml, CHCl$_3$, I=1 dm): +91°

EXAMPLE 152

(+)-5-Cyano-3-(6-chloro-2-ethoxy-pyridin-3-yl)-1-(5-methoxy-pyridine-2-sulfonyl)-3-[4-(2-methyl-pyridin-4-yl)-piperazin-1-yl]-2,3-dihydro-1H-indol-2-one ESI-MS: [M+H]$^+$=671.25
α (20° C., c=1 mg/ml, CHCl$_3$, I=1 dm): −82°

EXAMPLE 153

(±)-5-Cyano-3-(2-ethoxy-4-fluoro-phenyl)-3-[4-(2-isopropyl-pyridin-4-yl)-piperazin-1-yl]-1-(5-methoxy-pyridine-2-sulfonyl)-2,3-dihydro-1H-indol-2-one

ESI-MS: [M+H]$^+$=671.25

EXAMPLE 154

(±)-5-Cyano-3-(2-ethoxy-5-methoxy-phenyl)-3-[4-(2-isopropyl-pyridin-4-yl)-[1,4]diazepan-1-yl]-1-(5-methoxy-pyridine-2-sulfonyl)-2,3-dihydro-1H-indol-2-one

ESI-MS: [M+H]$^+$=697.25

EXAMPLE 155

(±)-5-Cyano-3-(6-chloro-2-ethoxy-pyridin-3-yl)-1-(5-methoxy-pyridine-2-sulfonyl)-3-((1S,4S)-5-pyridin-4-yl-2,5-diaza-bicyclo[2.2.1]hept-2-yl)-2,3-dihydro-1-2-one

ESI-MS: [M]$^+$=658.10

EXAMPLE 156

(+)-5-Cyano-3-(2-ethoxy-5-methoxy-phenyl)-1-(5-methoxy-pyridine-2-sulfonyl)-3-(4-piperazin-1-yl-piperidin-1-yl)-2,3-dihydro-1H-indol-2-one

ESI-MS: [M+H]$^+$=647.25

EXAMPLE 157

(±)-5-Cyano-3-(2-ethoxy-4-methoxy-phenyl)-3-(4-pyridin-4-yl-piperazin-1-yl)-1-(quinoline-8-sulfonyl)-2,3-dihydro-1H-indol-2-one

ESI-MS:[M+H]$^+$=661.20

EXAMPLE 158

(+)-5-Cyano-3-(2-ethoxy-5-methoxy-phenyl)-1-(5-methoxy-pyridine-2-sulfonyl)-3-[4-(4-methyl-piperazin-1-yl)-piperidin-1-yl]-2,3-dihydro-1H-indol-2-one ESI-MS: [M+H]$^+$662.25
α (20° C., c=1 mg/ml, CHCl$_3$, I=1 dm): +79°

EXAMPLE 159

(±)-5-Cyano-3-(2-ethoxy-5-methyl-phenyl)-1-(5-methoxy-quinoline-8-sulfonyl)-3-(4-pyridin-4-yl-piperazin-1-yl)-2,3-dihydro-1H-indol-2-one

ESI-MS: [M+H]$^+$=675.10

EXAMPLE 160

(±)-5-Cyano-3-(2-ethoxy-5-ethyl-phenyl)-1-(5-methoxy-quinoline-8-sulfonyl)-3-[4-(2-methyl-pyridin-4-yl)-piperazin-1-yl]-2,3-dihydro-1H-indol-2-one

ESI-MS: [M+H]$^+$=703.10

EXAMPLE 161

(±)-5-Cyano-3-(2-ethoxy-5-methoxy-phenyl)-1-(5-methoxy-quinoline-8-sulfonyl)-3-[4-(1-methyl-piperidin-4-yl)-piperazin-1-yl]-2,3-dihydro-1H-indol-2-one

ESI-MS: [M+H]$^+$=711.20

EXAMPLE 162

(+)-5-Cyano-3-(2-ethoxy-5-methoxy-phenyl)-1-(5-methoxy-quinoline-8-sulfonyl)-3-(4-pyridin-4-yl-piperazin-1-yl)-2,3-dihydro-1H-indol-2-one

ESI-MS: [M+H]$^+$=691.00

EXAMPLE 163

(+)-5-Cyano-3-(2-ethoxy-5-methoxy-phenyl)-1-(5-methoxy-pyridine-2-sulfonyl)-3-(4-pyridin-4-yl-piperazin-1-yl)-2,3-dihydro-1H-indol-2-one ESI-MS: [M+H]$^+$=641.25
α (20° C., c=1 mg/ml, CHCl$_3$, I=1 dm) : +105°

EXAMPLE 164

(+)-5-Cyano-3-(2-ethoxy-5-methoxy-phenyl)-1-(5-methoxy-pyridine-2-sulfonyl)-3-[4-(2-methyl-pyridin-4-yl)-piperazin-1-yl]-2,3-dihydro-1H-indol-2-one ESI-MS: [M+H]$^+$=655.25
α (20° C., c=1 mg/ml, CHCl$_3$, I=1 dm): +148°

EXAMPLE 165

(±)-5-Cyano-3-(2-ethoxy-5-ethyl-phenyl)-1-(5-methoxy-pyridine-2-sulfonyl)-3-[4-(2-methyl-pyridin-4-yl)-piperazin-1-yl]-2,3-dihydro-1H-indol-2-one

ESI-MS: [M+H]$^+$=653.25

EXAMPLE 166

(±)-5-Cyano-3-(2-ethoxy-5-ethyl-phenyl)-3-[4-(2-isopropyl-pyridin-4-yl)-piperazin-1-yl]-1-(5-methoxy-pyridine-2-sulfonyl)-2,3-dihydro-1H-indol-2-one

ESI-MS: [M+H]$^+$=681.25

EXAMPLE 167

(±)-5-Cyano-3-(6-chloro-2-ethoxy-pyridin-3-yl)-3-[4-(2-isopropyl-pyridin-4-yl)-piperazin-1-yl]-1-(5-methoxy-pyridine-2-sulfonyl)-2,3-dihydro-1H-indol-2-one

ESI-MS: [M+H]$^+$=689.20

EXAMPLE 168

(±)-5-Cyano-3-(6-chloro-2-ethoxy-pyridin-3-yl)-1-(5-methoxy-pyridine-2-sulfonyl)-3-(4-pyridin-4-yl-[1,4]diazepan-1-yl)-2,3-dihydro-1H-indol-2-one

ESI-MS: [M]$^+$=660.20

EXAMPLE 169

(±)-5-Cyano-3-(2-ethoxy-5-methyl-phenyl)-1-(5-methoxy-pyridine-2-sulfonyl)-3-(4-pyridin-4-yl-piperazin-1-yl)-2,3-dihydro-1H-indol-2-one

ESI-MS: [M+H]$^+$=625.20

EXAMPLE 170

(±)-5-Cyano-3-(6-chloro-2-ethoxy-pyridin-3-yl)-1-(5-methoxy-pyridine-2-sulfonyl)-3-[4-(4-methyl-piperazin-1-yl)-piperidin-1-yl]-2,3-dihydro-1H-indol-2-one

ESI-MS: [M+H]$^+$=666.20

EXAMPLE 171

(±)-5-Cyano-3-(2-ethoxy-4-methoxy-phenyl)-1-(5-methoxy-pyridine-2-sulfonyl)-3-[4-(4-methyl-piperazin-1-yl)-piperidin-1-yl]-2,3-dihydro-1H-indol-2-one

ESI-MS: [M+H]$^+$=661.20

EXAMPLE 172

(±)-5-Cyano-3-(2-ethoxy-5-methoxy-phenyl)-1-(5-methoxy-pyridine-2-sulfonyl)-3-(4-piperidin-4-yl-piperazin-1-yl)-2,3-dihydro-1H-indol-2-one as hydrochloride acid addition salt

ESI-MS: [M+H]$^+$647.20

EXAMPLE 173

(±)-5-Cyano-3-(2-ethoxy-3-methoxy-phenyl)-3-[4-(2-isopropyl-pyridin-4-yl)-piperazin-1-yl]-1-(5-methoxy-pyridine-2-sulfonyl)-2,3-dihydro-1H-indol-2-one as trifluoroacetic acid addition salt

ESI-MS: [M+H]$^+$=683.25

EXAMPLE 174

(±)-5-Cyano-3-(2-ethoxy-4-methoxy-phenyl)-1-(5-methoxy-pyridine-2-sulfonyl)-3-(4-piperazin-1-yl-piperidin-1-yl)-2,3-dihydro-1H-indol-2-one as bis (hydrochloride acid) addition salt

ESI-MS: [M+H]$^+$=647.20

EXAMPLE 175

(±)-5-Cyano-3-(2-ethoxy-4-methoxy-phenyl)-3-[4-(2-isopropyl-pyridin-4-yl)-piperazin-1-yl]-1-(5-methoxy-pyridine-2-sulfonyl)-2,3-dihydro-1H-indol-2-one

ESI-MS: [M+H]$^+$=683.20

EXAMPLE 176

(±)-5-Cyano-3-(6-chloro-2-ethoxy-pyridin-3-yl)-1-(5-methoxy-pyridine-2-sulfonyl)-3-(4-piperidin-4-yl-piperazin-1-yl)-2,3-dihydro-1H-indol-2-one as hydrochloride acid addition salt

ESI-MS:[M]$^+$=652.20

EXAMPLE 177

(±)-5-Cyano-3-(6-chloro-2-ethoxy-pyridin-3-yl)-1-(5-methoxy-pyridine-2-sulfonyl)-3-[4-(2-methyl-pyridin-4-yl)-[1,4]diazepan-1-yl]-2,3-dihydro-1H-indol-2-one as trifluoroacetic acid addition salt

ESI-MS: [M]$^+$=674.20

EXAMPLE 178

(±)-5-Cyano-3-(2-ethoxy-4-methoxy-phenyl)-1-(5-methoxy-pyridine-2-sulfonyl)-3-[4-(2-methyl-pyridin-4-yl)-piperazin-1-yl]-2,3-dihydro-1H-indol-2-one

ESI-MS: [M+H]$^+$=655.20

EXAMPLE 179

(±)-5-Cyano-3-(2-ethoxy-3-methoxy-phenyl)-1-(5-methoxy-pyridine-2-sulfonyl)-3-[4-(2-methyl-pyridin-4-yl)-piperazin-1-yl]-2,3-dihydro-1H-indol-2-one as trifluoroacetic acid addition salt

ESI-MS: [M+H]$^+$=655.25

EXAMPLE 180

(±)-5-Cyano-3-(2-ethoxy-5-methyl-phenyl)-1-(5-methoxy-pyridine-2-sulfonyl)-3-[4-(2-methyl-pyridin-4-yl)-piperazin-1-yl]-2,3-dihydro-1H-indol-2-one as trifluoroacetic acid addition salt

ESI-MS: [M+H]$^+$=639.20

EXAMPLE 181

(±)-5-Cyano-3-[4,4']bipiperidinyl-1-yl-3-(2-ethoxy-5-methoxy-phenyl)-1-(5-methoxy-pyridine-2-sulfonyl)-2,3-dihydro-1H-indol-2-one as bis(hydrochloride acid) addition salt

ESI-MS: $[M+H]^+=646.25$

EXAMPLE 182

(±)-5-Cyano-3-(6-chloro-2-ethoxy-pyridin-3-yl)-1-(5-methoxy-pyridine-2-sulfonyl)-3-(4-piperazin-1-yl-piperidin-1-yl)-2,3-dihydro-1H-indol-2-one as hydrochloride acid addition salt

ESI-MS: $[M]^+=652.20$

The compounds of the invention represent antagonists of the so-called receptors of the vasopressin/oxytocin family. Such compounds can be investigated in suitable assays which establish the affinity to a receptor, with the affinity constant Ki represening a measure of the potency of the compounds and a smaller value representing a larger potency. The compounds of the invention were tested in the following receptor binding assay for their affinity for the V1 b receptor.

Vasopressin V1 b Receptor Binding Assay:

Substances:

The test substances were dissolved in a concentration of $10^{-2}$ M in DMSO (dimethyl sulfoxide) and further diluted to $5\times10^{-4}$ M to $5\times10^{-9}$ M in DMSO. This series of DMSO predilutions was diluted 1:10 with assay buffer. The substance concentration was again diluted 1:5 in the assay mixture (2% DMSO in the mixture).

Membrane Preparation: CHO-K1 cells with stably expressed human vasopressin V1b receptor (clone 3H2) were harvested and homogenized in 50 mM Tris-HCl and in the presence of protease inhibitors (Roche complete Mini # 1836170) with a Polytron homogenizer at a medium setting for 2×10 seconds and subsequently centrifuged at 40 000×g for 1 h. The membrane pellet was again homogenized and centrifuged as described and then taken up in 50 mM Tris-HCl, pH 7.4, homogenized and stored in aliquots frozen in liquid nitrogen at −190° C.

Binding Assay:

The binding assay was carried out by a method based on that of Tahara et al. (Tahara A et al., Brit. J. Pharmacol. 125, 1463-1470 (1998)). The incubation buffer was: 50 mM Tris, 10 mM $MgCl_2$, 0.1% BSA, pH 7.4.

In the assay mixture (250 µl), membranes (50 µg/ml protein in incubation buffer) from CHO-K1 cells with stably expressed human V1b receptors (cell line hV1b__3H2_CHO) were incubated with 1.5 nM $^3$H-AVP (8-Arg-vasopressin, PerkinElmer #18479) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Bachem #H1780). All determinations were carried out as triplicate determinations. After incubation (60 minutes at room temperature), the free radioligand was removed by vacuum filtration (Skatron cell harvester 7000) through Whatman GF/B glass fiber filter mats, and the filters were transferred into scintillation vials. The liquid scintillation measurement took place in a Tricarb model 2000 or 2200CA instrument (Packard). Conversion of the measured cpm into dpm was carried out with the aid of a standard quench series.

Evaluation:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant human V1b receptors is 0.4 nM and was used to determine the Ki value.

The above assay was used to measure the affinities of the compounds of the invention for the human vasopressin V1 b receptor and to determine with affinity constants (Ki). The V1 b receptor affinity of selected compounds is detailed in Table I below (+++ means <10 nM, ++ means 10-50 nM)

In the case where the compounds of the invention have more than one stereogenic center, the stated affinities relate to the V1b receptor on the diastereomer which exhibits a stronger affinity (lower Ki value) for the V1 b receptor.

TABLE I

| Example | V1b Ki |
|---------|--------|
| 1 | +++ |
| 2 | ++ |
| 4 | ++ |
| 5 | +++ |
| 6 | +++ |
| 8 | ++ |
| 9 | ++ |
| 10 | +++ |
| 11 | ++ |
| 12 | ++ |
| 13 | +++ |
| 14 | ++ |
| 15 | ++ |
| 16 | +++ |
| 17 | ++ |
| 18 | +++ |
| 19 | ++ |
| 20 | ++ |
| 21 | ++ |
| 22 | +++ |
| 23 | ++ |
| 24 | +++ |
| 25 | +++ |
| 26 | ++ |
| 27 | ++ |
| 28 | ++ |
| 29 | ++ |
| 30 | ++ |
| 31 | ++ |
| 32 | +++ |
| 33 | +++ |
| 34 | +++ |
| 35 | +++ |
| 36 | +++ |
| 37 | +++ |
| 38 | ++ |
| 39 | ++ |
| 41 | ++ |
| 42 | ++ |
| 43 | ++ |
| 44 | ++ |
| 46 | ++ |
| 47 | +++ |
| 48 | ++ |
| 49 | ++ |
| 50 | ++ |
| 51 | +++ |
| 52 | ++ |
| 53 | ++ |
| 54 | +++ |
| 56 | ++ |
| 57 | +++ |
| 58 | +++ |
| 59 | +++ |
| 60 | +++ |
| 61 | +++ |
| 62 | +++ |
| 63 | +++ |

TABLE I-continued

| Example | V1b Ki |
|---|---|
| 64 | +++ |
| 65 | +++ |
| 66 | +++ |
| 67 | ++ |
| 68 | +++ |
| 69 | ++ |
| 70 | +++ |
| 71 | ++ |
| 72 | ++ |
| 73 | +++ |
| 74 | ++ |
| 78 | ++ |
| 79 | +++ |
| 80 | +++ |
| 81 | +++ |
| 82 | +++ |
| 83 | ++ |
| 84 | +++ |
| 85 | +++ |
| 86 | +++ |
| 87 | +++ |
| 88 | ++ |
| 140 | +++ |
| 141 | ++ |
| 142 | +++ |
| 143 | +++ |
| 144 | +++ |
| 145 | ++ |
| 146 | +++ |
| 147 | ++ |
| 148 | ++ |
| 149 | +++ |
| 150 | ++ |
| 151 | +++ |
| 152 | +++ |
| 153 | +++ |
| 154 | +++ |
| 155 | ++ |
| 156 | ++ |
| 157 | ++ |
| 158 | +++ |
| 159 | +++ |
| 160 | +++ |
| 161 | +++ |
| 162 | ++ |
| 163 | +++ |
| 164 | +++ |
| 165 | +++ |
| 166 | +++ |
| 167 | ++ |
| 168 | ++ |
| 169 | +++ |
| 170 | +++ |
| 171 | +++ |
| 172 | +++ |
| 173 | +++ |
| 174 | +++ |
| 175 | +++ |
| 176 | +++ |
| 177 | +++ |
| 178 | ++ |
| 179 | +++ |
| 180 | +++ |
| 181 | +++ |
| 182 | +++ |

In addition, the following assays can be used to determine the affinities for further vasopressin receptors or their subtypes such as, for example, V1a and V2, and the oxytocin (OT) receptor. The quotients, obtainable therein, of the corresponding Ki values, i.e. "Ki(V1a)/Ki(V1b)", "Ki(V2)/Ki(V1b)" and/or "Ki(OT)Ki(V1b)", can serve as a measure of a possible selectivity of the compounds of the invention in relation to a particular vasopressin or oxytocin receptor.

Vasopressin V1a Receptor Binding Assay:

Substances: The test substances were dissolved in a concentration of $10^{-2}$ M in DMSO. These DMSO solutions were further diluted in incubation buffer (50 mM Tris, 10 mM $MgCl_2$, 0.1% BSA, pH 7.4).

Membrane Preparation:

CHO-K1 cells with stably expressed human vasopressin V1a receptor (clone 5) were harvested and homogenized in 50 mM Tris-HCl and in the presence of protease inhibitors (Roche complete Mini #1836170) with a Polytron homogenizer at a medium setting for 2×10 seconds and subsequently centrifuged at 40 000×g for 1 h. The membrane pellet was again homogenized and centrifuged as described and then taken up in 50 mM Tris-HCl, pH 7.4, homogenized and stored in aliquots frozen in liquid nitrogen at −190° C.

Binding Assay:

The binding assay was carried out by a method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4. In the assay mixture (250 µl), membranes (20 µg/ml protein in incubation buffer) from CHO-K1 cells with stably expressed human V1a receptors (cell line hV1a_5_CHO) were incubated with 0.04 nM $^{125}$I-AVP (8-Arg-vasopressin, NEX 128) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Bachem #H1780). Triplicate determinations were carried out.

After incubation (60 minutes at room temperature), the free radioligand was removed by vacuum filtration (Skatron cell harvester 7000) through Whatman GF/B glass fiber filter mats, and the filters were transferred into scintillation vials. The liquid scintillation measurement took place in a Tricarb model 2000 or 2200CA instrument (Packard). Conversion of the measured cpm into dpm was carried out with the aid of a standard quench series.

Evaluation:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^{125}$I-AVP for the recombinant hV1a receptors was determined in saturation experiments. A Kd of 1.33 nM was used to determine the Ki value.

Vasopressin V2 Receptor Binding Assay:

Substances:

The test substances were dissolved in a concentration of $10^{-2}$ M in DMSO. These DMSO solutions were further diluted in incubation buffer (50 mM Tris, 10 mM $MgCl_2$, 0.1% BSA, pH 7.4).

Membrane Preparation:

CHO-K1 cells with stably expressed human vasopressin V2 receptor (clone 23) were harvested and homogenized in 50 mM Tris-HCl and in the presence of protease inhibitors (Roche complete Mini #1836170) with a Polytron homogenizer at a medium setting for 2×10 seconds and subsequently centrifuged at 40 000×g for 1 h. The membrane pellet was again homogenized and centrifuged as described and then taken up in 50 mM Tris-HCl, pH 7.4, homogenized and stored in aliquots frozen in liquid nitrogen at −190° C.

Binding Assay:

The binding assay was carried out by a method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4.

In the assay mixture (250 µl), membranes (50 µg/ml protein in incubation buffer) from CHO-K1 cells with stably expressed human V2 receptors (cell line hV2_23_CHO) were incubated with 1-2 nM $^3$H-AVP (8-Arg-vasopressin, PerkinElmer #18479) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Bachem #H1780). Triplicate determinations were carried out.

After incubation (60 minutes at room temperature), the free radioligand was removed by vacuum filtration (Skatron cell harvester 7000) through Whatman GF/B glass fiber filter mats, and the filters were transferred into scintillation vials. The liquid scintillation measurement took place in a Tricarb model 2000 or 2200CA instrument (Packard). Conversion of the measured cpm into dpm was carried out with the aid of a standard quench series.

Evaluation:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant hV2 receptors is 2.4 nM and was used to determine the Ki value.

Oxytocin Receptor Binding Assay

Substances:

The substances were dissolved in a concentration of $10^{-2}$ M in DMSO and diluted with incubation buffer (50 mM Tris, 10 mM $MgCl_2$, 0.1% BSA, pH 7.4).

Cell Preparation:

Confluent HEK-293 cells with transiently expressing recombinant human oxytocin receptors were centrifuged at 750×g and at room temperature for 5 minutes. The residue was taken up in ice-cold lysis buffer (50 mM Tris-HCl, 10% glycerol, pH7.4 and Roche Complete Protease Inhibitor) and subjected to an osmotic shock at 4° C. for 20 minutes. The lysed cells were then centrifuged at 750×g and at 4° C. for 20 minutes, and the residue was taken up in incubation buffer, and aliquots of $10^7$ cells/ml were prepared. The aliquots were frozen at −80° C. until used.

Binding Assay:

On the day of the experiment, the cells were thawed, diluted with incubation buffer and homogenized using a Multipette Combitip (Eppendorf, Hamburg). The reaction mixture of 0.250 ml was composed of 2 to 5×$10^4$ recombinant cells, 3-4 nM $^3$H-oxytocin (PerkinElmer, NET 858) in the presence of test substance (inhibition plot) or only incubation buffer (total binding). The nonspecific binding was determined with $10^{-6}$ M oxytocin (Bachem AG, H2510). Determinations in triplicate were set up. Bound and free radioligand were separated by filtration under vacuum with Whatmann GF/B glass fiber filters using a Skatron cell harvester 7000. The bound radioactivity was determined by liquid scintillation measurement in a Tricarb beta counter, model 2000 or 2200CA (Packard).

Evaluation:

The binding parameters were calculated by nonlinear regression (SAS), in analogy to the LIGAND program of Munson and Rodbard (Analytical Biochem 1980; 107: 220-239). The Kd of $^3$H-oxytocin for the recombinant hOT receptors is 7.6 nM and was used to determine the Ki value.

The metabolic stability of the compounds of the invention was determined in the following assay.

Determination of the Microsomal Half-Life:

The test substances are incubated in a concentration of 0.5 µM as follows:

0.5 µM test substance is preincubated together with liver microsomes of various species (0.25 mg of protein/ml) in 0.05M potassium phosphate buffer pH 7.4 in microtiter plates at 37° C. for 5 min. The reaction is started by adding NADPH (1 mg/mL). Aliquots are taken after 0, 5, 10, 15, 20 and 30 min, and the reaction is stopped with the same volume of acetonitrile and cooled down. The samples are frozen until analyzed. The half-life of the compound can be calculated, assuming first order kinetics, from the decrease in the concentration of the compound with time.

The invention claimed is:

1. A compound of the formula (I)

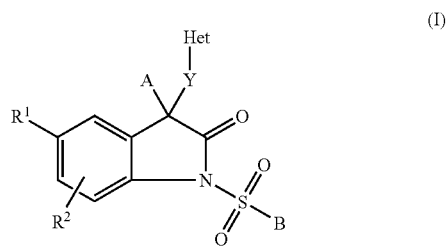

in which

A is 2-methoxyphenyl, 2-ethoxyphenyl, 2-ethoxy-5-methylphenyl, 2-ethoxy-5-ethylphenyl, 2-ethoxy-5-isopropylphenyl, 2-ethoxy-5-cyclopropylphenyl, 2-chlorophenyl, 2,3-dimethoxyphenyl, 2,4-dimethoxyphenyl, 2-ethoxy-4-fluorophenyl, 2,5-dimethoxyphenyl, 2-ethoxy-3-methoxyphenyl, 2-ethoxy-4-methoxyphenyl, 2-ethoxy-5-methoxyphenyl, 2-ethoxy-5-ethyl-phenyl, 2-isopropyloxy-5-methoxyphenyl, 2-methoxy-5-methylphenyl, 2-isobutyloxy-5-methoxyphenyl, 2-methoxy-5-(dimethylaminomethyl)phenyl, 2-methoxy-5-(methylaminomethyl)phenyl, 2-methoxypyridin-3-yl, 2-ethoxypyridin-3-yl, 2-ethoxy-5-methylpyridin-3-yl, 2-ethoxy-5-ethylpyridin-3-yl, 2-ethoxy-5-isopropylpyridin-3-yl, 2-ethoxy-5-cyclopropylpyridin-3-yl, 2-ethoxy-6-methoxypyridin-3-yl, 2-ethoxy-6-dimethylaminopyridin-3-yl, pyridin-2-yl, 3-methylpyridin-2-yl, 6-chloro-2-methoxypyridin-3-yl, 6-chloro-2-ethoxypyridin-3-yl or 2,6-difluoropyridin-3yl;

B is phenyl, pyridin-2-yl, quinolin-5-yl, quinolin-8-yl, or thienyl, where the aforementioned radicals are unsubstituted or have one, two, three or four substituents $R^B$ where $R^B$ is selected independently of one another from halogen, CN, $NO_2$, hydroxy, $C_1$-$C_6$-alkyl, $C_3$-$C_7$-cycloalkyl, $C_1$-$C_6$-haloalkyl, $C_1$-$C_6$-alkoxy, $C_1$-$C_6$-haloalkoxy, amino, $C_1$-$C_4$alkylamino, and di($C_1$-$C_4$-alkyl)amino, $R^1$ is hydrogen, halogen, CN, $NO_2$, $C_1$-$C_6$-alkyl, $C_1$-$C_6$-haloalkyl, $C_1$-$C_6$-alkoxy or $C_1C_6$-haloalkoxy, $R^2$ is hydrogen, halogen, CN, $NO_2$, $C_1$-$C_6$-alkyl, $C_1$-$C_6$-haloalkyl, $C_1$-$C_6$-alkoxy or $C_1$-$C_6$-haloalkoxy, Y is selected from the groups

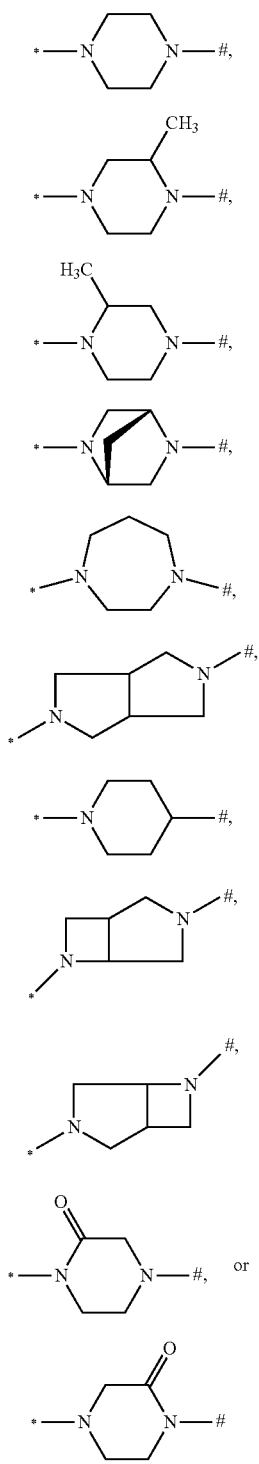

(Y.1)
(Y.2)
(Y.3)
(Y.4)
(Y.5)
(Y.6)
(Y.7)
(Y.8)
(Y.9)
(Y.10)
(Y.11)

in which
* is the linkage to the oxindole unit,
# is the linkage to the Het group,
and
Het is selected from a 2-pyridyl, 3-pyridyl, 4-pyridyl, 4-pyrimidinyl, 2-triazinyl, 1,3-thiazol-2-yl, piperidin-2-yl, piperidin-3-yl, piperidin-4-yl, piperazin-1-yl or piperazin-2-yl radical, where the radical is unsubstituted or has one, two or three identical or different substituents $R^{Het}$ which are selected independently of one another from halogen, CN, $NO_2$, $C_1$-$C_6$-alkyl, $C_3$-$C_7$-cycloalkyl, $C_1$-$C_6$-haloalkyl, $C_1$-$C_6$-alkyloxy, $C_1$-$C_6$-haloalkoxy, $C_3$-$C_7$-cycloalkoxy, di($C_1$-$C_6$-alkyl)amino, $C_1$-$C_6$-alkylthio, $C_1$-$C_6$-alkylsulfonyl, $C_2$-$C_6$-alkenyl, $C_2$-$C_6$-alkynyl, $C_2$-$C_6$-alkenyloxy and $C_2$-$C_6$-alkynyloxy, where the radical A is different from 2-methoxyphenyl, 2-ethoxyphenyl, 2-ethoxy-5-methylphenyl, 2-ethoxy-5-ethylphenyl, 2-ethoxy-5-isopropylphenyl, 2-ethoxy-5-cyclopropylphenyl, 2-chlorophenyl, 2,3-dimethoxyphenyl, 2,4-dimethoxyphenyl, 2-ethoxy-4-fluorophenyl, 2,5-dimethoxyphenyl, 2-ethoxy-3-methoxyphenyl, 2-ethoxy-4-methoxyphenyl, 2-ethoxy-5-methoxyphenyl, 2-ethoxy-5-ethyl-phenyl, 2-isopropyloxy-5-methoxyphenyl, 2-methoxy-5-methylphenyl 2-isobutyloxy-5-methoxyphenyl 2-methoxy-5-(dimethyl-aminomethyl)phenyl, and 2-methoxy-5-(methylaminomethyl)phenyl when the radical B is phenyl which is unsubstituted or has one, two, three or four substituents $R^B$, or a tautomeric, enantiomeric and/or diastereomeric form thereof, or a physiologically tolerated salt or N-oxide of said compound.

2. The compound of the formula (I) according to claim 1, in which A is 2-methoxy-phenyl, 2-ethoxyphenyl, 2,5-dimethoxyphenyl or 2-ethoxy-5-methoxyphenyl.

3. The compound of the formula (I) as claimed in claim 1, in which B is pyridin-2-yl or quinolin-8-yl which is unsubstituted or has one, two, three or four substituents $R^B$.

4. The compound of the formula (I) as claimed in claim 3, in which B is pyridin-2-yl or quinolin-8-yl which is unsubstituted or has a substituent $R^B$ in position 5.

5. The compound of the formula (I) as claimed in claim 3, in which B is pyridin-2-yl, 5-methylpyridin-2-yl, 5-methoxypyridin-2-yl, quinolin-8-yl, 3-methylquinolin-8-yl, 4-methylquinolin-8-yl, 5-methylquinolin-8-yl, 5-methoxyquinolin-8-yl, 4-ethyl-8-quinolinyl, 5-ethoxyquinolin-8-yl, 5-chloroquinolin-8-yl, or 5-fluoroquinolin-8-yl.

6. The compound of the formula (I) as claimed in claim 5, in which B is 5-methoxy-pyridin-2-yl, quinolin-8-yl or 5-methoxyquinolin-8-yl.

7. The compound of the formula (I) as claimed in claim 1, in which

B is phenyl and is unsubstituted or has one, two, three or four substituents $R^B$.

8. The compound of the formula (I) as claimed in claim 7, in which A is 6-chloro-2-ethoxypyridin-3-yl.

9. The compound of the formula (I) as claimed in claim 7, in which B is 2,3-dimethoxyphenyl, 2,4-dimethoxyphenyl, 3,5-dimethoxyphenyl, 2-ethoxy-4-methoxyphenyl, 4-amino-2-methoxyphenyl, 4-methoxy-2-nitrophenyl, or 2-trifluoromethyl-4-cyanophenyl.

10. The compound of the formula (I) as claimed in claim 9, in which B is 2,4-dimethoxyphenyl.

11. The compound of the formula (I) as claimed in claim 1, in which $R^1$ is CN, chlorine, methyl or methoxy.

12. The compound of the formula (I) as claimed in claim 1, in which $R^2$ is hydrogen.

13. The compound of the formula (I) as claimed in claim 1, in which Y is selected from the groups

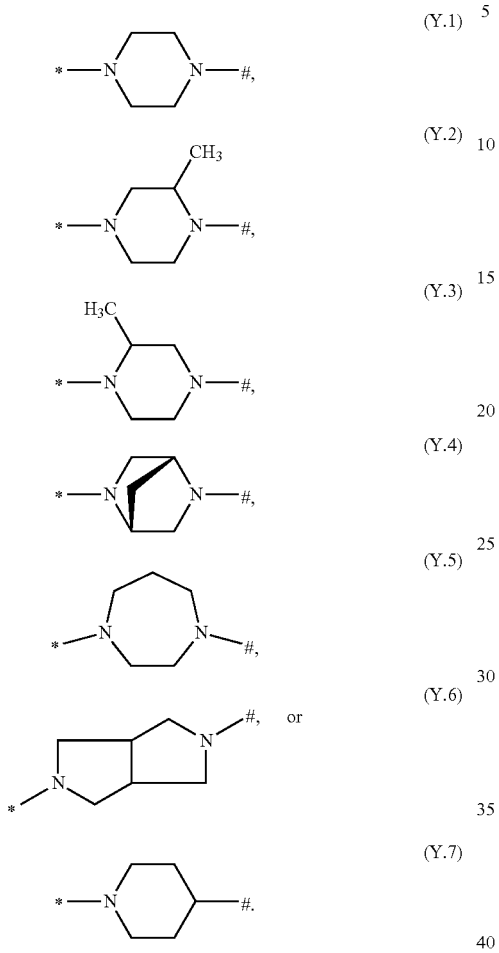

14. The compound of the formula (I) as claimed in claim 13, in which Y is piperazine-1,4-diyl, piperidine-1,4-diyl or homopiperazine-1,4-diyl.

15. The compound of the formula (I) as claimed in claim 1, in which

Het is selected from pyridin-4-yl, pyridin-3-yl, pyridin-2-yl, 2-methylpyridin-4-yl, 3-methylpyridin-4-yl, 3-ethylpyridin-4-yl, 3-cyclopropylpyridin-4-yl, 2-ethoxypyridin-4-yl, 2-fluoropyridin-4-yl, 2-chloropyridin-4-yl, 2-isopropylpyridin-4-yl, 3-isopropylpyridin-4-yl and 3-fluoropyridin-4-yl.

16. The compound of the formula (I) as claimed in claim 15, in which Het is pyridin-4-yl which is unsubstituted or has a substituent $R^{Het}$.

17. The compound of the formula (I) as claimed claim 1, in which

Het is a piperidin-2-yl, piperidin-3-yl, piperidin-4-yl, piperazin-1-yl or piperazin-2-yl radical which is unsubstituted or has one, two or three identical or different substituents $R^{Het}$ which are selected independently of one another from halogen, CN, $NO_2$, $C_1$-$C_6$-alkyl, $C_1$-$C_6$-haloalkyl, $C_1$-$C_6$-alkyloxy, $C_1$-$C_6$-haloalkoxy and $C_3$-$C_7$-cycloalkyl.

18. The compound of the formula (I) as claimed in claim 1, in which the group Y-Het is one of the following radicals:

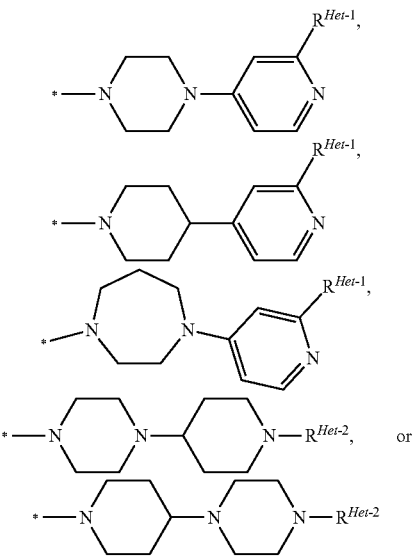

in which * indicates the linkage to the oxindole unit, $R^{Het-1}$ is hydrogen, methyl or isopropyl, and in which $R^{Het-2}$ is hydrogen or methyl.

19. A pharmaceutical composition comprising a compound according to claim 1 or pharmaceutically acceptable salt thereof, and a pharmaceutical carrier.

20. A compound according to claim 1, or a pharmaceutically acceptable salt thereof, wherein the compound is selected from the group consisting of 5-Chloro-3-(2,4-dimethoxyphenyl)-3-(4-pyridin-4-ylpiperazin-1-yl)-1-(quinoline-8-sulfonyl)-1,3-dihydroindol -2-one;

5-Chloro-3-(2,3-dimethoxyphenyl)-3-(4-pyridin-4-ylpiperazin-1-yl)-1-(quinoline-8-sulfonyl)-1,3-dihydroindol -2-one (hydrochloride);

5-Cyano-1-(2,4-dimethoxybenzenesulfonyl)-3-(2-ethoxypyridin-3-yl)-3-(4-pyridin-4-ylpiperazin-1-yl)-2,3-dihydro-1H-indol -2-one;

5-Cyano-3-(2-methoxypyridin-3-yl)-3-(4-pyridin-4-ylpiperazin-1-yl)-1-(quinoline-8-sulfonyl)-2,3-dihydro-1H-indol -2-one;

5-Cyano-3-(2-ethoxypyridin-3-yl)-3-(4-pyridin-4-ylpiperazin-1-yl)-1-(quinoline-8-sulfonyl)-2,3-dihydro-1H-indol -2-one;

5-Cyano-3-(2-ethoxyphenyl)-3-(2-methyl-4-pyridin-4-ylpiperazin-1-yl)-1-(quinoline-8-sulfonyl)-2,3-dihydro-1H-indol -2-one;

5-Cyano-3-(2-ethoxyphenyl)-1-(3-methylquinoline-8-sulfonyl)-3-(4-pyridin-4-yl-piperazin-1-yl)-2,3-dihydro-1H-indol -2-one;

5-Chloro-3-pyridin-2-yl-3-(4-pyridin-4-ylpiperazin-1-yl)-1-(quinoline-8-sulfonyl)-1,3-dihydroindol-2-one;

5-Chloro-3-(3-methylpyridin-2-yl)-3-(4-pyridin-4-ylpiperazin-1-yl)-1-(quinoline-8-sulfonyl)-1,3-dihydroindol -2-one;

5-Chloro-3-(6-chloro-2-methoxypyridin-3-yl)-3-(4-pyridin-4-ylpiperazin-1-yl)-1-(quinoline-8-sulfonyl)-1,3-dihydroindol -2-one;

5-Cyano-3-(2-ethoxyphenyl)-1-(5-methylpyridine-2-sulfonyl)-3-(4-pyridin-4-yl-piperazin-1-yl)-2,3-dihydro-1H-indol -2-one;

5-Cyano-1-(5-chloroquinoline-8-sulfonyl)-3-(2-ethoxyphenyl)-3-(4-pyridin-4-yl-piperazin-1-yl)-2,3-dihydro-1H-indol -2-one;
5-Cyano-3-(2-ethoxy-5-methoxyphenyl)-3-(4-pyridin-4-yl-piperazin-1-yl)-1-(quinoline-8-sulfonyl)-2,3-dihydro-1H-indol -2-one;
5-Cyano-3-(2-ethoxyphenyl)-1-(pyridine-2-sulfonyl)-3-(4-pyridin-4-yl-piperazin-1-yl)-2,3-dihydro-1H-indol-2-one;
5-Cyano-3-(2-ethoxyphenyl)-3-[4-(3-methylpyridin-4-yl)-piperazin-1-yl]-1-(quinoline-8-sulfonyl)-2,3-dihydro-1H-indol -2-one;
5-Cyano-3-(2-ethoxyphenyl)-1-(4-methylquinoline-8-sulfonyl)-3-(4-pyridin-4-yl-piperazin-1-yl)-2,3-dihydro-1H-indol -2-one;
5-Cyano-3-(2-ethoxyphenyl)-3-(3-methyl-4-pyridin-4-ylpiperazin-1-yl)-1-(quinoline-8-sulfonyl)-2,3-dihydro-1H-indol -2-one;
5-Cyano-3-(2-ethoxy-5-methoxyphenyl)-3-[4-(2-methylpyridin-4-yl)piperazin-1-yl]-1-(4-methylquinoline-8-sulfonyl)-2,3-dihydro-1H-indol-2-one;
5-Cyano-3-(6-chloro-2-methoxypyridin-3-yl)-3-(4-pyridin-4-ylpiperazin-1-yl)-1-(quinoline-8-sulfonyl)-2,3-dihydro-1H-indol -2-one;
5-Cyano-3-(2-ethoxy-5-methoxyphenyl)-1-(5-methylpyridine-2-sulfonyl)-3-((1S,4S)-5-pyridin-4-yl-2,5-diazabicyclo [2.2.1]hept-2-yl)-2,3-dihydro-1H-indol-2-one;
5-Cyano-3-(2-isopropoxy-5-methoxyphenyl)-1-(5-methylpyridine-2-sulfonyl)-3-(4-pyridin-4-ylpiperazin-1-yl)-2,3-dihydro-1H-indol -2-one;
5-Cyano-3-(2-ethoxyphenyl)-1-(5-methoxypyridine-2-sulfonyl)-3-(4-pyridin-4-yl-piperazin-1-yl)-2,3-dihydro-1H-indol -2-one;
5-Cyano-3-(6-chloro-2-ethoxypyridin-3-yl)-1-(5-methylpyridine-2-sulfonyl)-3-(4-pyridin-4-ylpiperazin-1-yl)-2,3-dihydro-1H-indol-2-one;
5-Cyano-3-(6-chloro-2-ethoxypyridin-3-yl)-3-(4-pyridin-4-ylpiperazin-1-yl)-1-(quinoline-8-sulfonyl)-2,3-dihydro-1H-indol -2-one;
5-Cyano-3-(2-ethoxyphenyl)-1-(5-methoxyquinoline-8-sulfonyl)-3-(4-pyridin-4-yl-piperazin-1-yl)-2,3-dihydro-1H-indol -2-one;
5-Cyano-3-(2-ethoxyphenyl)-1-(5-fluoroquinoline-8-sulfonyl)-3-(4-pyridin-4-yl-piperazin-1-yl)-2,3-dihydro-1H-indol -2-one;
5-Cyano-3-(6-chloro-2-ethoxypyridin-3-yl)-3-[4-(2-methylpyridin-4-yl)-piperazin-1-yl]-1-(quinoline-8-sulfonyl)-2,3-dihydro-1H-indol -2-one;
5-Cyano-3-(6-chloro-2-ethoxypyridin-3-yl)-1-(2,4-dimethoxybenzenesulfonyl)-3-[4-(2-methylpyridin-4-yl)piperazin-1-yl]-2,3-dihydro-1H-indol -2-one;
5-Cyano-3-(6-chloro-2-ethoxypyridin-3-yl)-1-(2,4-dimethoxybenzenesulfonyl)-3-(4-pyridin-4-ylpiperazin-1-yl)-2,3-dihydro-1H-indol-2-one;
5-Cyano-3-(6-chloro-2-ethoxypyridin-3-yl)-1-(4-methylquinoline-8-sulfonyl)-3-(4-pyridin-4-ylpiperazin-1-yl)-2,3-dihydro-1H-indol -2-one;
5-Cyano-3-(2-ethoxy-4-fluorophenyl)-1-(5-methoxyquinoline-8-sulfonyl)-3-(4-pyridin-4-ylpiperazin-1-yl)-2,3-dihydro-1H-indol -2-one;
5-Cyano-3-(2-ethoxy-4-fluorophenyl)-1-(5-methoxypyridine-2-sulfonyl)-3-(4-pyridin-4-ylpiperazin-1-yl)-2,3-dihydro-1H-indol-2-one;
5-Cyano-3-(2-ethoxy-5-methoxyphenyl)-1-(5-methoxyquinoline-8-sulfonyl)-3-[4-(2-methylpyridin-4-yl)piperazin-1-yl]-2,3-dihydro-1H-indol -2-one;
5-Cyano-3-(6-chloro-2-ethoxypyridin-3-yl)-1-(5-methoxypyridine-2-sulfonyl)-3-[4-(2-methylpyridin-4-yl)piperazin-1-yl]-2,3-dihydro-1H-indol -2-one;
5-Cyano-3-(2-ethoxy-5-methoxyphenyl)-1-(5-methoxypyridine-2-sulfonyl)-3-[4-(2-methylpyridin-4-yl)piperazin-1-yl]-2,3-dihydro-1H-indol -2-one;
5-Cyano-3-(6-chloro-2-ethoxypyridin-3-yl)-1-(5-methoxypyridine-2-sulfonyl)-3-(4-pyridin-4-ylpiperazin-1-yl)-2,3-dihydro-1H-indol-2-one;
5-Chloro-3-(2-methoxyphenyl)-3-(4-pyridin-4-ylpiperazin-1-yl)-1-(quinoline-8-sulfonyl)-1,3-dihydroindol-2-one;
5-Cyano-3-(2-ethoxyphenyl)-3-(4-pyridin-4-ylpiperazin-1-yl)-1-(quinoline-8-sulfonyl)-2,3-dihydro-1H-indol -2-one;
3-(2-Methoxyphenyl)-6-methyl-3-(4-pyridin-4-ylpiperazin-1-yl)-1-(quinoline-8-sulfonyl)-1,3-dihydroindol-2-one;
5-Chloro-3-(2-chlorophenyl)-3-(4-pyridin-4-ylpiperazin-1-yl)-1-(quinoline-8-sulfonyl)-1,3-dihydroindol-2-one;
5-Chloro-3-(5-dimethylaminomethyl-2-methoxyphenyl)-3-(4-pyridin-4-ylpiperazin-1-yl)-1-(quinoline-8-sulfonyl)-1,3-dihydroindol -2-one;
5-Chloro-3-(2-methoxypyridin-3-yl)-3-(4-pyridin-4-ylpiperazin-1-yl)-1-(quinoline-8-sulfonyl)-1,3-dihydroindol -2-one;
5-Cyano-3-(2-methoxyphenyl)-3-(4-pyridin-4-ylpiperazin-1-yl)-1-(quinoline-8-sulfonyl)-2,3-dihydro-1H-indol-2-one;
5-Cyano-3-(2-ethoxyphenyl)-3-[4-(2-methylpyridin-4-yl)piperazin-1-yl]-1-(quinoline-8-sulfonyl)-2,3-dihydro-1H-indol -2-one;
5-Chloro-3-(2-methoxy-5-methylaminomethylphenyl)-3-(4-pyridin-4-ylpiperazin-1-yl)-1-(quinoline-8-sulfonyl)-1,3-dihydroindol -2-one;
5-Cyano-3-(2-ethoxy-4-fluorophenyl)-3-(4-pyridin-4-ylpiperazin-1-yl)-1-(quinoline-8-sulfonyl)-2,3-dihydro-1H-indol -2-one;
5-Cyano-3-(2-ethoxy-5-methoxyphenyl)-1-(5-methylpyridine-2-sulfonyl)-3-(4-pyridin-4-ylpiperazin-1-yl)-2,3-dihydro-1H-indol-2-one;
5-Cyano-1-(5-chloroquinoline-8-sulfonyl)-3-(2-ethoxy-5-methoxyphenyl)-3-(4-pyridin-4-ylpiperazin-1-yl)-2,3-dihydro-1H-indol-2-one;
5-Cyano-3-(2-ethoxy-4-fluorophenyl)-1-(5-methylpyridine-2-sulfonyl)-3-(4-pyridin-4-ylpiperazin-1-yl)-2,3-dihydro-1H-indol-2-one;
5-Cyano-3-(2,5-dimethoxyphenyl)-1-(4-methylquinoline-8-sulfonyl)-3-(4-pyridin-4-yl-piperazin-1-yl)-2,3-dihydro-1H-indol -2-one;
5-Cyano-3-(2-methoxy-5-methylphenyl)-3-(4-pyridin-4-ylpiperazin-1-yl)-1-(quinoline-8-sulfonyl)-2,3-dihydro-1H-indol -2-one;
5-Cyano-3-(2-ethoxy-5-methoxyphenyl)-1-(5-methylpyridine-2-sulfonyl)-3-[4-(2-methylpyridin-4-yl)piperazin-1-yl]-2,3-dihydro-1H-indol -2-one;
5-Cyano-1-(5-chloroquinoline-8-sulfonyl)-3-(2-ethoxy-5-methoxyphenyl)-3-[4-(2-methylpyridin-4-yl)piperazin-1-yl]-2,3-dihydro-1H-indol -2-one;
5-Cyano-3-(2-ethoxy-5-methoxyphenyl)-3-[4-(2-methylpyridin-4-yl)piperazin-1-yl]-1-(quinoline-8-sulfonyl)-2,3-dihydro-1H-indol -2-one;
5-Cyano-3-(2,6-difluoropyridin-3-yl)-1-(2,4-dimethoxybenzenesulfonyl)-3-(4-pyridin-4-ylpiperazin-1-yl)-2,3-dihydro-1H-indol-2-one;

5-Cyano-3-(2-ethoxyphenyl)-3-[4-(2-ethylpyridin-4-yl) piperazin-1-yl]-1-(quinoline-8-sulfonyl)-2,3-dihydro-1H-indol -2-one;

5-Cyano-3-(2-ethoxy-5-methoxyphenyl)-3-[4-(2-isopropylpyridin-4-yl) piperazin-1-yl]-1-(quinoline-8-sulfonyl)-2,3-dihydro-1H-indol -2-one;

5-Cyano-3-(2-ethoxy-5-methoxyphenyl)-3-[4-(2-ethylpyridin-4-yl)piperazin-1-yl]-1-(quinoline-8-sulfonyl)-2,3-dihydro-1H-indol -2-one;

3-(2,5-Dimethoxyphenyl)-5-methoxy-3-(4-pyridin-4-ylpiperazin-1-yl)-1-(quinoline-8-sulfonyl)-1,3-dihydroindol -2-one;

(+)-5-Cyano-3-(2-ethoxyphenyl)-3-(4-pyridin-4-ylpiperazin-1-yl)-1-(quinoline-8-sulfonyl)-2,3-dihydro-1H-indol-2-one;

(+)-5-Cyano-3-(2-ethoxyphenyl)-1-(5-methylpyridine-2-sulfonyl)-3-(4-pyridin-4-yl-piperazin-1-yl)-2,3-dihydro-1H-indol -2-one;

5-Cyano-3-(2-ethoxy-5-methoxyphenyl)-3-[4-(2-methylpyridin-4-yl)-[1,4]diazepan-1-yl]-1-(quinoline-8-sulfonyl)-2,3-dihydro-1H-indol -2-one;

(+)-5-Cyano-3-(2-ethoxyphenyl)-1-(4-methylquinoline-8-sulfonyl)-3-(4-pyridin-4-yl-piperazin-1-yl)-2,3-dihydro-1H-indol -2-one;

(+)-5-Cyano-3-(2-ethoxyphenyl)-1-(5-methoxypyridine-2-sulfonyl)-3-(4-pyridin-4-yl-piperazin-1-yl)-2,3-dihydro-1H-indol -2-one;

5-Cyano-3-(2-ethoxy-5-methoxyphenyl)-1-(5-methoxypyridine-2-sulfonyl)-3-[4-(2-methylpyridin-4-yl)-[1,4]diazepan-1-yl]-2,3-dihydro-1H-indol -2-one;

5-Cyano-3-[4-(2-cyclopropylpyridin-4-yl) piperazin-1-yl]-3-(2-ethoxy-5-methoxyphenyl)-1-(quinoline-8-sulfonyl)-2,3-dihydro-1H-indol -2-one;

(+)-5-Cyano-3-(2-ethoxyphenyl)-1-(5-ethoxyquinoline-8-sulfonyl)-3-(4-pyridin-4-yl-piperazin-1-yl)-2,3-dihydro-1H-indol -2-one;

5-Cyano-3-(2-ethoxy-5-methoxyphenyl)-1-(5-methoxypyridine-2-sulfonyl)-3-(5-pyridin-4-ylhexahydropyrrolo[3,4-c]pyrrol-2-yl)-2,3-dihydro-1H-indol -2-one;

5-Cyano-3-(2-ethoxy-5-methoxyphenyl)-1-(5-methoxyquinoline-8-sulfonyl)-3-(4-piperidin-4-ylpiperazin-1-yl)-2,3-dihydro-1H-indol -2-one hydrochloride;

5-Cyano-3-[4-(2-cyclopropylpyridin-4-yl) piperazin-1-yl]-3-(2-ethoxy-5-methoxyphenyl)-1-(5-methoxyquinoline-8-sulfonyl)-2,3-dihydro-1H-indol -2-one;

5-Cyano-3-(6-chloro-2-ethoxypyridin-3-yl)-1-(5-methoxyquinoline-8-sulfonyl)-3-(4-pyridin-4-yl-[1,4]diazepan-1-yl)-2,3-dihydro-1H-indol -2-one;

5-Cyano-3-(2-ethoxy-5-methoxyphenyl)-3-[4-(2-ethylpyridin-4-yl) piperazin-1-yl]-1-(5-methoxyquinoline-8-sulfonyl)-2,3-dihydro-1H-indol -2-one;

5-Cyano-3-(2-ethoxy-5-methoxyphenyl)-1-(5-methoxyquinoline-8-sulfonyl)-3-[4-(2-methylpyridin-4-yl)-[1,4]diazepan-1-yl]-2,3-dihydro-1H-indol -2-one;

5-Cyano-3-(2-ethoxy-5-methoxyphenyl)-1-(5-methoxyquinoline-8-sulfonyl)-3-(5-pyridin-4-ylhexahydropyrrolo[3,4-c]pyrrol-2-yl)-2,3-dihydro-1H-indol -2-one;

(−)5Cyano-3-(2-ethoxy-5-methoxyphenyl)-1-(5-methoxypyridine-2-sulfonyl)-3-[4-(2-methylpyridin-4-yl) piperazin-1-yl]-2,3-dihydro-1H-indol -2-one;

(+)-5-Cyano-3-(2-ethoxy-5-methoxyphenyl)-1-(5-methylpyridine-2-sulfonyl)-3-[4-(2-methylpyridin-4-yl) piperazin-1-yl]-2,3-dihydro-1H-indol -2-one;

(+)-5-Cyano-3-(2-ethoxy-5-methoxyphenyl)-3-[4-(4-methylpiperazin-1-yl) piperidin-1-yl]-1-(4-methylquinoline-8-sulfonyl)-2,3-dihydro-1H-indol -2-one;

5-Cyano-3-(2-ethoxyphenyl)-1-(5-methoxypyridine-2-sulfonyl)-3-(4-pyridin-4-yl-[1,4]diazepan-1-yl)-2,3-dihydro-1H-indol -2-one;

5-Cyano-3-(2-ethoxyphenyl)-1-(5-methoxypyridine-2-sulfonyl)-3-[4-(2-methyl-pyridin-4-yl)piperazin-1-yl]-2,3-dihydro-1H-indol -2-one;

5-Cyano-3-(2-ethoxy-5-methoxyphenyl)-1-(5-methoxyquinoline-8-sulfonyl)-3-(4-pyridin-4-ylpiperazin-1-yl)-2,3-dihydro-1H-indol -2-one;

5-Cyano-3-(2-ethoxy-5-methoxyphenyl)-1-(5-fluoroquinoline-8-sulfonyl)-3-(4-pyridin-4-ylpiperazin-1-yl)-2,3-dihydro-1H-indol -2-one;

5-Cyano-3-(2-ethoxy-5-methoxyphenyl)-1-(5-methoxypyridine-2-sulfonyl)-3-(4-pyridin-4-ylpiperazin-1-yl)-2,3-dihydro-1H-indol -2-one;

5-Cyano-3-(2-ethoxyphenyl)-1-(5-methoxypyridine-2-sulfonyl)-3-[4-(1-methyl-piperidin-4-yl)piperazin-1-yl]-2,3-dihydro-1H-indol -2-one;

5-Cyano-3-(2-ethoxyphenyl)-1-(4-ethylquinoline-8-sulfonyl)-3-(4-pyridin-4-yl-piperazin-1-yl)-2,3-dihydro-1H-indol-2-one;

5-Cyano-3-(2-ethoxy-5-methoxyphenyl)-1-(5-methoxypyridine-2-sulfonyl)-3-(4-piperazin-1-ylpiperidin-1-yl)-2,3-dihydro-1H-indol -2-one;

5-Cyano-3-(2-ethoxy-5-methoxyphenyl)-1-(5-methoxyquinoline-8-sulfonyl)-3-(4-piperazin-1-ylpiperidin-1-yl)-2,3-dihydro-1H-indol-2-one hydrochloride;

5-Cyano-3-(2-ethoxyphenyl)-1-(5-methylquinoline-8-sulfonyl)-3-(4-pyridin-4-yl-piperazin-1-yl)-2,3-dihydro-1H-indol -2-one;

5-Cyano-3-(2-ethoxy-5-methoxyphenyl)-1-(5-methoxypyridine-2-sulfonyl)-3-[4-(1-methylpiperidin-4-yl)piperazin-1-yl]-2,3-dihydro-1H-indol -2-one;

5-Cyano-3-[4-(2-cyclopropylpyridin-4-yl)piperazin-1-yl]-3-(2-ethoxy-5-methoxyphenyl)-1-(5-methoxypyridine-2-sulfonyl)-2,3-dihydro-1H-indol-2-one;

5-Cyano-3-(2-ethoxy-5-methoxyphenyl)-3-[4-(2isopropylpyridin-4-yl) piperazin-1-yl]-1-(5-methoxypyridine-2-sulfonyl)-2,3-dihydro-1H-indol -2-one;

5-Chloro-1-(4-methoxybenzenesulfonyl)-3-(2-methoxypyridin-3-yl)-3-(4-thiazol-2-yl-piperazin-1-yl)-1,3-dihydroindol -2-one;

5-Chloro-1-(2,4-dimethoxybenzenesulfonyl)-3-(2-methoxypyridin-3-yl)-3-(4-thiazol-2-ylpiperazin-1-yl)-1,3-dihydroindol -2-one;

5-Chloro-1-(2,4-dimethoxybenzenesulfonyl)-3-(2-methoxypyridin-3-yl)-3-(4-pyridin-4-ylpiperazin-1-yl)-1,3-dihydroindol -2-one;

5-Chloro-1-(4-methoxybenzenesulfonyl)-3-(2-methoxypyridin-3-yl)-3-(4-pyridin-4-yl-piperazin-1-yl)-1,3-dihydroindol -2-one;

5-Chloro-1-(2,4-dimethoxybenzenesulfonyl)-3-(2-methoxypyridin-3-yl)-3-[4-(4-cyanopyridin-2-yl)piperazin-1-yl]-1,3-dihydroindol -2-one;

5-Chloro-1-(2-methoxy-4-methylbenzenesulfonyl)-3-(2-methoxypyridin-3-yl)-3-(4-pyridin-4-ylpiperazin-1-yl)-1,3-dihydroindol -2-one;

5-Chloro-1-(4-cyanobenzenesulfonyl)-3-(2-methoxypyridin-3-yl)-3-(4-pyridin-4-yl-piperazin-1-yl)-1,3-dihydroindol -2-one;

5-Chloro-1-(2-methoxybenzenesulfonyl)-3-(2-methoxypyridin-3-yl)-3-(4-pyridin-4-yl-piperazin-1-yl)-1,3-dihydroindol -2-one;

5-Chloro-1-(2,4-dimethoxybenzenesulfonyl)-3-[4-(4-methoxyphenyl)piperazin-1-yl]-3-(2-methoxypyridin-3-yl)-1,3-dihydroindol -2-one;

5-Chloro-1-(2,4-dimethoxybenzenesulfonyl)-3-(2-methoxypyridin-3-yl)-3-(4-pyridin-2-ylpiperazin-1-yl)-1,3-dihydroindol-2-one;

5-Chloro-1-(2-fluorobenzenesulfonyl)-3-(2-methoxypyridin-3-yl)-3-(4-pyridin-4-yl-piperazin-1-yl)-1,3-dihydroindol-2-one;

5-Chloro-1-(4-fluorobenzenesulfonyl)-3-(2-methoxypyridin-3-yl)-3-(4-pyridin-4-yl-piperazin-1-yl)-1,3-dihydroindol-2-one;

5-Chloro-1-(3,4-dimethoxybenzenesulfonyl)-3-(2-methoxypyridin-3-yl)-3-(4-pyridin-2-ylpiperazin-1-yl)-1,3-dihydroindol-2-one;

5-Chloro-3-(3,4-dimethoxyphenyl)-3-(4-pyridin-4-ylpiperazin-1-yl)-1-(quinoline-8-sulfonyl)-1,3-dihydroindol-2-one;

5-Chloro-3-(3-dimethylaminomethylphenyl)-3-(4-pyridin-4-ylpiperazin-1-yl)-1-(quinoline-8-sulfonyl)-1,3-dihydroindol-2-one;

5-Chloro-3-(2-methoxymethylphenyl)-3-(4-pyridin-4-ylpiperazin-1-yl)-1-(quinoline-8-sulfonyl)-1,3-dihydroindol-2-one;

5-Cyano-3-(2-ethoxyphenyl)-3-[4-(2-ethoxypyridin-4-yl)piperazin-1-yl]-1-(quinoline-8-sulfonyl)-1,3-dihydroindol-2-one;

5-Cyano-3-(2-ethoxyphenyl)-3-[4-(2-chloropyridin-4-yl)piperazin-1-yl]-1-(quinoline-8-sulfonyl)-1,3-dihydroindol-2-one;

5-Cyano-3-(2-ethoxyphenyl)-3-[4-(1-oxidopyridin-4-yl)piperazin-1-yl]-1-(quinoline-8-sulfonyl)-1,3-dihydroindol-2-one;

5-Cyano-3-(2-ethoxyphenyl)-3-(4-[1,3,5]triazin-2-ylpiperazin-1-yl)-1-(quinoline-8-sulfonyl)-1,3-dihydroindol-2-one;

5-Cyano-3-(2-ethoxyphenyl)-3-(4-pyrimidin-4-ylpiperazin-1-yl)-1-(quinoline-8-sulfonyl)-1,3-dihydroindol-2-one;

5-Cyano-3-(2-ethoxyphenyl)-3-((1S,4S)-5-pyridin-4-yl-2,5-diazabicyclo [2.2.1]hept-2-yl)-1-(quinoline-8-sulfonyl)-1,3-dihydroindol-2-one;

5-Chloro-3-(2-methoxyphenyl)-3-((1S,4S)-5-pyridin-4-yl-2,5-diaza-bicyclo[2.2.1]hept-2-yl)-1-(quinoline-8-sulfonyl)-1,3-dihydroindol-2-one;

5-Cyano-3-(2-ethoxyphenyl)-1-(2-methylquinoline-8-sulfonyl)-3-(4-pyridin-4-piperazin-1-yl)-1,3-dihydroindol-2-one;

5-Cyano-3-(2-ethoxyphenyl)-3-[4-(3-fluoropyridin-4-yl)piperazin-1-yl]-1-(quinoline-8-sulfonyl)-1,3-dihydroindol-2-one;

5-Cyano-3-(2-ethoxyphenyl)-3-[4-(2-fluoropyridin-4-yl)piperazin-1-yl]-1-(quinoline-8-sulfonyl)-1,3-dihydroindol-2-one;

5-Cyano-1-(2,5-dimethylthiophene-3-sulfonyl)-3-(2-ethoxyphenyl)-3-(4-pyridin-4-yl-piperazin-1-yl)-1,3-dihydroindol-2-one;

5-Cyano-1-(thiophene-2-sulfonyl)-3-(2-ethoxyphenyl)-3-(4-pyridin-4-ylpiperazin-1-yl)-1,3-dihydroindol-2-one;

5-Cyano-1-(5-chlorothiophene-2-sulfonyl)-3-(2-ethoxyphenyl)-3-(4-pyridin-4-yl-piperazin-1-yl)-1,3-dihydroindol-2-one;

5-Cyano-1-(thiophene-3-sulfonyl)-3-(2-ethoxyphenyl)-3-(4-pyridin-4-ylpiperazin-1-yl)-1,3-dihydroindol-2-one;

5-Cyano-3-(2-ethoxyphenyl)-1-(8-methoxyquinoline-5-sulfonyl)-3-(4-pyridin-4-yl-piperazin-1-yl)-1,3-dihydroindol-2-one;

5-Cyano-3-(2-ethoxyphenyl)-3-(4-pyridin-4-ylpiperazin-1-yl)-1-(6-methylquinoline-8-sulfonyl)-1,3-dihydroindol-2-one;

5-Cyano-3-(2-ethoxyphenyl)-3-(4-pyridin-4-ylpiperazin-1-yl)-1-(7-methylquinoline-8-sulfonyl)-1,3-dihydroindol-2-one;

5-Cyano-3-(6-chloro-2-methoxypyridin-3-yl)-3-(4-pyridin-4-ylpiperazin-1-yl)-1-(2,4-dimethoxybenzenesulfonyl)-2,3-dihydro-1H-indol-2-one;

5-Cyano-3-(2-ethoxy-5-methoxyphenyl)-1-(4-methylquinoline-8-sulfonyl)-3-((1S,4S)-5-pyridin-4-yl-2,5-diazabicyclo[2.2.1]hept-2-yl)-2,3-dihydro-1H-indol-2-one;

5-Cyano-3-(2-ethoxy-5-methoxyphenyl)-1-(quinoline-8-sulfonyl)-3-((1S,4S)-5-pyridin-4-yl-2,5-diazabicyclo [2.2.1]hept-2-yl)-2,3-dihydro-1H-indol-2-one;

(3R)-5-Cyano-3-(2-ethoxy-5-methoxyphenyl)-1-(quinoline-8-sulfonyl)-3-((1S,4S)-5-pyridin-4-yl-2,5-diazabicyclo[2.2.1]hept-2-yl)-2,3-dihydro-1H-indol-2-one;

5-Cyano-3-(2,6-dimethoxypyridin-3-yl)-3-(4-pyridin-4-ylpiperazin-1-yl)-1-(quinoline-8-sulfonyl)-1,3-dihydroindol-2-one;

5-Cyano-3-(2,6-dimethoxypyridin-3-yl)-1-(2,4-dimethoxybenzenesulfonyl)-3-(4-pyridin-4-ylpiperazin-1-yl)-2,3-dihydro-1H-indol-2-one;

5-Cyano-3-(6-chloro-2-ethoxypyridin-4-yl)-1-(5-methylpyridine-2-sulfonyl)-3-(4-pyridin-4-ylpiperazin-1-yl)-2,3-dihydro-1H-indol-2-one;

5-Cyano-3-(6-chloro-2-ethoxypyridin-4-yl)-3-(4-pyridin-4-ylpiperazin-1-yl)-1-(quinoline-8-sulfonyl)-1,3-dihydroindol-2-one;

5-Cyano-3-(2-ethoxyphenyl)-3-[4-(3,5-dichloropyridin-4-yl)piperazin-1-yl]-1-(quinoline-8-sulfonyl)-2,3-dihydro-1H-indol-2-one;

5-Cyano-3-(2,5-dimethoxyphenyl)-1-(5-methylpyridine-2-sulfonyl)-3-[4-(2-trifluoromethylpyridin-4-yl)piperazin-1-yl]-2,3-dihydro-1H-indol-2-one;

5-Cyano-3-(2,5-dimethoxyphenyl)-1-(5-methylpyridine-2-sulfonyl)-3-[4-(2-trifluoromethylpyridin-4-yl)piperazin-1-yl]-2,3-dihydro-1H-indol-2-one;

(+)-5-Cyano-3-(2-ethoxy-5-methoxy-phenyl)-1-(5-methoxy-pyridine-2-sulfonyl)-3-(4-piperidin-4-yl-piperazin-1-yl)-2,3-dihydro-1H-indol-2-one;

(+)-5-Cyano-3-(2-ethoxy-5-methoxy-phenyl)-1-(5-methoxy-pyridine-2-sulfonyl)-3-[4-(1-methyl-piperidin-4-yl)-piperazin-1-yl]-2,3-dihydro-1H-indol-2-one;

(+)-5-Cyano-3-(2-ethoxy-4-methoxy-phenyl)-1-(5-methoxy-pyridine-2-sulfonyl)-3-(4-piperazin-1-yl-piperidin-1-yl)-2,3-dihydro-1H-indol-2-one;

(+)-5-Cyano-3-(2-ethoxy-5-methoxy-phenyl)-3-[4-(2-isopropyl-pyridin-4-yl)-piperazin-1-yl]-1-(5-methoxy-pyridine-2-sulfonyl)-2,3-dihydro-1H-indol-2-one;

5-Cyano-3-(2-ethoxy-4-fluoro-phenyl)-1-(5-methoxy-pyridine-2-sulfonyl)-3-[4-(2-methyl-pyridin-4-yl)-piperazin-1-yl]-2,3-dihydro-1H-indol-2-one;

5-Cyano-3-(2-ethoxy-5-methoxy-phenyl)-3-[4-(4-ethyl-piperazin-1-yl)-piperidin-1-yl]-1-(5-methoxy-pyridine-2-sulfonyl)-2,3-dihydro-1H-indol-2-one;

5-Cyano-3-(2-ethoxy-5-methoxy-phenyl)-3-[4-(2-ethyl-pyridin-4-yl)-piperazin-1-yl]-1-(5-methoxy-pyridine-2-sulfonyl)-2,3-dihydro-1H-indol-2-one;

5-Cyano-3-(2-ethoxy-4-fluoro-phenyl)-1-(5-methoxy-pyridine-2-sulfonyl)-3-(4-pyridin-4-yl-[1,4]diazepan-1-yl)-2,3-dihydro-1H-indol-2-one;

5-Cyano-3-(6-chloro-2-ethoxy-pyridin-3-yl)-1-(5-methoxy-pyridine-2-sulfonyl)-3-(5-pyridin-4-yl-hexahydro-pyrrolo[3,4-c]pyrrol-2-yl)-2,3-dihydro-1H-indol -2-one;

5-Cyano-3-(6-chloro-2-ethoxy-pyridin-3-yl)-1-(5-methoxy-pyridine-2-sulfonyl)-3-[5-(2-methyl-pyridin-4-yl)-hexahydro-pyrrolo[3,4-c]pyrrol-2-yl]-2,3-dihydro-1H-indol-2-one;

5-Cyano-3-(2-ethoxy-phenyl)-3-[4-(2-isopropyl-pyridin-4-yl)-piperazin-1-yl]-1-(5-methoxy-pyridine-2-sulfonyl)-2,3-dihydro-1H-indol -2-one;

(+)-5-Cyano-3-(6-chloro-2-ethoxy-pyridin-3-yl)-1-(5-methoxy-pyridine-2-sulfonyl)-3-[4-(2-methyl-pyridin-4-yl)-piperazin-1-yl]-2,3-dihydro-1H-indol-2-one;

(+)-5-Cyano-3-(6-chloro-2-ethoxy-pyridin-3-yl)-1-(5-methoxy-pyridine-2-sulfonyl)-3-[4-(2-methyl-pyridin-4-yl)-piperazin-1-yl]-2,3-dihydro-1H-indol-2-one;

5-Cyano-3-(2-ethoxy-4-fluoro-p henyl)-3-[4-(2-isopropyl-pyridin-4-yl)-piperazin-1-yl]-1-(5-methoxy-pyridine-2-sulfonyl)-2,3-dihydro-1H-indol -2-one;

5-Cyano-3-(2-ethoxy-5-methoxy-phenyl)-3-[4-(2-is opropyl-pyridin-4-yl)-[1,4]diazepan-1-yl]-1-(5-methoxy-pyridine-2-sulfonyl)-2,3-dihydro-1H-indol-2-one;

5-Cyano-3-(6-chloro-2-ethoxy-pyridin-3-yl)-1-(5-methoxy-pyridine-2-sulfonyl)-3-((1S,4S)-5-pyridin-4-yl-2,5-diaza-bicyclo [2.2.1]hept-2-yl)-2,3-dihydro-1H-indol -2-one;

(+)-5-Cyano-3-(2-ethoxy-5-methoxy-phenyl)-1-(5-methoxy-pyridine-2-sulfonyl)-3-(4-piperazin-1-yl-piperidin-1-yl)-2,3-dihydro-1H-indol-2-one;

5-Cyano-3-(2-ethoxy-4-methoxy-phenyl)-3-(4-pyridin-4-yl-piperazin-1-yl)-1-(quinoline-8-sulfonyl)-2,3-dihydro-1H-indol -2-one;

(+)-5-Cyano-3-(2-ethoxy-5-methoxy-phenyl)-1-(5-methoxy-pyridine-2-sulfonyl)-3-[4-(4-methyl-piperazin-1-yl)-piperidin-1-yl]-2,3-dihydro-1H-indol -2-one;

5-Cyano-3-(2-ethoxy-5-methyl-phenyl)-1-(5-methoxy-quinoline-8-sulfonyl)-3-(4-pyridin-4-yl-piperazin-1-yl)-2,3-dihydro-1H-indol -2-one;

5-Cyano-3-(2-ethoxy-5-ethyl-phenyl)-1-(5-methoxy-quinoline-8-sulfonyl)-3-[4-(2-methyl-pyridin-4-yl)-piperazin-1-yl]-2,3-dihydro-1H-indol -2-one;

5-Cyano-3-(2-ethoxy-5-methoxy-phenyl)-1-(5-methoxy-quinoline-8-sulfonyl)-3-[4-(1-methyl-piperidin-4-yl)-piperazin-1-yl]-2,3-dihydro-1H-indol -2-one;

(+)-5-Cyano-3-(2-ethoxy-5-methoxy-phenyl)-1-(5-methoxy-quinoline-8-sulfonyl)-3-(4-pyridin-4-yl-piperazin-1-yl)-2,3-dihydro-1H-indol -2-one;

(+)-5-Cyano-3-(2-ethoxy-5-methoxy-phenyl)-1-(5-methoxy-pyridine-2-sulfonyl)-3-(4-pyridin-4-yl-piperazin-1-yl)-2,3-dihydro-1H-indol -2-one;

(+)-5-Cyano-3-(2-ethoxy-5-methoxy-phenyl)-1-(5-methoxy-pyridine-2-sulfonyl)-3-[4-(2-methyl-pyridin-4-yl)-piperazin-1-yl]-2,3-dihydro-1H-indol -2-one;

5-Cyano-3-(2-ethoxy-5-ethyl-phenyl)-1-(5-methoxy-pyridine-2-sulfonyl)-3-[4-(2-methyl-pyridin-4-yl)-piperazin-1-yl]-2,3-dihydro-1H-indol -2-one;

5-Cyano-3-(2-ethoxy-5-ethyl-phenyl)-3-[4-(2-isopropyl-pyridin-4-yl)-piperazin-1-yl]-1-(5-methoxy-pyridine-2-sulfonyl)-2,3-dihydro-1H-indol-2-one;

5-Cyano-3-(6-chloro-2-ethoxy-pyridin-3-yl)-3-[4-(2-isopropyl-pyridin-4-yl)-piperazin-1-yl]-1-(5-methoxy-pyridine-2-sulfonyl)-2,3-dihydro-1H-indol -2-one;

5-Cyano-3-(6-chloro-2-ethoxy-pyridin-3-yl)-1-(5-methoxy-pyridine-2-sulfonyl)-3-(4-pyridin-4-yl-[1,4]diazepan-1-yl)-2,3-dihydro-1H-indol-2-one;

5-Cyano-3-(2-ethoxy-5-methyl-phenyl)-1-(5-methoxy-pyridine-2-sulfonyl)-3-(4-pyridin-4-yl-piperazin-1-yl)-2,3-dihydro-1H-indol -2-one;

5-Cyano-3-(6-chloro-2-ethoxy-pyridin-3-yl)-1-(5-methoxy-pyridine-2-sulfonyl)-3-[4-(4-methyl-piperazin-1-yl)-piperidin-1-yl]-2,3-dihydro-1H-indol -2-one;

5-Cyano-3-(2-ethoxy-4-methoxy-phenyl)-1-(5-methoxy-pyridine-2-sulfonyl)-3-[4-(4-methyl-piperazin-1-yl)-piperidin-1-yl]-2,3-dihydro-1H-indol -2-one;

5-Cyano-3-(2-ethoxy-5-methoxy-phenyl)-1-(5-methoxy-pyridine-2-sulfonyl)-3-(4-piperidin-4-yl-piperazin-1-yl)-2,3-dihydro-1H-indol -2-one as hydrochloride acid addition;

5-Cyano-3-(2-ethoxy-3-methoxy-phenyl)-3-[4-(2-isopropyl-pyridin-4-yl)-piperazin-1-yl]-1-(5-methoxy-pyridine-2-sulfonyl)-2,3-dihydro-1H-indol-2-one;

5-Cyano-3-(2-ethoxy-4-methoxy-phenyl)-1-(5-methoxy-pyridine-2-sulfonyl)-3-(4-piperazin-1-yl-piperidin-1-yl)-2,3-dihydro-1H-indol -2-one;

5-Cyano-3-(2-ethoxy-4-methoxy-phenyl)-3-[4-(2-isopropyl-pyridin-4-yl)-piperazin-1-yl]-1-(5-methoxy-pyridine-2-sulfonyl)-2,3-dihydro-1H-indol-2-one;

5-Cyano-3-(6-chloro-2-ethoxy-pyridin-3-yl)-1-(5-methoxy-pyridine-2-sulfonyl)-3-(4-piperidin-4-yl-piperazin-1-yl)-2,3-dihydro-1H-indol -2-one;

5-Cyano-3-(6-chloro-2-ethoxy-pyridin-3-yl)-1-(5-methoxy-pyridine-2-sulfonyl)-3-[4-(2-methyl-pyridin-4-yl)-[1,4]diazepan-1-yl]-2,3-dihydro-1H-indol -2-one;

5-Cyano-3-(2-ethoxy-4-methoxy-phenyl)-1-(5-methoxy-pyridine-2-sulfonyl)-3-[4-(2-methyl-pyridin-4-yl)-piperazin-1-yl]-2,3-dihydro-1H-indol -2-one;

5-Cyano-3-(2-ethoxy-3-methoxy-phenyl)-1-(5-methoxy-pyridine-2-sulfonyl)-3-[4-(2-methyl-pyridin-4-yl)-piperazin-1-yl]-2,3-dihydro-1H-indol -2-one;

5-Cyano-3-(2-ethoxy-5-methyl-phenyl)-1-(5-methoxy-pyridine-2-sulfonyl)-3-[4-(2-methyl-pyridin-4-yl)-piperazin-1-yl]-2,3-dihydro-1H-indol -2-one;

5-Cyano-3-[4,4']bipiperidinyl-1-yl-3-(2-ethoxy-5-methoxy-phenyl)-1-(5-methoxy-pyridine-2-sulfonyl)-2,3-dihydro-1H-indol -2-one; and 5-Cyano-3-(6-chloro-2-ethoxy-pyridin-3-yl)-1-(5-methoxy-pyridine-2-sulfonyl)-3-(4-piperazin-1-yl-piperidin-1-yl)-2,3-dihydro-1H-indol -2-one.

\* \* \* \* \*

UNITED STATES PATENT AND TRADEMARK OFFICE
CERTIFICATE OF CORRECTION

| | | |
|---|---|---|
| PATENT NO. | : 8,486,931 B2 | Page 1 of 1 |
| APPLICATION NO. | : 12/529542 | |
| DATED | : July 16, 2013 | |
| INVENTOR(S) | : Geneste et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 473 days.

Signed and Sealed this
Sixteenth Day of December, 2014

Michelle K. Lee
*Deputy Director of the United States Patent and Trademark Office*